United States Patent [19]

Marklund et al.

[11] Patent Number: 5,366,729

[45] Date of Patent: Nov. 22, 1994

[54] NON-GLYCOSYLATED VARIANTS OF EXTRACELLULAR SUPEROXIDE DISMUTASE (EC-SOD)

[75] Inventors: Stefan Marklund; Thomas Edlund, both of Umeå, Sweden

[73] Assignee: Symbicom Aktiebolag, Umea, Sweden

[21] Appl. No.: 856,077

[22] PCT Filed: Sep. 17, 1990

[86] PCT No.: PCT/DK90/00238

§ 371 Date: May 13, 1992

§ 102(e) Date: May 13, 1992

[87] PCT Pub. No.: WO91/04315

PCT Pub. Date: Apr. 4, 1991

[30] Foreign Application Priority Data

Sep. 15, 1989 [DK] Denmark ............... 4557/89

[51] Int. Cl.$^5$ .................... A61K 37/50; C12N 5/10; C12N 9/02; C12N 15/53
[52] U.S. Cl. ................... 424/94.4; 435/189; 435/240.2; 435/320.1; 536/23.2
[58] Field of Search ............... 424/94.1, 94.4; 435/68.1, 69.1, 172.3, 189, 240.2, 320.1; 935/70; 536/23.2

[56] References Cited

U.S. PATENT DOCUMENTS

| | | | |
|---|---|---|---|
| 4,530,901 | 7/1985 | Weissmann | 435/70 |
| 4,738,927 | 4/1988 | Taniguchi et al. | 435/243 |
| 4,742,004 | 5/1988 | Hartman et al. | 435/70 |
| 5,130,245 | 7/1992 | Marklund et al. | 435/189 |

FOREIGN PATENT DOCUMENTS

| | | |
|---|---|---|
| 0019477 | 11/1980 | European Pat. Off. . |
| 0045222 | 3/1982 | European Pat. Off. . |
| 0112299 | 6/1984 | European Pat. Off. . |
| 0138111 | 4/1985 | European Pat. Off. . |
| 0180964 | 5/1986 | European Pat. Off. . |

(List continued on next page.)

OTHER PUBLICATIONS

Adachi, T. and Marklund, S.: Interactions Between Human Extracellular Superoxide Dismutase C and Sulfated Polysaccharides. J. Biol. Chem. 264: 8537–8541 (1989).

Botstein, D. and Shortle, D.: Strategies and Applications of in Vitro Mutagenesis. Science 229: 1193–1201 (1985).

Hjalmarsson, K. et al.: Isolation and Sequence of Complementary DNA Encoding Human Extracellular Superoxide Dismutase. Proc. Natl. Acad. Sci. USA 84: 6340–6344 (1987).

Karlsson, K.: Extracellular Superoxide Dismutase; Association with Glycosaminoglycans. Umea University Medical Dissertations, Umea, Sweden, Series 227 (1988).

(List continued on next page.)

*Primary Examiner*—Robert A. Wax
*Assistant Examiner*—Eric Grimes
*Attorney, Agent, or Firm*—Iver A. Cooper

[57] ABSTRACT

Extracellular superoxide dismutase (EC-SOD) variants having the superoxide dismutating property of the native EC-SOD and having a modified (reduced or increased) binding to heparin as compared to recombinant EC-SOD C as well as compositions comprising such variants. The EC-SOD variants are polypeptides comprising: 1) amino acids 1–193 of native EC-SOD C and 2) an amino acid sequence which is based on, but different from amino acid moieties 194–222 of recombinant EC-SOD C, either by being truncated or prolonged at the C-terminal end or by having substituted or otherwise modified one or more amino acid moieties of the sequence. Another EC-SOD variant is one which differs from recombinant EC-SOD C by being a glycosylation-free mutant. The variants may be produced by recombinant DNA techniques and are useful in the treatment of various diseases.

14 Claims, 27 Drawing Sheets

FOREIGN PATENT DOCUMENTS

| | | |
|---|---|---|
| 0213628 | 3/1987 | European Pat. Off. . |
| 0275202 | 7/1988 | European Pat. Off. . |
| 0414915 | 3/1991 | European Pat. Off. . |
| WO8701387 | 3/1987 | WIPO . |
| WO90/10694 | 1/1991 | WIPO . |

OTHER PUBLICATIONS

Karlsson, K. and Marklund, S.: Plasma Clearance of Human Extracellular Superoxide Dismutase C in Rabbits. J. Clin. Invest. 82: 762–766 (1988).

Sandstrom, J. et al.: The Heparin–Binding Domain of Extracellular Superoxide Dismutase C and Formation of Variants with Reduced Heparin Affinity. J. Biol. Chem. 267: 18205–18209 (1992).

Tibell, L. et al.: Expression of Human Extracellular Superoxide Dismutase in Chinese Hamster Ovary Cells and Characterization of the Product. Proc. Natl. Acad. Sci. USA 84: 6634–6638 (1987).

Lathe, R., "Synthetic Oligonuleotide Probes Deduced from Amino Acid Sequence Data", *J. Mol. Biol.*, 183: 1–12 (1985).

Milton et al., "In Vitro Mutagenesis and Overexpression of the *Escherichia coli* trpA Gene and the Partial Characterization of the Resultant Trptophan Synthase Mutant α–Subunits", *The Journal of Biological Chemistry*, 261(35): 16604–16615, 1986.

Bannister, et al., "The presence of a copper/zinc dismutase in the bacterium *Photobacterium leiognathi*: A Likely case of gene transfer from eukaryotes to prokaryotes", *Proc. Natl. Acad. Sci. USA*, 82: 149–152, 1985.

Duplay et al., "Linker mutagenesis in the gene encoding the periplasmic maltose-binding protein of *E. coli* ", *Biochemie*, 67: 849–851, 1985.

Fridovich, Irwin, "Superoxide Dismutases", *Advances in Enzymology*, vol. 64, pp. 61–97. (1986).

Wells et al., "Cassette mutagenesis: an efficient method for generation of multiple mutations at defined sites", *Gene*, 34: 315–323, 1985.

Myers et al., "A General Method of Saturation Mutagenesis of Cloned DNA Fragments", *Science*, 229: 242–247, 1985.

Abarzua et al, "Enzymatic techniques for the isolation of random single-base substitutions in vitro at high frequency", *Proc. Natl. Acad. Sci. USA*, 81: 2030–2034, 1984.

Borders et al., "Identification of ARG–143 as the Essential Arginyl Residue in Yeast Cu,Zn Superoxide Dismutase by use of a Chromophoric Arginine Reagent", *Biochemical and Biophysical Research Communications*, 96(3): 1071–1078, 1980.

Malinowski et al, "Chemical Modification of Arginine at the Active Site of the Bovine Erythrocyte Superoxide Dismutase", *Biochemistry*, 18(26): 5909–5917, 1979.

Sieffens et al, "The Primary Structure of Cu,Zn Superoxide Dismutase from *Photobacterium leiognathi*: A likely case of gene transfer from eukaryotes to prokaryotes", Hopee-Seyler Z. Physiol. Chem. 364: 675–690 (1983).

Rocha et al., "The amino–acid sequence of copper/zinc superoxide dismutase from swordfish liver", *Eur. J. Biochem.*, 145:477–484 (1984).

Lee et al., "Superoxide dismutase: An evolutionary puzzle", *Proc. Natl. Acad. Sci. USA*, 82: 824–828, 1985.

Steinman, Howard M., "The Amino Acid Sequence of Copper-Zinc Superoxide Dismutase from Bakers' Yeast", *The Journal of Biological Chemistry*, 255(14): 6758–6765, 1980.

Kitagawa et al., "Amino Acid Sequence of Copper,Zinc–Superoxide Dismutase from Spinach Leaves", *J. Biochem.*, 99: 1289–1298, 1986.

Hering et al., "The Primary Structure of Porcine Cu-Zn Superoxide Dismutase", *Biol. Chem.*, 366: 435–445, 1985.

Lerch et al., "Amino Acid Sequence of Copper–Zinc Superoxide Dismutase from Horse Liver", *The Journal of Biological Chemistry*, 256(22): 11545–11551, 1982.

Steinman et al., "Bovine Erythrocyte Superoxide Dismutase", *The Journal of Biological Chemistry*, 249(22): 7326–7338, 1974.

Sherman et al., "Nucleotide sequence and expression of human chromosome 21–encoded superoxide dismutase mRNA", *Proc. Natl. Acad. Sci. USA* , 80: 5465–5469, 1983.

Tainer et al., "Determination and Analysis of the 2 A Structure of Copper, Zinc Superoxide Dismutase", *J. Mol. Biol.*, 160: 181–217, 1982.

Bermingham-McDonogh et al., "Reduced anion-af- (List continued on next page.)

OTHER PUBLICATIONS finity of Cu,Zn Superoxide Dismutases chemically modified at arginine", *Biochemical and Biophysical Research Communication*, 108(4): 1376–1382, 1982.

Borders et al., "Essential Arginyl Residues in Cu,Zn Superoxide Dismutase from Saccharomyces Cervisiae", *Carlsberg Res. Commun.*, 45 : 185–194, 1980.

Getzoff et al., "Electrostatic recognition between superoxide and copper, zinc superoxide dismutase", *Nature*, 306: 287–290, 1983.

Tainer et al., "Structure and mechanism of copper, zinc superoxide dismutase", *Nature*, 306: 284–286, 1983.

Borders et al., "Essentiality of the active-site arginine residue for the normal catalytic activity of Cu,Zn superoxide dismutase", *Biochem. J.*, 230: 771–776, 1985.

McLachlan, A. D., "Tests for Comparing Related Amino-acid Sequences", *J. Mol. Biol.*, 61: 409–424, 1971.

Botstein et al., "Strategies and Applications of in Vitro Mutagenesis ", *Science*, 229(4719): 1193–1201, 1985.

Fasano et al., "Analysis of the transforming potential of the human H-ras gene by random mutagenesis", *Proc. Natl. Acad. Sci. USA*, 81: 4008–4012, 1984.

Suzuki et al., "Domain Structure of Vitronectin", *The Journal of Biological Chemistry*, 269(24): 15307–15314, 1984.

Calaycay et al., "Primary Structure of a DNA- and Heparin-binding Domain (Domain III) in Human Plasma Fibronectin", *The Journal of Biological Chemistry*, 260(22): 12136–12141, 1985.

Amuro et al., "Replacement by Site-directed Mutagenesis Indicates a Role for Histidien 170 in the Glutamine Amide Transfer Function of Anthranilate Synthase", *The Journal of Biological Chemistry*, 260–27, 14844–14849, 1985.

Hjalmarsson et al., "Isolation and sequence of complementary DNA encoding human extracellular superoxide dismutase", *Proc. Natl. Acad. Sci. USA*, 84: 6340–6344, 1987.

Adachi et al., "Interactions between Human Extracellular Superoxide Dismutase C and Sulfated Polysaccharides", *The Journal of Biological Chemistry*, 264(15): 8537–8541, 1989.

Kortt et al., "Amino acid sequences of hemoglobins I and II from root nodules of the non-leguminous parasponio rigida–rhizobium symbiosis, and a correction of the sequence of hemoglobin I from *Parasponia andersonii*", *Eur. J. Biochem.*, 175: 141–149, 1988.

Godovac-Zimmerman, Jasminka, "Isolation, Characterization and N -Terminal Amino-Acid Sequence of Rabbit Transferrin", *Biol. Chem. Hoppe-Seyler*, 369, 93–96, 1988.

Chen et al., "Primary structure of major outer-membrance protein I (ompF protein, porin) of *Escherichia coli* B/r", *Biochem. J.*, 203: 33–43, 1982.

Ozols et al., "Correction of the Amino Acid Sequence of Calf Liver Microsomal Cytochroms $b_5$", *The Journal of Biological Chemistry*, 244(24): 6617–6618, 1969.

Gibson et al., "Revision of the Blocked N Terminus of Rat Heart Fatty Acid-binding Protein by Liquid Secondary Ion Mass Spectrometry", *The Journal of Biological Chemistry*, 263(9): 4182–4185, 1988.

Fuchsman, William H., "Descrepancies among Published Amino Acid Sequences of Soybean Leghemoglobins: Experimental Evidence against Cultivar Differences as the Sources of the Discrepencies", *Archives of Biochemistry and Biophysics*, 243(2): 454–460, 1985.

Mazrimas et al., "A corrected primary sequence for bull protamine", *Biochemica et Biophysica Acta*, 872: 11–15, 1986.

Hu et al., "Cloning and Characterization of the Gene for Rabbit C-Reactive Protein", *Biochemistry*, 25: 7834–7839, 1986.

Panneerselvam et al., "Bovine parathymosin: Amino acid sequence and comparison with rat parathymosin", *Biochemical and Biophysical Research Communications*, 155(2): 539–545, 1988.

Mitchel et al., "The Complete Amino Acid Sequence of Papain", *The Journal of Biological Chemistry*, 26(14): 3485–3492, 1970.

Knecht et al., "Sequence Determination of Eglin C Using Combined Microtechniques of Amino Acid Analysis, Peptide Isolation, and Automatic Edman Degradation", *Analytical Biochemistry*, 130: 65–71, 1983.

Schneider et al, "Procedure for production of hybrid genes and proteins and its use in assessing significance of amino acid differences in homologous tryptophan sythetase α polypeptides", *Proc. Natl. Acad. Sci. USA*, 78(4): 2169–2173, 1981.

Fersht et al., "Fine Structure-Activity Analysis of Mu- (List continued on next page.)

OTHER PUBLICATIONS tations at Position 51 of Tyrosyl-tRNA Synthetase", *Biochemistry*, 24: 5858–5861, 1985.

Carter et al., "The Use of Double Mutants to Detect Structural Changes in the Active Site of the Tyrosyl-tRNA Synthetase (*Bacillus stearothermophilus*)", *Cell*, 38: 835–840, 1984.

Parge et al., "Crystallographic Characterization of Recombinant Human CuZN Superoxide Dismutase", *The Journal of Biological Chemistry*, 261(34): 16215–16218, 1986.

Beyer et al., "Examination of the Role of Arginine-143 in the Human Copper and Zinc Superoxide Dismutase by Site-specific Mutagenesis", *The Journal of Biological Chemistry*, 262(23): 11182–11187, 1987.

Schulz et al., "Why Were Just These Amino Acids Selected"? *Principles of Protein Structure*, various pages.

Creighton, Thomas E., "Proteins: Structures and Molecular Principles", W. H. Freeman and Co., New York, N.Y., 1983, pp. 37–129, 235, 259, 357–359.

Shively et al., "Microsequence Analysis of Peptides and Proteins", *Analytical Biochemistry*, 120: 312–322, 1982.

Gluzman, Yakov, "Mammalian Cell Transformation with SV40 Hybrid Plasmid Vectors", *Eukaryotic Viral Vectors*, 41–45, 1982.

Marklund et al., "Extracellular Superoxide Dismutase in Human Tissues and Human Cell Lines", *J. Clin. Invest.*, 74: 1398–1403, 1984.

Marklund, Stefan L., "Human Copper-containing superoxide dismutase of high molecular weight", *Proc. Natl. Acad. Sci. USA*, 79: 7634–7638, 1982.

Marklund et al., "Superoxide dismutase in extracellular fluids", *Clinica Chimica Acta*, 126: 41–51, 1982.

Marklund Stefan L., "Extracellular superoxide dismutase and other superoxide dismutase isoenzymes in tissues from nine mammalian species", *Biochem. J.*, 222: 649–655, 1984.

Marklund, Stefan L., "Properties of extracellular superoxide dismutase from human lung", *Biochem. J.*, 220: 269–270, 1984.

Adachi et al., "Interactions between Human Extracellular Superoxide Dismutase C and Sulfated Polysaccharides", *The Journal of Biological Chemistry*, 264(15): 8537–8541, 1989.

Cardin et al., "Molecular Modeling of Protein–Glycosaminoglycan Interactions", *Arteriosclerosis*, 9(1): 21–32, 1989.

Smith et al., "A Heparin Binding Site in Antithrombin III", *The Journal of Biological Chemistry*, 262(23): 11964–11972, 1967.

Hallewell et al., "Human Cu/Zn superoxide dismutase cDNA: isolation of clones synthesising high levels of active or inactive enzyme from an expression library", *Nucleic Acids Research*, 13(6): 2017–2034, 1985.

Matteucci et al., "Targeted random mutagenesis: the use of ambiguously synthesized oligonucleotides to mutagenize sequences immediately 5' of an ATG condon", *Nucleic Acids Research*, 11(10): 3113–3121, 1983.

Sieffens et al., "The Primary Structure of Cu-Zn Superoxide Dismutase from *Photobacterium leiognathi*", Evidence for a Separate Evolution of Cu-Zn Superoxide Dismutase in Bacteria, *Physiol. Chem.*, pp. 675–690, Jun. 1983.

Marklund, Stefan, "Mammalian Superoxide Dismutase", *Chemical Abstracts*, 101:36464x (1984).

"Superoxide dismutase production using monoclonal antibodies", *Chemical Abstracts*, 103:176901d, 1985.

Mamoru Sugiura, "Preparation of Human Placenta Superoxide-Dismutase", 56–102787 (1981).

Midori Juji K.K. "Preparation of Superoxide Dismutase Derived from Human Placenta", vol. 6, No. 2660142 (1982).

L. Tibell et al., "Expression of human extracellular superoxide dismutase in Chinese hamster ovary cells and characterization of the product,", *Proc. Natl. Acad. Sci. USA*, 84:6634–6638, (Oct. 1987).

K. Karlsson et al., "Heparin-induced release of extracellular superoxide dismutase to human blood plasma," *Biochem. J.*, 242: 55–59 (1987).

K. Karlsson et al., "Binding of human extracellular superoxide dismutase C to sulphated glycosaminoglycans," *Biochem. J.*, 256: 29–33 (1988).

K. Karlsson et al., "Plasma Clearance of Human Extracellular–Superoxide Dismutase C in Rabbits," *J. Clin. Invest.*, 82: 762–766 (Sep. 1988).

K. Karlsson et al., "Extracellular superoxide dismutase in the vascular system of mammals," *Biochem. J.*, 255:223–228 (1988).

K. Karlsson et al., "Binding of Human Extracellular–Superoxide Dismutase C to Cultured Cell Lines and to Blood Cells," *Laboratory Investigation*, vol. 60, No. 5, pp. 659–666 (1989).

K. Karlsson et al., "Extracellular-superoxide dismutase; Association with glycosaminoglycans," Umea Univer- (List continued on next page.)

OTHER PUBLICATIONS sity Medical Dissertations, Umea, Sweden, Series 227 (1988).

K. Karlsson et al., "Heparin-, dextran sulfate-and protamine-induced release of extracellular-superoxide dismutase to plasma in pigs," *Biochimica et Biophysica Acta*, 967:110–114 (1988).

B. Beaman et al., "Role of Superoxide Dismutase and Catalase as Determinants of Pathogenicity of *Nocardia asteroides*: Importance in Resistance to Microbicidal Activities of Human Polymorphonuclear Neutrophils," *Infection and Immunity*, vol. 47, No. 1, pp. 135–141 (Jan. 1985).

M. Johansson et al., "Recombinant human extracellular superoxide dismutase reduces concentration of oxygen free radicals in the reperfused rat heart," *Cardiovascular Resarch*, 24:500–503 (1990).

G. Wahlund et al., "Extracellular-superoxide dismutase type C(EC-SOD C) reduces myocardial damage in rats subjected to coronary occlusion and 24 hours of reperfusion," *Free Rad. Res. Comms.*, vol. 0, No. 0, pp. 1–7, (1992).

M. Erlansson et al, "Superoxide dismutase as an inhibitor of postischemic microvascular permeability increase in the hamster," *Free Radical Biology & Medicine*, 9:59–65, (1990).

P. Sjöquist et al., "Cardioprotective Effects of Recombinant Human Extracellular-Superoxide Dismutase Type C in Rat Isolated Heart Subjected to Ischemia and Reperfusion," *J. of Cardiovascular Pharmacol.*, 17:678–683 (1991).

S. Marklund, "Spectrophotometric Study of Spontaneous Disproportionation of Superoxide Anion Radical and Sensitive Direct Assay for Superoxide Dismutase," *J. of Biological Chem.*, vol. 251, No. 23, pp. 7504–7507, Dec. 10, 1976.

S. Marklund, "Direct Assay with Potassium Superoxide," *CRC Handbook of Methods for Oxygen Radical Research*, ed. R. Greenwald, CRC Press, 249–255 (1985).

J. McCord et al., "Superoxide Dismutase," *J. of Biol. Chem.*, vol. 244, No. 22, pp. 6049–6055 (Nov. 25, 1969).

J. Taylor et al., "The use of phosphorothioate-modified DNA in restriction enzyme reactions to prepare nicked DNA," *Nucleic Acids Research*, vol. 13, No. 24, pp. 8749–8764 (1985).

J. Taylor et al., "The rapid generation of oligonucleotide-directed mutations at high frequency using phosphorothioate-modified DNA," *Nucleic Acids Research*, vol. 13, No. 24, pp. 8765–8785 (1985).

K. Nakamaye et al., "Inhibition of restriction endonuclease Nci I cleavage by phosphorothioate groups and its application to oligonucleotide-directed mutagenesis," *Nucleic Acids Research*, vol. 14, No. 24, pp. 9679–9698 (1986).

J. Messing et al., "A new pair of M13 vectors for selecting either DNA strand of double-digest restriction fragments," *Gene* 19: 269–276 (1982).

P. Schreier et al., "A Fast and Simple Method for Sequencing DNA Cloned in the Single-stranded Bacteriophage M13," *J. Mol. Biol.*, 129:169–172 (1979).

M. Ausobel, *Current Protocols in Molecular Biology 1*, Unit 1.15 (1987).

O. Karlsson et al., "A Mutational analysis of the insulin gene transcription control region: Expression in beta cells is dependent on two related sequences within the enhancer," *Proc. Natl. Acad. Sci. USA*, 84:8819–8823 (Dec. 1987).

G. Urlaub et al., "Isolation of Chinese hamster cell mutants deficient in dihydrofolate reductase activity," *Proc. Natl. Acad. Sci. USA*, vol. 77, No. 7, pp. 4126–4220 (Jul. 1980).

Fig. 1A

```
   +1                                          10
   TrpThrGlyGluAspSerAlaGluProAsnSerAspSerAlaGluTrpIleArgAsp
   TGGACGGGCGAGGACTCGGCGGAGCCCAACTCTGACTCGGCGGAGTGGATCCGAGAC
                                                          180

20
 MetTyrAlaLysValThrGluIleTrpGlnGluValMetGlnArgArgAspAspAspGly
 ATGTACGCCAAGGTCACGGAGATCTGGCAGGAGGTCATGCAGCGGCGGGACGACGACGGC
                                                          240
    40                          50
 ThrLeuHisAlaAlaCysGlnValGlnProSerAlaThrLeuAspAlaAlaGlnProArg
 ACGCTCCACGCCGCCTGCCAGGTGCAGCCGTCGGCCACGCTGGACGCCGCGCAGCCCCGG
                                                          300
    60                  70
 ValThrGlyValValLeuPheArgGlnLeuAlaProArgAlaLysLeuAspAlaPhePhe
 GTGACCGGCGTCGTCCTCTTCCGGCAGCTTGCGCCCCGCGCCAAGCTCGACGCCTTCTTC
                                                          360
    80                          90
 AlaLeuGluGlyPheProThrGluProAsnSerSerSerArgAlaIleHisValHisGln
 GCCCTGGAGGGCTTCCCGACCGAGCCGAACAGCTCCAGCCGCGCCATCCACGTGCACCAG
                                                          400
   100                         110
 PheGlyAspLeuSerGlnGlyCysGluSerThrGlyProHisTyrAsnProLeuAlaVal
 TTCGGGGACCTGAGCCAGGGCTGCGAGTCCACCGGGCCCCACTACAACCCGCTGGCCGTG
                                                          480
   120                         130
 ProHisProGlnHisProGlyAspPheGlyAsnPheAlaValArgAspGlySerLeuTrp
 CCGCACCCGCAGCACCCGGGCGACTTCGGCAACTTCGCGGTCCGCGACGGCAGCCTCTGG
                                                          540
   140                         150
 ArgTyrArgAlaGlyLeuAlaAlaSerLeuAlaGlyProHisSerIleValGlyArgAla
 AGGTACCGCGCCGGCCTGGCCGCCTCGCTCGCGGGCCCGCACTCCATCGTGGGCCGGGCC
                                                          600
   160                         170
 ValValValHisAlaGlyGluAspAspLeuGlyArgGlyGlyAsnGlnAlaSerValGlu
 GTGGTCGTCCACGCTGGCGAGGACGACCTGGGCCGCGGCGGCAACCAGGCCAGCGTGGAG
                                                          660
   180                         190
 AsnGlyAsnAlaGlyArgArgLeuAlaCysCysValValGlyValCysGlyProGlyLeu
 AACGGGAACGCGGGCCGGCGGCTGGCCTGCTGCGTGGTGGGCGTGTGCGGGCCCGGGCTC
                                                          720
                          T209        T213 T215 T216
                           ***         ***  ***  ***
   200
 TrpGluArgGlnAlaArgGluHisSerGluArgLysLysArgArgArgGlu SerGluCys
 TGGGAGCGCCAGGCGCGGGAGCACTCAGAGCGCAAGAAGCGGCGGCGCGAG AGCGAGTGC
                           TGA         TGA  TAG  TGA  780

220
 LysAlaAla***
 AAGGCCGCCTGA
```

Fig. 1B

```
   +1                                  10
  TrpThrGlyGluAspSerAlaGluProAsnSerAspSerAlaGluTrpIleArgAsp
  TGGACGGGCGAGGACTCGGCGGAGCCCAACTCTGACTCGGCGGAGTGGATCCGAGAC
                                                          180

20
  MetTyrAlaLysValThrGluIleTrpGlnGluValMetGlnArgArgAspAspAspGly
  ATGTACGCCAAGGTCACGGAGATCTGGCAGGAGGTCATGCAGCGGCGGGACGACGACGGC
                                                          240
   40                                  50
  ThrLeuHisAlaAlaCysGlnValGlnProSerAlaThrLeuAspAlaAlaGlnProArg
  ACGCTCCACGCCGCCTGCCAGGTGCAGCCGTCGGCCACGCTGGACGCCGCGCAGCCCCGG
                                                          300
   60                                  70
  ValThrGlyValValLeuPheArgGlnLeuAlaProArgAlaLysLeuAspAlaPhePhe
  GTGACCGGCGTCGTCCTCTTCCGGCAGCTTGCGCCCCGCGCCAAGCTCGACGCCTTCTTC
                                                          360
                           G1
   80                      Gln 90
  AlaLeuGluGlyPheProThrGluProAsnSerSerSerArgAlaIleHisValHisGln
  GCCCTGGAGGGCTTCCCCGACCGAGCCGAACAGCTCCAGCCGCGCCATCCACGTGCACCAG
                           CAA                            400
   100                                 110
  PheGlyAspLeuSerGlnGlyCysGluSerThrGlyProHisTyrAsnProLeuAlaVal
  TTCGGGGACCTGAGCCAGGGCTGCGAGTCCACCGGGCCCCACTACAACCCGCTGGCCGTG
                                                          480
   120                                 130
  ProHisProGlnHisProGlyAspPheGlyAsnPheAlaValArgAspGlySerLeuTrp
  CCGCACCCGCAGCACCCGGGCGACTTCGGCAACTTCGCGGTCCGCGACGGCAGCCTCTGG
                                                          540
   140                    . 150
  ArgTyrArgAlaGlyLeuAlaAlaSerLeuAlaGlyProHisSerIleValGlyArgAla
  AGGTACCGCGCCGGCCTGGCCGCCTCGCTCGCGGGCCCGCACTCCATCGTGGGCCGGGCC
                                                          600
   160                                 170
  ValValValHisAlaGlyGluAspAspLeuGlyArgGlyGlyAsnGlnAlaSerValGlu
  GTGGTCGTCCACGCTGGCGAGGACGACCTGGGCCGCGGCGGCAACCAGGCCAGCGTGGAG
                                                          660
   180                                 190
  AsnGlyAsnAlaGlyArgArgLeuAlaCysCysValValGlyValCysGlyProGlyLeu
  AACGGGAACGCGGGCCGGCGGCTGGCCTGCTGCGTGGTGGGCGTGTGCGGGCCCGGGCTC
                                                          720
                                         SA216    SA219
   200                    210            Ala      Ala
  TrpGluArgGlnAlaArgGluHisSerGluArgLysLysArgArgArgGluSerGluCys
  TGGGAGCGCCAGGCGCGGGAGCACTCAGAGCGCAAGAAGCGGCGGCGCGAGAGCGAGTGC
                                         GCG      GCC
SA220
Ala
 LysAlaAla***
 AAGGCCGCCTGA
 GCG
```

Fig. 1C

```
    +1                                   10
  TrpThrGlyGluAspSerAlaGluProAsnSerAspSerAlaGluTrpIleArgAsp
  TGGACGGGCGAGGACTCGGCGGAGCCCAACTCTGACTCGGCGGAGTGGATCCGAGAC
                                                          180

20
  MetTyrAlaLysValThrGluIleTrpGlnGluValMetGlnArgArgAspAspAspGly
  ATGTACGCCAAGGTCACGGAGATCTGGCAGGAGGTCATGCAGCGGCGGGACGACGACGGC
                                                          240
    40                          50
  ThrLeuHisAlaAlaCysGlnValGlnProSerAlaThrLeuAspAlaAlaGlnProArg
  ACGCTCCACGCCGCCTGCCAGGTGCAGCCGTCGGCCACGCTGGACGCCGCGCAGCCCCGG
                                                          300
    60                              70
  ValThrGlyValValLeuPheArgGlnLeuAlaProArgAlaLysLeuAspAlaPhePhe
  GTGACCGGCGTCGTCCTCTTCCGGCAGCTTGCGCCCCGCGCCAAGCTCGACGCCTTCTTC
                                                          360
                               G1
    80                         Gln 90
  AlaLeuGluGlyPheProThrGluProAsnSerSerSerArgAlaIleHisValHisGln
  GCCCTGGAGGGCTTCCCCGACCGAGCCGAACAGCTCCAGCCGCGCCATCCACGTGCACCAG
                               CAA                       400
    100                              110
  PheGlyAspLeuSerGlnGlyCysGluSerThrGlyProHisTyrAsnProLeuAlaVal
  TTCGGGGACCTGAGCCAGGGCTGCGAGTCCACCGGGCCCCACTACAACCCGCTGGCCGTG
                                                          480
    120                              130
  ProHisProGlnHisProGlyAspPheGlyAsnPheAlaValArgAspGlySerLeuTrp
  CCGCACCCGCAGCACCCGGGCGACTTCGGCAACTTCGCGGTCCGCGACGGCAGCCTCTGG
                                                          540
    140                              150
  ArgTyrArgAlaGlyLeuAlaAlaSerLeuAlaGlyProHisSerIleValGlyArgAla
  AGGTACCGCGCCGGCCTGGCCGCCTCGCTCGCGGGCCCGCACTCCATCGTGGGCCGGGCC
                                                          600
    160                              170
  ValValValHisAlaGlyGluAspAspLeuGlyArgGlyGlyAsnGlnAlaSerValGlu
  GTGGTCGTCCACGCTGGCGAGGACGACCTGGGCCGCGGCGGCAACCAGGCCAGCGTGGAG
                                                          660
    180                              190
  AsnGlyAsnAlaGlyArgArgLeuAlaCysCysValValGlyValCysGlyProGlyLeu
  AACGGGAACGCGGGCCGGCGGCTGGCCTGCTGCGTGGTGGGCGTGTGCGGGCCCGGGCTC
                                                          720
                                                SAT216
    200                              210        Ala***
  TrpGluArgGlnAlaArgGluHisSerGluArgLysLysArgArgArgGluSerGluCys
  TGGGAGCGCCAGGCGCGGGAGCACTCAGAGCGCAAGAAGCGGCGGCGCGAGAGCGAGTGC
                                                GCGTGA  780

220
  LysAlaAla***
  AAGGCCGCCTGA
```

Fig. 3A

```
              ***
T216     5'-GCGGCGCGAGTGAGAGTGCAAGG-3'
            ||||||||||| |||||||||||
Template 3'-CGCCGCGCTCTCGCTCACGTTCC
            |                     |
            762                   784

***
T215     5'-GCGGCGGCGCTAGAGCGAGTG-3'
            |||||||||| ||||||||||
Template 3'-CGCCGCCGCGCTCTCGCTCAC-5'
            |                   |
            759                 779

***
T213     5'-CAAGAAGCGGTGACGCGAGAGCG-3'
            ||||||||| |||||||||||
Template 3'-GTTCTTCGCCGCCGCGCTCTCGC-5'
            |                     |
            753                   775

***
T209     5'-GCACTCAGAGTGAAAGAAGCGGC-3'
            ||||||||| |||||||||||
Template 3'-CGTGAGTCTCGCGTTCTTCGCCG-5'
            |                     |
            741                   763
```

Fig. 3B

```
              ***
SA216    5'-CGGCGGCGCGCGAGCGAGTGC-3'
            ||||||||||  ||||||||||
Template 3'-GCCGCCGCGCTCTCGCTCACG-5'
            |                   |
           760                 780

***
SA219    5'-CGAGAGCGAGGCCAAGGCCGCCT-3'
            ||||||||||  ||||||||||
Template 3'-GCTCTCGCTCACGTTCCGGCGGA-5'
            |                    |
           768                  790

***
SA220    5'-GAGCGAGTGCGCGGCCGCCTGA-3'
            ||||||||||  ||||||||||
Template 3'-CTCGCTCACGTTCCGGCGGACT-5'
            |                    |
           771                  792

******
SAT216   5'-CGGCGGCGCGCGTGAGAGTGC-3'
            ||||||||| | | ||||||
Template 3'-GCCGCCGCGCTCTCGCTCACG-5'
            |                   |
           760                 780
              ***

G1       5'-GACCGAGCCGCAAAGCTCCAGCC-3'
            |||||||||| | ||||||||||
Template 3'-CTGGCTCGGCTTGTCGAGGTCGG-5'
            |                    |
           378                  400
```

NON-GLYCOSYLATED VARIANTS OF EXTRACELLULAR SUPEROXIDE DISMUTASE (EC-SOD)

The present invention relates to a polypeptide having the superoxide dismutating property of native extracellular superoxide dismutase and a modified, i.e. reduced or increased, affinity for heparin compared to extracellular superoxide dismutase of type C, methods of producing the polypeptide and the use thereof for the purpose of therapeutic treatment.

Organisms living in the presence of oxygen have been forced to develop a number of protective mechanisms against toxic oxygen reduction metabolites, such as superoxide radicals, which are formed in connection with a variety of biological oxidations. The protective factors include superoxide dismutases (SOD) (superoxide:superoxide oxidoreductase, EC 1.15.1.1) which dismutate the superoxide radical and are found in relatively constant amounts in mammalian cells and tissue. The best known of these enzymes is CuZn SOD which is a dimer with a molecular weight of 33,000 containing two copper and two zinc atoms. CuZn SOD is found in the cytosol and in the intermembrane space of the mitochondria. Mn SOD is a tetramer with a molecular weight of 85,000 containing 4 Mn atoms, and is mainly located in the mitochondrial matrix. Recently, a superoxide dismutase was found in the extracellular fluids of mammals, birds and fish. This superoxide dismutase has been denoted extracellular superoxide dismutase which in the following will be termed EC-SOD.

EC-SOD is a tetrameric Cu and Zn containing glycoprotein (S. L. Marklund, Proc. Natl. Acad. Sci. USA. 79, 1982, pp. 7634–7638; L. Tibell et al., Proc. Natl. Acad. Sci. USA. 84, 1987, pp. 6634–6638). A cDNA sequence encoding EC-SOD has been elucidated and useful applications of the cDNA and the EC-SOD encoded thereby are described in WO 87/01387, the contents of which are hereby incorporated by reference. The cDNA sequence is the sequence shown in FIG. 1A and FIG. 1B corresponding to amino acid residues 1–222 (without any mutations). EC-SOD is a secretory protein and the cDNA encodes an 18 amino acids long signal sequence which is absent in mature and recombinant EC-SOD (L. Tibell et al., Proc. Natl. Acad. Sci. USA. 84, 1987, pp. 6634–6638). As deduced from the cDNA sequence, the subunit molecular weight of the mature enzyme is 24,200. The exact size of the carbohydrate substituent is not known, but the apparent molecular weight on gel chromatography of the tetramer is 140–150 kDa. On SDS-PAGE electrophoresis the subunits display a molecular weight of 30–32 kDa (L. Tibell et al., Proc. Natl. Acad. Sci. USA. 84, 1987, pp. 6634–6638). The sequence contains one glycosylation site Asn-89 (K. Hjalmarsson et al., Proc. Natl. Acad. Sci. USA. 84, 1987, pp. 6340–6344), and the mature enzyme binds to the lectins concanavalin A, wheat germ lectin and lentil lectin. The tetramers contain 4 Cu and 4 Zn atoms. The active site, which contains the metal atoms, is homologous to the active site of the intracellular CuZn SODs (K. Hjalmarsson et al., Proc. Natl. Acad. Sci. USA. 84, 1987, pp. 6340–6344).

EC-SOD isolated from tissues and plasma is heterologous with regard to heparin affinity, and can upon chromatography on Heparin-Sepharose be divided into three subclasses;

A which does not bind,

B with intermediate affinity and

C with relatively strong heparin affinity.

in vivo the correlate of the heparin affinity is binding to heparan sulfate proteoglycan (K. Karlsson and S. L. Marklund, Biochem. J. 242, 1987, pp. 55–59 , K. Karlsson et al., Biochem. J. 256, 1988, pp. 29–33; S. L. Marklund and K. Karlsson, Lab. Invest.in press, 1989), which occurs on cell surfaces and in the interstitial connective tissue.

In the vasculature, EC-SOD of subclass C, which in the following is termed EC-SOD C, exists in equilibrium between the plasma phase and heparan sulfate proteoglycan in the glycocalyx of the vessel endothelium (K. Karlsson and S. L. Marklund, Biochem. J. 242, 1987, pp. 55–59; K. Karlsson and S. L. Marklund, J. Clin. Invest. 82, 1988, pp. 762–766; K. Karlsson and S. L. Marklund, Biochem. J. 255, 1988, pp. 223–228). Upon injection of heparin, bound enzyme is released to plasma because it binds to the heparin instead of the heparan sulfate. This effect is seen only for EC-SOD forms which upon chromatography on Heparin-Sepharose under conditions described in the Analytical Methods section below (Analytical separation of EC-SOD variants from cell culture media on Heparin-Sepharose) are released by the NaCl gradient at concentrations above 0.38M (K. Karlsson and S. L. Marklund, Biochem. J. 255, 1988, pp. 223–228). Only such forms bind in vivo to vessel endothelium, and with this property the C-class EC-SODs are defined. B-class EC-SODs (EC-SOD B) show heparin affinity, but are eluted at concentrations below 0.38M NaCl, and A-class EC-SODs (EC-SOD A) do not display heparin affinity under the conditions of the Heparin-Sepharose chromatography. EC-SOD Cs appear to bind to the surface of most cell-types in the body, notable exceptions are erythrocytes and neutrophil leukocytes. Binding to various E. coli strains could not be demonstrated (S. L. Marklund and K. Karlsson, Lab. Invest., Vol. 60, pp 659–666, 1989). This binding pattern suggests that EC-SOD C has the potential to protect most normal cells in the body, without protecting microorganisms lacking affinity and without much interfering with superoxide radicals produced at the surfaces of activated neutrophil leukocytes.

The binding to the strongly negatively charged heparin is apparently of electrostatic nature (K. Karlsson et al., Biochem. J. 256, 1988, pp. 29–33). The carboxy-terminal end of EC-SOD C carries a strong positive charge since among the last 20 amino acids 9 are positively charged. This part of the molecule has been suggested to form the heparin-receptor structure and Adachi and Marklund (J. Biol. Chem. 264, No. 15, pp. 8537–8541, 1989) suggest that lysine and arginine residues of the C-terminal end are involved in the binding of EC-SOD C to sulfated glycosaminoglycans (SGAGs), a class of compounds to which heparin belongs. Thus, Adachi and Marklund have used amino acid specific reagents in modifying the lysine and arginine residues of EC-SOD C and obtained enzymes having a reduced affinity to heparin, which enzymes in some cases have lost their superoxide dismutating activity. Adachi and Marklund did not reveal which lysine and arginine residues of EC-SOD are involved in the heparin binding and did not disclose the modification of other amino acid residues, and as it will be understood from the following discussion, the disclosure of Adachi and Marklund does not form part of the present invention.

It may also be noted that the behaviour upon ion exchange chromatography and isoelectric points of plasma fractions containing EC-SOD A and EC-SOD C has not been established with certainty as being different (Karlsson, K., Umeå University Medical Dissertations, New Series No 227, 1988).

In plasma, EC-SOD A and EC-SOD B seem to be quantitatively important, whereas only minor amounts seem to be present in tissue. Studies up till now indicate that in the native environment, especially in the plasma, the three types of EC-SOD are present. In addition, EC-SOD forms an equilibrium between the plasma and endothelial surfaces.

In the treatment of various diseases or disorders it may be advantageous to be able to control the level of circulating EC-SOD in the plasma and thereby control the degree of plasma and epithelial binding. Use of EC-SODs of various heparin affinities (reduced or increased as compared to EC-SOD C) would be a means of controlling the circulating level of EC-SOD in the plasma.

EC-SOD C is the only type of EC-SOD which it has been possible to obtain in large quantities and in a form which is contemplated to be sufficiently pure for therapeutic application, vide WO 87/01387 in which the production of recombinant EC-SOD C is disclosed. EC-SOD A and EC-SOD B have been observed in plasma and tissue samples in very low amounts and it has not been possible to isolate these EC-SOD types in a therapeutically acceptable pure form and in amounts which would make the use thereof in the treatment of various diseases or disorders realistic.

In order to be able to control the circulating level of EC-SOD in plasma in connection with treatment of diseases or disorders where this is advantageous, it is desirable to provide EC-SOD types having various affinities for heparin and thus heparan sulphate present on cell surfaces, without the superoxide dismutating property thereof being impaired.

According to the invention, it has been found that the affinity, to heparin, of polypeptides showing the superoxide dismutating property of EC-SOD may be modified by suitable modification of the C-terminal amino acid sequence of such polypeptides. A decreased affinity to heparin is obtained when the C-terminal amino acid sequence is truncated, and/or when the C-terminal amino acid sequence is conferred with a smaller positive net charge than the net charge of the amino acid sequence constituting amino acid moieties 194–222 of recombinant EC-SOD C.

Thus, in one aspect, the invention relates to a polypeptide having the superoxide dismutating property of the native extracellular superoxide dismutase (EC-SOD) and having a modified binding to heparin as compared with recombinant EC-SOD C, the polypeptide having the formula

A-R wherein A designates the EC-SOD C amino acid sequence from and including amino acid moiety No. 1 up to and including amino acid moiety No. 193 (vide FIG. 1A or FIG. 1B) and R is an amino acid sequence conferring to the polypeptide either a reduced affinity for heparin compared to recombinant EC-SOD C as a result of the sequence being truncated from its C-terminal end compared to the amino acid sequence constituting amino acid moieties 194–222 of recombinant EC-SOD C, and/or having a smaller positive net charge than the net charge of the amino acid sequence constituting amino acid moieties 194–222 of recombinant EC-SOD C, or an increased affinity for heparin compared to recombinant EC-SOD C as a result of the sequence having a larger positive net charge than the net charge of the amino acid sequence constituting amino acid moieties 194–222 of recombinant EC-SOD C, the glycosylation site of the polypeptide in the above cases optionally being replaced by a moiety which cannot be glycosylated, or R is the amino acid sequence constituting amino acid moieties 194–222 of recombinant EC-SOD C, in which case the glycosylation site of the polypeptide has been replaced with a moiety which cannot be glycosylated, whereby the heparin affinity of the polypeptide has been increased, compared to recombinant EC-SOD C, and modifications thereof which retain the superoxide dismutating property of native EC-SOD.

In the present context, the term "a reduced affinity to heparin" indicates that the polypeptide either has no substantial binding to heparin under physiological conditions or has a binding to heparin which is less strong than the binding of recombinant EC-SOD C, the binding being assessed in vitro by elution with NaCl as described in the Analytical Method section given below. Thus, the heparin affinity is determined by means of the concentration of NaCl required for eluting the polypeptide when bound to heparin. Correspondingly, the term "an increased affinity to heparin" indicates that the polypeptide has a binding to heparin which is stronger than the binding of recombinant EC-SOD C, the binding again being assessed in vitro by elution with NaCl.

As appears from the explanation given below, the heparin affinity of the polypeptide is of major importance to the utility of the polypeptide in connection with various therapeutic, surgical or prophylactic treatments, and the present invention now makes it possible to provide, in a scale useful for practical use, a range of useful novel polypeptides with the superoxide dismutating property of native EC-SOD, but with modified heparin affinity.

The term "net charge" indicates the sum of the charges of the amino acid sequence. It is well known that some amino acids, like Arg and Lys, and under certain pH, His, are positively charged, while other amino acids, like Asp and Glu are negatively charged and further amino acids such as glutamine, cysteine, serine, methionine, asparagine, alanine, valine, glycine, leucine, isoleucine, proline, threonine, phenylalanine, tyrosine, and tryptophan are neutral or uncharged. To assess the positive net charge of an amino acid sequence, one counts the number of positive charges on amino acids of the sequence and, from the resulting number, subtracts the number of negative charges. A negative net charge is assessed analogously. The net charge is not to be confused with the charge density, which is calculated by dividing the net charge by the number of amino acids in the sequence.

In the present context, "the superoxide dismutating property of native EC-SOD" refers to the capability of the polypeptide (of course, with the appropriate metal association) to catalyze a first-order dismutation of the superoxide radical in a manner corresponding to EC-SOD. EC-SOD and other superoxide dismutases (SODs) catalyze the following reaction $$O_2{\cdot}^- + O_2{\cdot}^- + 2H^+ \rightarrow O_2 + H_2O_2$$

The specific activity of the SODs is very high and is probably mediated by the four Cu atoms of SOD. The rate constant for the catalyzed reaction is about $1 \times 10^9$ $M^{-1}s^{-1}$ per Cu atom of the SOD. Because of the superoxide dismutating property of the polypeptide of the invention, the polypeptide is also, in the present context, referred to as a polypeptide which confers or mediates EC-SOD activity. Thus, in the present context the term "EC-SOD activity" is used to indicate the enzymatic or superoxide dismutating activity conferred by the polypeptide of the invention. It should be noted that the term "superoxide dismutating property of native EC-SOD" and related terms should be understood to be qualitative rather than quantitative, that is, relating to the nature rather than the level of activity of the polypeptide. The superoxide dismutating property of a given polypeptide may be evaluated by the method set forth in the Analytical Method section below under the heading: "Analysis of superoxide dismutase activity". Thus, it will be understood from the above explanation that "the superoxide dismutating property of native EC-SOD" could also simply be termed "SOD activity" or "SOD enzymatic activity". The term "native" as used in connection with EC-SOD refers to the naturally occurring EC-SOD which is found in body tissue or fluid and which may be any of the naturally occurring EC-SOD types. Native EC-SOD may e.g. be obtained by extraction from mammalian tissues, e.g. as explained in WO 87/01387.

The term "modifications" is intended to cover proteins or polypeptides which have substantially the characteristics of the polypeptide of the invention outlined above, i.e. the superoxide dismutating property of EC-SOD and a modified affinity for heparin as compared with recombinant EC-SOD C, but which may, with respect to some amino acid moieties, be of a composition different from the composition of the polypeptide of the formula set forth above. Thus, the amino acid sequence of any part of the polypeptide sequence outlined above may be modified by amino acid substitution, insertion, deletion, or addition as long as the critical property, i.e. the superoxide dismutating property, of the polypeptide is not impaired. The modification may be introduced in the polypeptide moiety R or the polypeptide moiety corresponding to the part of the EC-SOD amino acid sequence constituting amino acids 1-193. Furthermore, any modification of the amino acids constituting the polypeptide outlined above, i.e. glycosylation, acetylation, and other possible modifications which do not impair the superoxide dismutating property of the native EC-SOD is within the scope of the present invention. Also a subsequence of the polypeptide outlined above as well as a polypeptide being constituted of 2 or more subsequences should be understood to be within the definition of a modification of the polypeptide which is within the present invention. The substitution, deletion, insertion and/or addition of amino acid moieties in the polypeptide shown above producing modifications thereof may be obtained in accordance with well known techniques, such as site-directed mutagenesis. This will be discussed in further detail below.

The formula A-R outlined above of the polypeptide of the invention is constituted of two parts; the first part is the amino acid sequence of EC-SOD C from and including amino acid 1 and up to and including amino acid 193. The entire EC-SOD sequence is constituted of 222 amino acids, not all of which are required for conferring the superoxide dismutating property to native EC-SOD C. Thus, by comparison of the amino acid sequence with Cu Zn SODs of various origins, a possible active site of the enzyme has been found between amino acid 97 and amino acid 193 of the amino acid sequence encoding EC-SOD C. This part of EC-SOD C is believed to be essential for the superoxide dismutating property of the enzyme. The part of the EC-SOD C constituting amino acid 1-96 is contemplated to be involved in the formation of oligomers of the polypeptide. However, in accordance with what is stated above, modifications within the part of the EC-SOD C sequence constituting amino acids 1-193, which modifications do not impair the superoxide dismutating property of the enzyme should be considered as modifications of the polypeptide of the invention in accordance with the definition given above. Based on the above-mentioned homology between the active sites of the various SOD enzymes, modifications in the part of the EC-SOD C sequence constituting amino acids 1-193 could be performed by site-directed mutagenesis so that the active site of the enzyme remains active. How to perform such modifications is explained in further details below. The amino acid sequence R of the polypeptide of the invention is the part of the polypeptide which has been found, according to the invention, to be relevant with respect to modifications of the heparin affinity of the enzyme. Normally, R is based on the amino acids moieties 194-222 of recombinant EC-SOD C, i.e. the amino acid moieties of the C-terminal part of EC-SOD C, R, however, having been changed in accordance with the present invention in such a manner that a reduced or an increased affinity for heparin has been obtained compared to the heparin affinity of recombinant EC-SOD C. The changes of the C-terminal part of EC-SOD C which produce the amino acid sequence R will be further dealt with in the following. In adddition to such changes, R may in some cases have been subjected to modifications as defined above, e.g. modifications in R which are not involved in the heparin binding.

Because of the high degree of homology between the polypeptide of the invention and EC-SOD, the polypeptide of the invention is also referred to as a EC-SOD variant.

The modified affinity for heparin of the polypeptide of the invention as compared with the binding to heparin of recombinant EC-SOD C may be either a reduced or an increased affinity. An increased affinity may be advantageous when it is desirable to provide a strong binding of the polypeptide to cell surfaces, e.g. in connection with transplantation of organs or when the EC-SOD activity is injected directly into an inflamed organ where it is to bind. A reduced affinity for heparin may be advantageous when it is desirable to provide a high amount of EC-SOD activity circulating in the body fluid so as to ensure that freely circulating EC-SOD variant is available for sufficient time after injection to move to the tissue or cell where it is needed without immediately being bound to vascular cell surfaces when brought in contact therewith.

The term "the glycosylation site" means the Asn moiety of position 89 of the polypeptide and—where appropriate—any other moiety of the polypeptide which can be glycosylated. (In the unmodified polypeptide, the Asn moiety of position 89 is the only moiety which can be glycosylated).

It has surprisingly been found (vide Example 4) that substituting the glycosylation site of EC-SOD C with a non-glycosylation site results in a polypeptide having increased affinity for heparin compared to recombinant EC-SOD C. It is surprising that a glycosylation-free polypeptide has a marked increased heparin affinity compared to recombinant EC-SOD C because the glycosylation site of EC-SOD C, the sequence of which appears from FIG. 1A and 1B, is found at position 89 of the sequence, i.e. in the N-terminal part of the polypeptide which would not be believed to be of importance for heparin binding. A glycosylation-free polypeptide has the advantage that it may be produced in an organism which is not capable of carrying out glycosylation. Thus, e.g., a glycosylation-free polypeptide may be produced in E. coli which is a well known and widely used host organism for the production of recombinant polypeptides. The production in E. coli is normally very simple and does not require that any extensive measures are taken as opposed to the use of various cell lines as host organisms in the recombinant production of polypeptides, which cell lines should be handled more carefully. The expenses of recombinant production in E. coli are lower than the expenses of the recombinant production in cell lines derived from higher organisms.

Preferably, the smaller positive net charge of R compared to the net charge of the amino acid sequence constituting amino acid moieties 194–222 of recombinant EC-SOD C has been obtained by removal of one or several positively charged amino acid moieties compared to the amino acid sequence constituting amino acid moieties 194–222 of recombinant EC-SOD C and/or substitution of one or several positively charged amino acid moieties of the amino acid sequence constituting amino acid moieties 194–222 of recombinant EC-SOD C with negatively charged and/or neutral amino acid moieties, and/or addition of negatively charged amino acid moieties, compared to the corresponding sequence in EC-SOD C, and/or chemical modification of one or more amino acid moieties to introduce negative charges.

The methods by which these various modifications of the amino acid sequence are carried out is described in further detail below.

In one embodiment, R designates a truncated version of the amino acid sequence constituting amino acid moieties 194–222 of recombinant EC-SOD C, the C-terminal end of the sequence having been truncated with 1–12 amino acids. The truncation may be accomplished by use of site-directed mutagenesis as described below. As it is described in the examples, truncation of different numbers of amino acids results in polypeptides having different affinities for heparin. Thus, truncation of 6 amino acids results in a polypeptide having a slightly reduced affinity for heparin (variant T216 described above), whereas truncation of 7 amino acids surprisingly results in a polypeptide having substantially no affinity for heparin (variant T215), i.e. a polypeptide of EC-SOD A type. Thus, the presence of an amino acid in position 216 seems to be important for conferring to the polypeptide an affinity for heparin; the presence of a cluster of positively charged amino acids (amino acids 210–214) is surprisingly not in itself sufficient for ensuring binding to heparin. Thus, when a reduced but not totally lacking heparin affinity is desirable, it is preferred that the amino acid sequence R comprises at least 23 amino acid moieties.

In variant T216, position 216 is occupied by the negatively charged glutamine, but other experiments (vide Example 4) have indicated that the charge of the amino acid in this position is of minor importance to the heparin affinity of the polypeptide. Thus, in addition to net charge, the structure of the polypeptide is contemplated to be important for binding to heparin. Accordingly, in a preferred embodiment, the C-terminal end has been truncated with 1–6 amino acids, such as with 1–5 amino acids, which in most cases will ensure some binding to heparin as will be explained in further detail below.

In another preferred embodiment, the larger positive net charge of R compared to the net charge of the amino acid sequence constituting amino acid moieties 194–222 of recombinant EC-SOD C has been obtained by removal of negatively charged amino acid moieties compared to the amino acid sequence constituting amino acid moieties 194–222 of recombinant EC-SOD C, and/or substitution of neutral and/or negatively charged amino acid moieties with positively charged amino acid moieties, compared to the amino acid sequence constituting amino acid moieties 194–222 of recombinant EC-SOD C, and/or addition of positively charged amino acid moieties, compared to the amino acid sequence constituting amino acid moieties 194–222 of recombinant EC-SOD C, and/or chemical modification of one or more amino acid moieties to introduce positive charges, which produces a polypeptide having an increased affinity for heparin.

Preferably, the amino acid sequence of the polypeptide of the invention contains one or several of the following amino acid moieties: Arg, Lys, Glu, Ser, Cys, and His. The presence of these amino acid moieties in R will normally give rise to a modified affinity for heparin compared to recombinant EC-SOD C.

One example of a polypeptide of the invention is the polypeptide T216 referred to above, which polypeptide has a reduced binding to heparin as compared with recombinant EC-SOD C. The amino acid sequence R in the polypeptide T216 is Val-Cys-Gly-Pro-Gly-Leu-Trp-Glu-Arg-Gln-Ala-Arg-Glu-His-Ser-Glu-Arg-Lys-Lys-Arg-Arg-Arg-Glu. The polypeptide T216 has a slightly reduced affinity for heparin compared to EC-SOD C and has been shown to have the superoxide dismutating property of native EC-SOD. The polypeptide T216 is further described in Example 1, 2 and 4 below.

Another example of a polypeptide of the invention is the polypeptide termed T215 which has a reduced binding to heparin as compared with recombinant EC-SOD C. In the polypeptide T215, R is Val-Cys-Gly-Pro-Gly-Leu-Trp-Glu-Arg-Gln-Ala-Arg-Glu-His-Ser-Glu-Arg-Lys-Lys-Arg-Arg-Arg. The polypeptide T215 is further described in Examples 1, 2 and 4 below.

Still another example of a polypeptide of the invention is the polypeptide termed T213 which has a reduced binding to heparin as compared with recombinant EC-SOD C. In the polypeptide T213, R is Val-Cys-Gly-Pro-Gly-Leu-Trp-Glu-Arg-Gln-Ala-Arg-Glu-His-Ser-Glu-Arg-Lys-Lys-Arg. The polypeptide T213 is further described in Examples 1, 2 and 4 below.

A further example of a polypeptide of the invention is the polypeptide termed T209 which has a reduced binding to heparin as compared with recombinant EC-SOD C. In the polypeptide T209, R is Val-Cys-Gly-Pro-Gly-Leu-Trp-Glu-Arg-Gln-Ala-Arg-Glu-His-Ser-Glu. The polypeptide T209 is further described in Examples 1, 2 and 4 below.

An example of a polypeptide of the invention having an increased binding to heparin as compared with recombinant EC-SOD C and which is non-glycosylated, is the polypeptide G1, wherein the glycosylation site Asn 89 in the polypeptide of native EC-SOD C has been replaced with a Gln-moiety. The polypeptide G1 is further described in Examples 1, 2 and 4 below.

Still another example of a polypeptide of the invention having a reduced binding to heparin as compared with recombinant EC-SOD C is the polypeptide SA220. The amino acid sequence R in the polypeptide SA220 is Val-Cys-Gly-Pro-Gly-Leu-Trp-Glu-Arg-Gln-Ala-Arg-Glu-His-Ser-Glu-Arg-Lys-Lys-Arg-Arg-Arg-Glu-Ser-Glu-Cys-Ala-Ala-Ala wherein the amino acid Lys 220 of the native EC-SOD C has been replaced with an Ala moiety. The polypeptide SA220 is further described in Examples 1, 2 and 4 below.

An example of a polypeptide of the invention having an increased binding to heparin as compared with recombinant EC-SOD C is the polypeptide SA216. The amino acid sequence R in the polypeptide SA216 is Val-Cys-Gly-Pro-Gly-Leu-Trp-Glu-Arg-Gln-Ala-Arg-Glu-His-Ser-Glu-Arg-Lys-Lys-Arg-Arg-Arg-Ala-Ser-Glu-Cys-Lys-Ala-Ala wherein the amino acid Glu 216 of the native EC-SOD C has been replaced with an Ala moiety. The polypeptide SA216 is further described in Examples 1, 2 and 4 below.

Still another example of a polypeptide of the invention having a reduced binding to heparin as compared with recombinant EC-SOD C is the polypeptide SAT216. The amino acid sequence R in the polypeptide SAT216 is Val-Cys-Gly-Pro-Gly-Leu-Trp-Glu-Arg-Gln-Ala-Arg-Glu-His-Ser-Glu-Arg-Lys-Lys-Arg-Arg-Arg-Ala wherein the amino acid Glu 216 of the native EC-SOD C has been replaced with an Ala moiety and the rest of the C-terminal end has been truncated.

The polypeptide SA219 may be used as a reference example illustrating that the substitution of a neutral amino acid with another neutral amino acid in position 219 results in a polypeptide having the same binding to heparin as recombinant EC-SOD C. Thus, when the net charge remains unchanged, no modification in heparin binding is observed. The amino acid sequence R in the polypeptide SA219 is Val-Cys-Gly-Pro-Gly-Leu-Trp-Glu-Arg-Gln-Ala-Arg-Glu-His-Ser-Glu-Arg-Lys-Lys-Arg-Arg-Arg-Glu-Ser-Glu-Ala-Lys-Ala-Ala wherein the neutral amino acid Cys 219 of the native EC-SOD C has been replaced with another neutral amino acid, namely an Ala moiety. The polypeptide SA219 is further described in Examples 1, 2 and 4 below.

The polypeptide of the invention having the superoxide dismutating property of native EC-SOD and a modified affinity for heparin as compared with recombinant EC-SOD C is preferably of recombinant origin. In the present context, the term "recombinant" is intended to indicate that the polypeptide is derived from a cell which has been subjected to recombinant DNA techniques, i.e. into which a DNA sequence coding for the polypeptide has been inserted and which has subsequently been induced to express the polypeptide. However, as it will be explained below the polypeptide of the invention may also be obtained from EC-SOD which is produced by a cell line, e.g. of human origin, and which subsequent to its production is modified, e.g. chemically or enzymatically, to result in the polypeptide of the invention.

In accordance herewith, a further and important aspect of the present invention is a polypeptide composition which has the superoxide dismutating property of native EC-SOD and which comprises several of the above defined polypeptides of the invention, or one or more of the polypeptides of the invention in admixture with EC-SOD A, EC-SOD B or EC-SOD C.

The polypeptide(s) of the invention from which the polypeptide composition is formed may be one(s) which either has/have a reduced or an increased affinity for heparin compared to recombinant EC-SOD C. The polypeptide(s) of the invention may be the only constituent(s) of the polypeptide composition. This is advantageous because the polypeptides may be produced rather easily by recombinant techniques, e.g. as described below, and may be constructed so as to provide a polypeptide composition having a specific desirable affinity for heparin (which may be different from the affinity defined by types A, and B and C). However, the polypeptide(s) of the invention may also be used in admixture with EC-SOD A, EC-SOD B or EC-SOD C which may either be native or produced in accordance with the principles of the present invention, e.g. as described below. EC-SOD C is easily available in a recombinant form, which also, by means of the present invention applies for EC-SOD A and EC-SOD B. Admixing one or more of the polypeptides of the invention with EC-SOD A, EC-SOD B and/or EC-SOD C may be advantageous in order to confer to the polypeptide composition a specific and desirable affinity for heparin.

Thus, in another aspect, the polypeptide composition which has the superoxide dismutating property of native EC-SOD is an oligomer which comprises several polypeptides of the invention, or one or more of the polypeptides in admixture with EC-SOD A, EC-SOD B or EC-SOD C. The oligomer is presumed to be formed when the polypeptides of the invention or the polypeptide(s) and the EC-SOD A, EC-SOD B or EC-SOD C are contacted with each other, e.g. in a suitable solution similarly to what is believed to happen in vivo where the tetrameric EC-SOD is automatically formed.

Preferably, the polypeptide composition of the invention is in the form of a tetramer comprising four polypeptides as defined above, or one or more of the polypeptides in admixture with EC-SOD A, EC-SOD B or EC-SOD C.

The polypeptides of the polypeptide composition of the invention may either be identical or different.

The polypeptide composition of the invention described above may have a lower mean heparin binding than recombinant EC-SOD C. The term "mean heparin binding" is used because the different polypeptide constituents of the polypeptide composition may have different affinities for heparin and thus be bound to a greater or smaller extent to heparin or heparan sulphate at cell surfaces. However, the mean heparin binding is the overall binding of the composition.

Examples of various polypeptide compositions of the invention are:

- a polypeptide composition which is composed of two polypeptides having reduced affinity for heparin compared to recombinant EC-SOD C, for instance, of the polypeptide termed T216 and the polypeptide T213 described herein, or
- a polypeptide composition which is composed of a polypeptide having reduced heparin affinity compared to recombinant EC-SOD C, e.g. the polypeptide termed T216 described herein, and recombinant EC-SOD C.

The polypeptide or polypeptide composition of the invention may be one which has an increased affinity for heparin compared to recombinant EC-SOD C and which has a (mean where appropriate) heparin binding affinity corresponding to complete elution of the polypeptide or polypeptide composition from a heparin-Sepharose column with between 0.55 and 1.5 molar aqueous NaCl under conditions as described in the Analytical Methods section herein under the heading "Separation of EC-SOD variants from cell culture media by Heparin-Sepharose Chromatography". Elution of the polypeptide or polypeptide composition with a molar aqueous NaCl of a concentration of about 1.5 reflects a very strong affinity for heparin, whereas elution with NaCl of a concentration of 0.55M reflects an affinity for heparin which is very close to the affinity of recombinant EC-SOD C. Preferably, the polypeptide or polypeptide composition of the invention has a (mean where appropriate) heparin binding affinity corresponding to complete elution of the polypeptide or polypeptide composition from a heparin-Sepharose column with between 0.55 and 1.0 molar aqueous NaCl or 0.65–1.0M NaCl or, such as with between 0.55 and 0.75 molar aqueous NaCl or 0.60–1.0M NaCl, under conditions as described in the Analytical Methods section herein under the heading "Separation of EC-SOD variants from cell culture media by Heparin-Sepharose Chromatography". More preferably, the polypeptide or polypeptide composition according of the invention has a (mean where appropriate) heparin binding affinity corresponding to complete elution of the polypeptide or polypeptide composition from a heparin-Sepharose column of between 0.55 and 0.65 molar aqueous NaCl under conditions as described in the Analytical Methods section herein under the heading "Separation of EC-SOD variants from cell culture media by Heparin-Sepharose Chromatography".

A special embodiment of the invention relates to polypeptides or polypeptide compositions of the type described above having a very substantially increased heparin affinity compared to recombinant EC-SOD C, corresponding to complete elution of the polypeptide or polypeptide composition from a heparin-Sepharose column, but at aqueous NaCl concentrations which are above 1.5 molar under the conditions described in the Analytical Methods section. Such embodiments showing extremely strong heparin binding are also within the scope of the present invention.

A polypeptide or polypeptide composition of the invention which has a reduced affinity for heparin compared to recombinant EC-SOD C normally has a (mean where appropriate) heparin binding affinity corresponding to complete elution of the polypeptide or polypeptide composition from a heparin-Sepharose column with between 0 and 0.54 molar aqueous NaCl under conditions as described in the Analytical Methods section herein under the heading "Separation of EC-SOD variants from cell culture media by Heparin-Sepharose Chromatography". Elution of the polypeptide or polypeptide composition with NaCl of a concentration close to 0M reflects an A-type affinity for heparin, whereas elution with 0.54M reflects a slightly reduced C-type. Preferably, the polypeptide or polypeptide composition of the invention has a (mean where appropriate) heparin binding affinity corresponding to complete elution of the polypeptide or polypeptide composition from a heparin-Sepharose column with between 0.0 and 0.50 molar aqueous NaCl, such as between 0.0 and 0.45 molar aqueous NaCl, e.g. between 0.0 and 0.35 molar aqueous NaCl, such as 0.10–0.25 molar aqueous NaCl, under conditions as described in the Analytical Methods section herein under the heading "Separation of EC-SOD variants from cell culture media by Heparin-Sepharose Chromatography".

As explained above, the polypeptide of the invention is normally a highly complex molecule which in most cases is glycosylated. Normally, the glycosylation site is the asparagine moiety at position 89 of the amino acid sequence constituting the polypeptide, which asparagine moiety is also the glycosylation site of native EC-SOD. In accordance with the present invention, polypeptides are contemplated which have one or more glycosylation sites different from the asparagine 89 and which have the superoxide dismutating property of native EC-SOD and a modified affinity for heparin compared to recombinant EC-SOD C. Such polypeptides are also to be understood to be within the present invention.

Alternatively, as it is explained above it has been possible, in accordance with the principles of the present invention, to construct and produce a non-glycosylated polypeptide which lacks the glycosylation site asparagine 89, which polypeptide is termed G1. This polypeptide has been found to have the superoxide dismutating property of native EC-SOD and an increased affinity for heparin compared to recombinant EC-SOD C. Also other non-glycosylated polypeptides are envisaged, which polypeptides have the superoxide dismutating property of recombinant EC-SOD and a modified, increased or reduced, affinity for heparin compared to recombinant EC-SOD C. Thus, for instance such a non-glycosylated polypeptide may be obtained on the basis of the polypeptide G1 by modifying this polypeptide by a suitable method, e.g. site-directed mutagenesis, as described in further details below. Preferably such modifications are performed in the C-Terminal part of G1. Of course, non-glycosylated polypeptides having the superoxide dismutating property of native EC-SOD and a modified affinity for heparin as compared to recombinant EC-SOD C may be constructed independently of the polypeptide G1, e.g. by substituting the glycosylation site asparagine 89 of the amino acid sequence of the polypeptide of the invention with an amino acid different from glutamine, the amino acid used in the polypeptide G1, and if desirable otherwise modify the sequence. Any non-glycosylated polypeptide which has the critical properties of the polypeptide of the invention, i.e. the superoxide dismutating property of native EC-SOD and a modified affinity for heparin compared to recombinant EC-SOD C, is to be understood as being within the scope of the present invention.

Furthermore, the present invention relates to a DNA sequence encoding a polypeptide as defined above or modifications thereof having the superoxide dismutating property of recombinant EC-SOD and having a modified binding to heparin as compared with recombinant EC-SOD C. Examples of a DNA sequence according to the invention are the sequences shown in FIG. 1A, FIG. 1B and FIG. 1C, or a modification thereof which encodes a polypeptide having the superoxide dismutating property of native EC-SOD and showing a modified heparin binding affinity as a result of one of the modifications mentioned above. The DNA sequence may be of synthetic origin, i.e. prepared synthetically by established standard methods, e.g. as described by Matthes et al., EMBO Journal 3, 1984, pp. 801–805. Alternatively, a DNA fragment encoding a polypeptide of the invention or a modification thereof which has a superoxide dismutating property of recombinant EC-SOD may be obtained by modification of a DNA sequence of complementary DNA (cDNA) origin or of genomic origin, which DNA sequence encodes native EC-SOD C. This will be explained in further detail below.

In a further aspect, the present invention relates to a replicable expression vector which comprises a DNA sequence encoding EC-SOD. In the present context, the term "replicable" means that the vector is able to replicate in a given type of host cell into which it has been introduced. The vector may be one carrying the DNA sequence shown above or any suitable modification thereof as explained above. Immediately upstream of this sequence (the coding sequence of EC-SOD) there may be provided a sequence coding for a signal peptide, the presence of which ensures secretion of the EC-SOD expressed by host cells harbouring the vector. The signal sequence may, for instance, be the following sequence:

on Sep. 14, 1989, in the European Collection of Animal Cell Cultures under the Accession Number ECACC 89091402 and CHO-DXB 11/pPEE7-pSV2dhfr deposited on Sep. 14, 1989, in the European Collection of Animal Cell Cultures under the Accession Number ECACC 89091403, which cells have been deposited under the provision of the Budapest Treaty. *E. coli* may advantageously be used for the production of EC-SOD variants according to the invention, which variants are less complex molecules such as, e.g., a glycosylation-free variant (e.g. the variant G1 described herein).

In a further aspect the present invention relates to a method of producing a polypeptide as defined above having a modified affinity for heparin compared to recombinant EC-SOD C and having the superoxide dismutating property of native EC-SOD which method comprises modifying a DNA sequence encoding native EC-SOD C by a mutagenic treatment so as to obtain a DNA fragment as defined above encoding the polypeptide, inserting said DNA fragment into a vector which is able to replicate in a host cell, introducing the resulting recombinant vector into the host cell, culturing the host cell in an appropriate culture medium under appropriate conditions for expressing the polypeptide, and recovering the polypeptide from the host cell or culture medium.

The medium used to grow the cells may be any conventional medium suitable for the purpose. Because of the high degree of similarity of the polypeptide of the invention and EC-SOD, the polypeptide of the invention is believed to contain Cu and Zn and it may be necessary to add extra Cu and/or Zn for the synthesis of the polypeptide of the invention, especially if the polypeptide is to be produced in increased amounts. A suitable vector may be any of the vectors described above,

```
    −18                          −10                                    −1
Met Leu Ala Leu Leu Cys Ser Cys Leu Leu Leu Ala Ala Gly Ala Ser Asp Ala
ATGCTGGCGCTACTGTGTTCCTGCCTGCTCCTGGCAGCCGGTGCCTCGGACGCC
TACGACCGCGATGACACAAGGACGGACGAGGACCGTCGGCCACGGAGCCTGCGG
                                                              120
``` which sequence shows the signal sequence and signal peptide preceding the sequence encoding EC-SOD C.

The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated.

The present invention further relates to a cell harbouring a replicable expression vector as defined above. In principle, this cell may be of any type of cell, i.e. a prokaryotic cell such as a bacterium, e.g. *E. coli*, a unicellular eukaryotic organism, a fungus or yeast, or a cell derived from a multicellular organism, e.g. an animal or a plant. It is, however, believed that a mammalian cell may be particularly capable of expressing a polypeptide of the invention which in most aspects is a rather complex glycosylated molecule which cells of lower organisms might not be able to produce. Examples of such cells are CHO-DXB 11/pPEE6-pSV2Ddhfr deposited and an appropriate host cell may be any of the cell types listed above. The methods employed to construct the vector and effect introduction thereof into the host cell may be any methods known for such purposes within the field of recombinant DNA.

The DNA sequence to be modified may be of cDNA or genomic origin as discussed above, but may also be of synthetic origin. Furthermore, the DNA sequence may be of mixed cDNA and genomic, mixed cDNA and synthetic or genomic and synthetic origin as discussed above. While the present discussion deals primarily with modifications which use a DNA sequence encoding native EC-SOD C as the DNA starting material, it is evident that because the amino acid sequence of EC-SOD C and the nucleotide sequence of DNA encoding native EC-SOD C are known, the DNA starting material could also be a DNA sequence which does not encode native EC-SOD C but rather a modification thereof, such DNA sequence then being modified, e.g. by site-directed mutagenesis, to result in the desired DNA fragment encoding the desired EC-SOD variant. The following discussion focused around modifications of DNA encoding native EC-SOD C should be understood to encompass also such possibilities, as well as the possibility of building up the DNA by ligation of two or more DNA fragments to obtain the desired DNA fragment, and combinations of the above-mentioned principles.

The DNA sequence, e.g. a DNA sequence encoding native EC-SOD, may be modified using any suitable technique which results in the production of a DNA fragment encoding a polypeptide of the invention. The DNA sequence may be modified in the sequence encoding part A of the polypeptide of the invention, i.e. amino acids 1–193 of EC-SOD C, or in the sequence including the amino acid sequence R of the polypeptide of the invention.

The modification of the DNA sequence encoding the amino acid sequence A of the polypeptide of the invention should be one which does not impair the superoxide dismutating property of the resulting polypeptide. Such modification may be performed on the basis of a comparison between the amino acid sequence of the polypeptide of the invention and amino acid sequences of other SOD enzymes (the great homology between the active site of EC-SOD and of other human SOD enzymes as well as of SOD enzymes from widely varying non-human sources is known and described, e.g., in Hjalmarsson et al., Proc. Natl. Acad. Sci. USA 84, 1987, pp. 6340–6344). On the basis of the comparison, the amino acids of the polypeptide of the invention which are most likely to be involved in its superoxide dismutating activity may be determined and modifications may be performed either in a region which is not contemplated to form the active site, or by modifying codons in the active site region which encode unconserved amino acid residues (on the basis of the amino acid comparison with other SOD enzymes). Furthermore, nucleotide substitutions may be made which substitutions result in a translation into the same amino acid (i.e. having either exchanged one codon with another codon encoding the same amino acid, or having exchanged a nucleotide of a codon, which nucleotide is not essential for the translation into the given amino acid).

Similarly, modification in the DNA sequence encoding part R of the polypeptide of the invention may be performed, which modification is one which either results in a modification of the heparin binding affinity of the resulting polypeptide or one which does not change the heparin binding affinity. In the latter case, one or more nucleotide substitutions may be performed which substitutions either lead to the substitution of one amino acid for another, which amino acid is not involved in the heparin binding, or which result in a changed codon which is translated into the same amino acid.

One method which has been found to be of particular use in modifying DNA sequences is the above-mentioned site-directed mutagenesis, but of course, random mutations in the DNA sequence encoding the polypeptide of the invention may also result in modified DNA sequences as described above.

Site-directed mutagenesis is a well known and very specific technique for specifically changing (mutating) nucleotides of a given nucleotide sequence, which technique is also termed oligonucleotide-directed mutagenesis. The basic principle of site-directed mutagenesis is to prime in-vitro DNA synthesis with an oligonucleotide, which is conveniently chemically synthesized, which oligonucleotide to a large extent matches the DNA sequence to be modified. The position(s) of the oligonucleotide corresponding to the position(s) of the DNA sequence to be changed do/does, however, not match, and the mismatching nucleotide(s) will be introduced into the DNA sequence upon replication. Preferably the site-specific mutagenesis is carried out on a single strand of the DNA sequence encoding EC-SOD C by use of an oligonucleotide which is identical to a subsequence of one of the strands of the DNA sequence encoding EC-SOD C except for at least one nucleotide which has been inserted, deleted, substituted or added to the sequence.

Conveniently, the single stranded DNA is obtained by cloning in M13 and the oligonucleotide is annealed to the single stranded DNA present in M13 which is subsequently replicated and transformed into a suitable host organism such as E. coli. The resulting mutants may be found by screening the E. coli clones with the oligonucleotide provided with a suitable label such as e.g. $^{32}P$.

Normally, the oligonucleotide which is used for the site-directed mutagenesis to produce the polypeptide of the invention differs from the corresponding part of the DNA sequence encoding EC-SOD C in that a) it has an insert within its sequence of at least 3 nucleotides such as at least 6 nucleotides which is different from the corresponding part of the DNA sequence encoding EC-SOD C, b) its sequence is at least 3 nucleotides, such as at least 6 nucleotides shorter than the corresponding part of the DNA sequence encoding EC-SOD C because of deletion of these nucleotides within or at one or both of the ends of the sequence, c) its sequence differs from the corresponding part of the DNA sequence encoding EC-SOD C in that at least one nucleotide of the DNA sequence encoding EC-SOD C has been substituted with another nucleotide, and/or d) at least one nucleotide has been added to one or both of the ends of the DNA sequence encoding EC-SOD C.

Normally, the oligonucleotide used comprises 5–150 nucleotides, preferably 5–50, more preferably 7–30, still more preferably 7–25 and most preferably about 21 or 23 nucleotides.

For the production of a polypeptide having the superoxide dismutating property of native EC-SOD and a reduced affinity for heparin as compared to recombinant EC-SOD C, for instance, one or several of the following strategies may be used, either separately or in combination:

a) introducing a stop codon in the C-terminal part of the DNA sequence encoding EC-SOD C by site-directed mutagenesis as described above using an oligonucleotide which is substantially identical to the 3'-part of the DNA sequence encoding native EC-SOD C except for the presence of a stop codon in the 3'-end of the oligonucleotide, so as to obtain a modified DNA sequence which results in the expression of a polypeptide which is truncated from its C-terminal end by one or more amino acid moieties and which has a reduced affinity for heparin compared to recombinant EC-SOD C. The stop codons may be introduced upstreams for one or more codons of the C-terminal end of EC-SOD C encoding positively charged amino acid moieties, e.g. Lys and/or Arg, so that a polypeptide is obtained which is truncated by one or more positively charged amino acid moieties. The truncation may alternatively be performed by an enzymatic treatment using enzymes which specifically cleaves or otherwise modifies the polypeptide sequence at specific amino acids moieties or by a chemical treatment.

b) Substituting one or more codons of the C-terminal part of the DNA sequence encoding EC-SOD C which codon(s) encode(s) positively charged amino acids such as Lys and/or Arg, with codons encoding neutral and/or negatively charged amino acid by site-directed mutagenesis using an oligonucleotide being complementary to one strand of at least a part of the C-terminal part of the DNA sequence, except for nucleotides of the codons to be substituted.

c) Adding one or more codons encoding negatively charged amino acid moieties such as Asp and/or Glu to the C-terminal part of the DNA sequence encoding EC-SOD C, so as to obtain a modified DNA sequence encoding a polypeptide having added one or more negatively charged amino acid moieties in its C-terminal part by use of site-directed mutagenesis using an oligonucleotide corresponding to the C-terminal part except for nucleotides of the codon(s) to be substituted; or by adding negatively charged amino acids to the amino acid sequence of EC-SOD C by peptide synthesis in accordance with well known techniques; or by adding codon(s) encoding negatively charged amino acids such as Asp and/or Glu to the DNA sequence encoding EC-SOD C by nucleotide synthesis.

d) Introducing negatively charged groups in the amino acid moieties of EC-SOD C by chemical synthesis in accordance with well-known methods. Thus, it may be possible to modify groups present in the amino acid moieties of the polypeptide by changing, e.g. the —SH group in Cys to the corresponding sulphonic acid group and the —OH group in Ser to the corresponding carboxylic acid group, or to introduce new groups into the amino acid moieties by using the nucleophilic property of —SH and —NH in Cys and Lys, respectively and possibly Arg, by reacting with a reagent containing a leaving group and a carboxylic acid group or a sulphonic acid group.

The truncation may alternatively be performed by an enzymatic treatment using enzymes which specifically cleaves or otherwise modifies the polypeptide sequence at specific amino acids moieties. Specific amino acid moieties may be modified by use of amino acid specific reagents, provided that these reagents modify only amino acids which do not form part of the active site of the polypeptide.

For the production of a polypeptide having the superoxide dismutating property of native EC-SOD and an increased affinity for heparin as compared to recombinant EC-SOD C, for instance, one or several of the following strategies may be used either alone or in combination:

a) Substituting one or more codons of the C-terminal part of the DNA sequence encoding EC-SOD C which codon(s) encode(s) neutral and/or negatively charged amino acids, e.g. Ser, Glu, Cys, and/or Ala, with codons encoding positively charged amino acid moieties, e.g. Arg, His and/or Lys, by site-directed mutagenesis using an oligonucleotide being complementary to one strand of at least a part of the C-terminal part of the DNA sequence, except for nucleotides of the codons to be substituted.

c) Adding one or more codons encoding positively charged amino acid moieties, e.g. Arg, His and/or Lys, to the C-terminal part of the DNA sequence encoding EC-SOD C, so as to obtain a modified DNA sequence encoding a polypeptide having added one or more positively charged amino acid moieties in its C-terminal part by use of site-directed mutagenesis using an oligonucleotide corresponding to the C-terminal part except for nucleotides of the codon(s) to be substituted; or by adding positively charged amino acids to the amino acid sequence of EC-SOD C by peptide synthesis in accordance with well known techniques; or by adding codon(s) encoding positively charged amino acids to the DNA sequence encoding EC-SOD C by nucleotide synthesis.

d) Introducing positively charged groups in the amino acid moieties of EC-SOD C by chemical synthesis in accordance with well known-methods. Thus it may be possible to modify groups present in the amino acid moieties of the polypeptide by, e.g., quarternisation of N-atoms in the side chain, in particular in Lys, Arg and His, or by introducing new groups using the nucleophilic property of —SH and —NH in Cys and Lys, respectively, and possibly, Arg, by reacting with a reagent containing a leaving group and an amino function followed by quarternisation of the amino function.

Specific examples of site-directed mutagenesis carried out in accordance with the strategies outlined above appear from Example 1.

In a further aspect, the present invention relates to an oligonucleotide which is substantially identical to at least a subsequence of one of the strands of the DNA sequence encoding EC-SOD C except for the presence or absence of at least one nucleotide different from the nucleotide at the same position of the DNA sequence encoding EC-SOD C, which oligonucleotide is suitable for use in site-specific mutagenesis to be used in the preparation of a polypeptide of the invention having the superoxide dismutating property of native EC-SOD and a modified affinity for heparin compared to recombinant EC-SOD C. The oligonucleotide is preferably of synthetic origin, i.e. prepared synthetically by established standard methods as described above, and has the characteristics described above. Examples of oligonucleotides of the invention appear from FIG. 3.

Alternatively, the polypeptide of the invention having the superoxide dismutating property of native EC-SOD and a modified affinity for heparin compared to recombinant EC-SOD C may be prepared by a method comprising inserting a DNA sequence encoding native EC-SOD C into an expression vector, introducing said vector into a host cell capable of expressing EC-SOD C, growing said host cell under condition ensuring the expression of substantial native EC-SOD C, subjecting the expressed substantial native EC-SOD C to a posttranslational modification so as to obtain the polypeptide of the invention, and recovering said polypeptide. The DNA sequence encoding native EC-SOD C is, e.g., the sequence of native EC-SOD C shown in FIG. 1, and the expression vector and host cell may be of any suitable type, e.g. of the types explained above.

Preferably, the posttranslational modification comprises chemical modification of the amino acid residues of the polypeptide sequence of native EC-SOD C, e.g. as explained above.

Any of the recombinant production methods outlined above may be carried out by use of higher organism as the host organism. Of particular interest is a production which is carried out by use of the well known transgenic techniques in which transgenic organisms such as animals are used as the host organism. Examples of suitable animals are sheep, cattle, pigs, etc. When transgenic techniques are used, the DNA encoding the polypeptide of the invention is suitably inserted into the genome of the animal in such a position that the polypeptide of the invention is expressed together with a polypeptide which inherently is expressed by the animal, preferably a polypeptide which is easily recovered from the animal, e.g. a polypeptide which is secreted by the animal such as a milk protein or the like. Suitably, the DNA fragment encoding the polypeptide of the invention is inserted in the genome of the animal in frame with the DNA fragment encoding the polypeptide inherent to the animal so as to obtain expression of a fusion protein comprising on the one hand the polypeptide of the invention and on the other hand the polypeptide related to the host organism, e.g. the animal. The resulting fusion protein may then be subjected to posttranslational modification, e.g. as described below, to obtain the polypeptide of the invention.

Alternatively, the polypeptide of the invention having the superoxide dismutating property of native EC-SOD and a modified affinity for heparin compared to recombinant EC-SOD C may be prepared by a method comprising subjecting native EC-SOD C to an enzymatic or chemical treatment, by which the native EC-SOD C is converted into a polypeptide of the invention having the formula set forth above or a modification thereof having the superoxide dismutating property of native EC-SOD.

Native EC-SOD C may be obtained from a cell line which is capable of secreting EC-SOD C. The cell line may be of mammalian, in particular human, origin. It is preferable that the cell line is one which produces particularly high quantities (compared to other cells) of EC-SOD. Thus, the cell line may be one which is derived from blood or lung, skin, blood vessel, pancreas, uterus, prostate gland, placenta or umbilical cord tissue or, possibly, neoplastic tissue. In particular, it is contemplated that cell lines derived from fibroblasts or glia cells are particularly advantageous as sources of EC-SOD.

Of course, and preferably, the native EC-SOD C to be used for the preparation of the polypeptide of the invention may be of recombinant origin produced by conventional recombinant techniques, e.g. as described above. The recombinant production of native EC-SOD is described in details in WO 87/01387.

The recombinantly produced polypeptide of the invention which is expressed by cells may be secreted, i.e. exported through the cell membrane, dependent on the type of cell and the composition of the vector. If the polypeptide is produced intracellularly by the recombinant host, that is, is not secreted by the cell, it may be recovered by standard procedures comprising cell disrupture by mechanical means, e.g. sonication or homogenization, or by enzymatic or chemical means followed by purification (examples of the purification and recovery procedures are given in Examples 2, and 4–6).

In order to be secreted, the DNA sequence encoding the polypeptide should be preceded by a sequence coding for a signal peptide, the presence of which ensures secretion of the polypeptide from the cells so that at least a significant proportion of the polypeptide expressed is secreted into the culture medium and recovered.

The polypeptide may be recovered from the medium by standard procedures comprising filtering off the cells and isolating the secreted protein. In order to ensure the release of EC-SOD from the cell surfaces, and thus obtain an improved yield, it may be advantageous to add heparin or one of the substances with a similar effect mentioned above to the medium in which the cells expressing the polypeptide of the invention is grown.

As mentioned above, the polypeptide of the invention shows an affinity to heparin which indicates an affinity to heparan sulphate or other heparin-like glucosaminoglucans found on cell surfaces, especially on the surface of endothelial cells. It is therefore contemplated to induce the release of EC-SOD from cell surfaces and thereby ensure an improved yield of EC-SOD by growing the tissue cells of the EC-SOD producing cell lines in a medium containing heparin or a heparin analogue, e.g. heparan sulphate, or another sulphated glucosaminoglycan, dextran sulphate or another strongly negatively charged compound in an amount which is sufficient to induce the release of EC-SOD from the cell surfaces.

The polypeptide composition of the invention defined above may be prepared by a method comprising a) cotransfecting expression vectors which separately comprise the DNA sequence encoding each of the polypeptides to be included in the polypeptide composition by introducing each of the vectors into a host cell which is capable of expressing the polypeptides, culturing the host cell under conditions suitable for expressing each of the polypeptides to be included in the polypeptide composition, and recovering and separating the culture medium comprising the polypeptide composition, or b) coincubating a sample of each of the polypeptides to be included in the polypeptide composition under suitable conditions so as to obtain the polypeptide composition.

The cotransfection used for preparing the polypeptide composition of the present invention may be carried out in accordance with techniques known in the art, e.g. by the technique described in Example 2 below. The actual cotransfection method used is not critical as long as it results in the introduction of the two expression vectors each encoding a polypeptide of the invention.

Alternatively, one of the expression vectors may encode EC-SOD C to be included in the polypeptide composition. The host organism or cell into which the expression vectors are introduced may be any conventional organism or cell which is capable of expressing the polypeptides and may e.g. be a mammalian cell line such as CHO. The cultivation of the host cell or organism and the recovering of the polypeptide composition may be carried out as described above.

The DNA sequences encoding the polypeptide constituents of the polypeptide composition of the invention may alternatively be carried by the same expression vector in a manner which allows for the expression of both of the polypeptides or either separately. The expression vector carrying both DNA sequences may be introduced into the host cell or organism by the normal procedure, e.g. as described above.

The coincubation of a sample of each of the polypeptides of the polypeptide composition serves to dissolve the oligomer form in question of each of the polypeptides and recombine the resulting subunits and may be performed by simply mixing polypeptide samples obtained as described herein and subsequently incubating the mixture, e.g. with gentle stirring, at a temperature which will not give rise to degradation of the structure of the polypeptide, for example a temperature in the range of 20°–50° C. or maybe even higher such as in certain cases up to 60° C., often at a temperature of about 37° C., so as to achieve recombination of the polypeptide species into mixed or heterologous oligomers. Preferably, the polypeptides are dissolved in a physiologically acceptable solvent, such as water, or an aqueous physiological acceptable solution such as α-medium, such as explained in the examples.

The polypeptide of the invention having the superoxide dismutating property of native EC-SOD and a modified affinity for heparin compared to recombinant EC-SOD C may be recovered from the organism in which it is produced or the medium to which it is secreted by adsorption to a matrix containing immobilized antibodies against the polypeptide of the invention, or against EC-SOD or an immunological determinant thereof, eluting the EC-SOD activity from the matrix, and pooling the fractions containing the EC-SOD activity, and optionally subjecting the pooled fractions to further purification. The antibodies employed may be antibodies raised against the polypeptide of the invention, but may also be antibodies raised against EC-SOD or an immunological determinant thereof, which antibodies, because of the high degree of homology between the polypeptide of the invention and EC-SOD, on most cases will react with the polypeptide of the invention (vide Example 8). The antibodies used for the recovery of the polypeptide of the invention is immobilized on a suitable matrix material in a manner known per se.

The antibodies employed for affinity chromatography according to the invention may either be polyclonal or monoclonal antibodies. The currently preferred antibodies are monoclonal antibodies as most monoclonal antibodies have been found to bind the antigen less strongly than the polyclonal antibody mixture which means that desorption may be carried out under milder conditions with weaker eluants. This may result in an improved yield of the polypeptide of the invention as there is a lower degree of denaturation than when strong eluants are used for desorption.

Also, since all the IgG will be directed against the polypeptide of the invention, a far smaller amount of antibody matrix will have to be used for the adsorption of the polypeptide from the material from which it has to be recovered. The desorption of the polypeptide will require a far smaller volume of eluant, thereby simplifying the elution procedures which are at present inconvenient due to the large volumes of eluant needed for the desorption.

The specificity of monoclonal antibodies for the polypeptide of the invention is likely to be higher than that of the polyclonal antibodies. The eluate from the antibody matrix will therefore be purer which means that one or more further purification steps may be omitted. This means that the production procedure will be greatly simplified and a far higher yield will be obtained which presents an important economic advantage.

Polyclonal antibodies may be obtained by immunizing an immunizable animal with the polypeptide of the invention or an immunological determinant thereof and obtaining antiserum such as immunoglobulins from the animal in a manner known per se. The immunization is preferably performed by means of a stabilized aqueous solution of the polypeptide; the stabilization agent may be a buffer such as phosphate buffered saline or an adjuvant (also to further increase the antigenicity), and a suitable adjuvant is Freund's adjuvant or aluminium hydroxide. For immunization purposes, mice, rabbits, hens, goats and sheep are the preferred animals. The bleeding of the animal and the isolation of the antiserum is performed according to well-known methods. The antibody is preferably provided in substantially pure form which is advantageous in order to obtain the necessary purification of the polypeptide of the invention.

When using a monoclonal antibody for the recovering of the polypeptide of the invention, it may be produced by a hybridoma technique which is well-known method for producing antibodies. In the hybridoma technique using, for instance, mice as the animals immunized, mice are immunized with the antigen in question and spleen cells from the immunized mice are fused with myeloma cells whereupon the fused hybridoma cells are cloned, antibody-producing cells are grown in a suitable growth medium and the antibodies are recovered from the culture. The antibodies obtained by the hybridoma technique have the advantage of greater specificity and, hence, a greater purifying potential as mentioned above. In a possible further step, using recombinant DNA techniques, the DNA sequence encoding the antibody is transferred from the hybridoma cell clone to a suitable vector, the hybrid vector is transformed to a suitable bacterial host, the host is grown in an appropriate medium and the resulting antibody is recovered from the culture. In this way, an improved yield of antibody may be obtained. The host may be one usually employed in the field of recombinant DNA technology such as *Escherichia coli* or *Bacillus subtilis*.

In an alternative method of obtaining monoclonal antibodies, the hybridoma cells may be implanted and grown in the abdominal cavity of mice, and the resulting antibodies against the polypeptide of the invention are recovered from the ascitic fluid produced, in a manner known per se. Furthermore, immunization for obtaining monoclonal antibodies may be performed in vitro using immunocompetent cells from, e.g., mice. In this case it is not necessary to inject an antigen into the animal in question, e.g. a mouse, although this is at present the most commonly employed procedure. It should be noted that monoclonal antibodies and the method of preparing them form one aspect of the invention.

In most cases, especially when employing immobilized polyclonal antibodies for the purification of the polypeptide of the invention, the pooled eluate of the antibody matrix may be absorbed to a matrix, e.g. an ion-exchange matrix, followed by eluting the EC-SOD activity from the matrix and pooling fractions containing the EC-SOD activity. Further purification of the pooled eluate may be obtained by applying it on a chromatographic column of a matrix comprising heparin or a heparin analogue, e.g. heparan sulphate, or another sulphated glucosaminoglycan, dextran sulphate or another strongly negatively charged compound and eluting followed by pooling the fractions showing affinity to the substance in question.

The polypeptide of the invention which has been recovered by adsorption as described above is preferably eluted with an eluent such as NaCl, which has been found to be very efficient and which is also the eluent used for evaluating the heparin affinity of the polypeptide of the invention.

In a yet further, very important aspect, the present invention relates to the use of a polypeptide of the invention having the superoxide dismutating property of native EC-SOD and a modified affinity for heparin compared with recombinant EC-SOD C, for the diagnosis, prophylaxis or treatment of diseases or disorders connected with the presence or formation of superoxide radicals and other toxic oxygen intermediates derived from the superoxide radical.

Examples of such diseases or disorders are selected from conditions involving ischaemia followed by reperfusion, e.g. infarctions such as heart, kidney, brain, spinal cord, or intestinal infarctions; transplantation of organs such as heart, lung, pancreas, liver, skin, bone tissue, severed extremities, skeletal muscle; inflammatory diseases such as rheumatoid arthritis, pancreatitis, in particular acute pancreatitis, pyelonephritis and other types of nephritis, and hepatitis, neuritis, uveitis, cystitis, peyronies disease, autoimmune diseases, insulin-dependent diabetes mellitus, disseminated intravascular coagulation, fatty embolism, haemorrhagic shock, endotoxin-induced shock, septicemia, severe viral infections, adult respiratory distress, infantile respiratory distress, brain haemorrhages in neonates, burns, preservation of lens and cornea in the context of transplantation, adverse effects of ionizing radiation, carcinogenesis, and adverse effects of toxins such as alloxan, paraquat, and some cytostatic compounds.

Thus, the polypeptide of the invention is indicated for substantially the same applications as CuZn SOD the therapeutic activity of which has been more thoroughly documented as discussed below. EC-SOD and the EC-SOD variants of the invention have, however, been found to possess a number of characteristics which are assumed to make them particularly useful for therapeutic applications. The property of the new EC-SOD variants of the invention of having a heparin affinity different from that of recombinant EC-SOD C is likely to confer upon them a considerable advantage in terms of therapeutic usefulness, as compared with recombinant EC-SOD C.

CuZn SOD has a low molecular weight (33,000) which causes it to become eliminated very quickly by glomerular filtration in the kidneys so that in rodents it has a plasma half-life of less than 10 minutes and, in human beings, the enzyme has a half-life of about 20-30 minutes. EC-SOD C (K. Karlsson et al., J. Clin. Invest. 82, 1988, pp. 762-766) and the EC-SOD variants presented in this application (Examples 1, 2,& 4) have a much longer half-life. This is partly due to the high molecular weight of EC-SOD and EC-SOD variants of the invention which prevents them from being eliminated by glomerular filtration, and partly due to the fact that EC-SOD and EC-SOD variants of the invention of the C-type seem to bind to endothelial cell surfaces (K. Karlsson et al., Biochem. J. 242, 1987, pp. 55-59; K. Karlsson et al., Biochem. J. 255, 1988, pp. 223-228; K. Karlsson et al., J. Clin. Invest. 82, 1988, pp. 762-766; K. Karlsson et al., Lab. Invest. 60, 1989, pp. 659-666). In the therapeutic use of EC-SOD and variants according to the invention, the enzyme therefore preferably has a half-life in human beings of at least 4 hours and possibly even longer.

As explained above, EC-SOD is, in its native environment, a secreted protein and it is therefore likely that it is specifically synthesized for a function in extracellular space (in extracellular fluids or on cell surfaces) which may cause it to exhibit properties which are particularly well adapted to protect plasma components or the outer surface of cells against the toxic effects of superoxide radicals or other oxygen radicals. A fundamental property of EC-SOD C, and most likely also a polypeptide of the invention having a slightly reduced affinity for heparin compared to the heparin affinity of recombinant EC-SOD C, e.g. the polypeptide of the invention T216 described herein (Examples 1, 2 and 4), is its affinity for heparan sulfate which in vivo apparently has the correlate of binding to heparan sulfate proteoglycan in the glycocalyx of cell surfaces and in the interstitial connective tissue matrix (K. Karlsson et al., Biochem. J. 242, 1987, pp. 55-59; K. Karlsson et al., Biochem. J. 255, 1988, pp. 223-228; K. Karlsson et al., J. Clin. Invest. 82, 1988, pp. 762-766; K. Karlsson et al., Biochem. J. 256, 1988, pp. 29-33; K. Karlsson et al., Lab. Invest. 60, 1989, pp. 659-666; K. Karlsson et al., Biochem. Biophys. Acta 967, 1988, pp. 110-114). This property would seem to be a particularly efficient way to protect cells and tissues against an external superoxide radical source.

The significance of the apparent association of EC-SOD and EC-SOD variants of the invention with cell membranes is further supported the finding that CuZn SOD which has been modified with polylysine to bind to cell membranes is better able to protect activated (superoxide radical-producing) polymorphonuclear leukocytes (PMN) from autoinactivation (cell death) than normal CuZn SOD which is negatively charged and therefore tends to be repelled by the cell membranes (M. Salin and J. M. Mc Cord, "Free radicals in leukocyte metabolism and inflammation", in Superoxide and Superoxide Dismutases, eds. A. M. Michelson, J. M. McCord and I. Fridovich, Academic Press, 1977, pp. 257-270). The fact that *Nocardia asteroides* possesses a membrane-associated SOD which appears to confer efficient protection against activated human PMNs as the susceptibility of Nocardia to PMNs is significantly increased when Nocardia cells are treated with antibodies towards this SOD (B. L. Beaman et al., Infect. Immun. 47, 1985, pp. 135-141) also points to a cell membrane-protective function of SOD bound to cell surfaces. Unlike EC-SOD and EC-SOD variants or the invention, CuZn SOD has an intracellular function which may make it less well suited for extracellular application, i.e. occasioned by the extracellular presence of superoxide radicals. Furthermore, its brief half-like compared to that of EC-SOD and EC-SOD variants or the invention mentioned above would seem to make it necessary to administer larger doses at shorter intervals than is likely to be the case with the EC-SOD variants of the invention.

SOD activity for potential therapeutic applications has been demonstrated for the following diseases or disorders.

Parenterally administered CuZn SOD has been shown to exhibit an anti-inflammatory effect in a series of animal models of inflammation as well as in inflammatory diseases in animals (Huber and Saifer, in Superoxide and Superoxide Dismutases, eds. Michelson et al., Academic Press, 1977, pp. 517-549). In humans, positive effects of CuZn SOD has been reported in rheumatoid arthritis and arthroses, in inflammation of the bladder and other urological conditions (Menander-Huber in Biological and Clinical Aspects of Superoxide and Superoxide Dismutase, eds. Bannister et al., Elsevier/North Holland, 1980, pp. 408-423) as well as adverse effects of treatment with ionizing radiation (Edsmyr et al. Current Therapy. Res. 10, 1976, pp. 198-211; Cividalli et al., Acta. Radiol. Oncol. 24, 1985, pp. 273-277 (in rats)). In some countries, bovine CuZn SOD has become registered as a drug (Orgotein, Peroxinorm), employed mainly for the treatment of arthritis and arthroses where the composition is administered intraarticularly (Goebel and Storck, Am. J. Med. 74, 1983, pp. 124-128), but also for urological conditions.

Parenterally administered CuZn SOD is not taken up by the cells and must exert its activity in the extracellular space. CuZn SOD encapsulated in liposomes is taken up by the cells and is reported to be effective against Crohn's disease, Bechet's disease, dermatitis herpetiformis, ulcerative coliris, Kawasaki's disease and against the adverse effects of radiation therapy (Y. Niwa et al., Free Rad. Res. Comms. 1, 1985, pp. 137-153). The mechanism of the anti-inflammatory activity of CuZn SOD is not quite clear. Direct protection against oxygen radicals formed by activated leukocytes has been suggested (Halliwell, Cell Biol. Int. Rep. 6, 1982, pp. 529-541). Another possibility is prevention of the formation of a superoxide induced strongly chemotaxic substance (Petrone et al., Proc. Natl. Acad. Sci. USA 77, 1980, pp. 1159-1163).

The other large potential area of application for SOD is as a protective factor against tissue damage caused by ischaemia followed by reperfusion. If the supply of blood to a tissue is cut off, the tissue will slowly become necrotic. Macro- and microscopically the damage will typically develop slowly over many hours. If the tissue is reperfused after, for instance, one hour, a strong acceleration of the tissue damage will occur instead of an improvement. Most likely there are several reasons for this so-called reperfusion paradox, but oxygen radicals formed as a result of the reappearance of oxygen in previously ischaemic tissue appear to contribute to the damage. The radicals are extremely shortlived and therefore difficult to study directly, and much of the information concerning their formation and effects is inferred from the protective action of various oxygen radical scavengers. Their formation have however also been demonstrated more directly by means of EPR on heart samples (Zweier et al., J. Clin. Invest. 80, 1987, pp. 1728-1734) and by means of spin traps in heart reperfusion (e.g. P. B. Garlick et al., Circ. Res. 61, 1987, 751-760; R. Bolli et al., J. Clin. Invest. 82, 1988, 476-485). Tissue protection by means of CuZn SOD has been demonstrated in ischaemia- or anoxia-reperfusion models in the kidney (G. L. Baker et al., Am. Surg. 202, 1985, pp. 628-641; I. Koyama et al., Transplantation 40, 1985, pp. 590-595; E. Hansson et al., Clin. Sci. 65, 1983, pp. 605-610; A. Bayati et al., Acta Physiol. Stand. 130, 1987, pp. 367-372; J. F. Bennett et al., Cryobiology 24, 1987, pp. 264-269; T. Hoshino et al., Transplantation 45, 1988, pp. 284-289; P. J. Bosco et al., Arch. Surg. 123, 1988, pp. 601-604), intestine (D. A. Parks et al., Gastroenterology 82, 1982, pp. 9-15; M. H. Schoenberg et al., Acta Chim. Scand. 150, 1984, pp. 301-309; M. C. Dalsing et al., J. Surg. Res. 34, 1983, pp. 589-596; M. Younes et al., Res. Exp. Med. 187, 1987, pp. 9-17), pancreas (H. Sanfey et al., Ann. Surg. 200, 1983, pp. 405-413), liver (S. L. Atalla et al., Transplantation 40, 1985, pp. 584-589; G. Nordström et al., Circ. Shock 26, 1988, pp. 115-126), lung (R. S. Stuart et al., Transplant. Proc. 17, 1985, pp. 1454-1456; I. Koyama et al., I. Koyama et al., J. Appl. Physiol., 63, 1987, pp. 111-115), skeletal muscle (R. V. Korthuis, Circ. Res. 57, 1985, pp. 599-609), skin (M. J. Im et al., Ann. Surg. 201, 1985, pp. 357-359; A. Sagi et al., Plast. Reconstr. Surg. 77, 1986, pp. 639-642; L. Huang et al., FASEB J. 1, 1987, pp. 129-132; T. J. Zimmerman et al., Ann. Plast. Surg. 18, 1987, pp. 218-223; A. T. Pokorny et al., Arch. Otolar. Head Neck Surg. 115, 1989, pp. 207-212), brain (J. P. Pigott et al., J. Vasc. Surg. 7, 1988, pp. 625-630; T. H. Liu et al., Am. J. Physiol. 256, 1989, pp. H589-H593), spinal cord (K. H. Lim et al., Ann. Thorac. Surg. 42, 1986, pp. 282-286; P. Cuevas et al., Anat. Embryol. 179, 1989, 251-255), and bone tissue (A.-P. C. Weiss et al., Plast. Reconstr. Surg. 82, 1988, pp. 486-495).

Preservation of heart function has been reported in isolated, perfused preparations from the cat (M. Schlafer et al., Circulation 66, Suppl. I, 1982, pp. 185-192) and rat (Gaudel et al., J. Mol. Cell Cardiol. 16, 1984, pp. 459-470). In regional ischaemia-reperfusion models in vivo, reduction of infarct size has been reported in the dog (T. J. Gardner et al., Surgery 94, 1983, pp. 423-427; D. E. Chambers et al., J. Mol. Cell Cardiol. 17, 1985, pp. 145-152; S. W. Werns et al., Circ. Res. 56, 1985, pp. 895-898; G. Ambrosio et al., Circulation 72, 1986, pp. 1424-1433), in the pig (U. Näslund et al., J. Mol. Cell Cardiol. 18, 1986, pp. 1077-1084) and the rat (N. Aoki et al., Br. J. Pharmacol. 95, 1988, pp. 735-740). Protection by CuZn SOD has also been reported in models designed to mimic heart transplantation (M. J. Jurmann et al., J. Thorac. Cardiovasc. Surg. 95, 1988, pp. 368-377; F. Gharagozloo et al., J. Thorac. Cardiovasc. Surg. 95, 1988, pp. 1008-1013; J. R. Stewart et al., Ann. Thorac. Surg. 42, 1986, pp. 390-393) and reperfusion after cardiopulmonary bypass (F. Gharagozloo et al., J. Thorac. Cardiovasc. Surg. 95, 1988, pp. 631-636). Injection of SOD+catalase has also been reported to preserve the mechanical heart function after a brief (15 minutes) regional ischaemia in the dog (M. L. Myers et al., Circulation 72, 1985, pp. 915-921; K. Przyklenk and R. A. Kloner, Circ. Res. 58 1986, pp. 148-156). Furthermore, SOD has been reported to reduce the incidence of ischaemia-and-reperfusion induced arrythmias (B. Woodward et al., J. Mol. Cell. Cariol. 17, 1985, pp. 485-493; M. Bernier et al., Circ. Res. 58, 1986, pp. 331-340; Tamwray et al., Circ. Res. 63, 1988, pp. 944-959). It is contemplated that EC-SOD and EC-SOD variants of the invention might be used in connection with thrombolytic agents such as streptokinase, tissue plasminogen activator, urokinase and variants and variants of these factors. Enhanced myocardial salvage by the combined treatment with urokinase and CuZn SOD (U. Fincke et al., Arzneim.-Forsch./Drug Res. 38, 1988, pp. 138-142) has been reported in a canine coronary thrombosis model.

Furthermore CuZn SOD has been shown to enhance the thrombolytic effects of tissue plasminogen activator in the dog heart. The result was hypothesized to be due to preservation of Endothelin-Derived Relaxation Factor (EDRF), resulting in reduced platelet aggregation and better vasodilation during reperfusion (J. L. Mehta et al., Doctoral thesis, Faculty of Medicine, Upsaliensis, no. 215, 1989, Acta Universitatis).

The source of oxygen radicals in this situation is not completely clear, but the effect of allopurinol seems to indicate that it is partly caused by xanthine oxidase which, by ischaemia, is converted from its xanthine dehydrogenase form (Parks et al., op. cit.) to the radical-producing oxidase form. A large amount of hypoxanthine which is the substrate for xanthine oxidase is formed due to purine nucleotide degradation induced by ischaemia. Other sources of superoxide radicals may be activated leukocytes attracted to ischaemia-damaged tissue, prostaglandin synthesis ($O_2.^-$ is a byproduct; Kontos, Circ. Res. 57, 1985, pp. 508–516) and autooxidation of various compounds accumulated in reduced form during ischaemia. The finding concerning ischaemia followed by reperfusion has potentially important clinical applications. It may be possible to obtain an excellent effect by reperfusion of tissue in connection with heart infarctions, by the concomitant administration of a SOD such as EC-SOD or a polypeptide of the invention and/or other protective factors against oxygen radicals and thrombolytic factors, e.g. tissue plasminogen activator. The results of the SOD experiments also indicate a possible application in connection with heart surgery and heart transplantations. Analogously, the results of employing an SOD in connection with kidney ischaemia followed by reperfusion indicate that SOD may be employed in connection with kidney transplantations and other organs transplantations such as skin, lung, liver, pancreas, bone tissue transplantations. Ischaemic brain disease is another possible indication.

SODs show interesting protective effects in connection with other pathological conditions.

A variety of gastroenterological application are suggested by results in the literature. Parenteral CuZn SOD ameliorates experimental necrotizing enterocolitis in rabbits (D. A. Clark et al., Am. J. Path. 130, 1988, pp. 537–542; M. J. S. Miller et al., Am. J. Physiol. 255, 1988, pp. G556–G565). A protection of gastric mucosa by parenteral CuZn SOD against the effects of a variety of agents has been reported in animal models; temporary reduction of celiac artery pressure (M. A. Perry et al., Gastroenterology 90, 1986, pp. 362–367), haemorrhagic shock (C. von Ritter et al., Dig. Dis. Sci. 33, 1988, pp. 857864; M. Itoh et al., Gastroenterology 88, 1985, 1162–1167), ethanol and aspirin administration (G. Pihan et al., Digest. Dis. Sci. 32, 1987, pp. 1395–1401), and E. coli sepsis (S. Arvidsson et al., Circ. Shock 16, 1985, pp. 383–393). The wound margin strength after intestinal anastomosis is enhanced by parenteral CuZn SOD (H. Högström and U. Haglund, Surgery 99, 1986, 716–720).

Hepatitis and hepatic injury experimentally induced by many means is counteracted by parenteral CuZn SOD; ethanol (M. Younes et al., Free Rad. Res. Comms. 3, 1987, pp. 19–26); corynebacterium parvum plus endotoxin (M. J. P. Arthur et al., Gastroenterology 89, 1985, pp. 1114–1122); injection of galactoseamine and galactoseamine-latex particles (Y. Shiratori et al., Hepatology 8, 1988, pp. 815–821); injection of galactoseamine plus endotoxin (A. Wendel et al., Biochem. Pharmacol. 36, 1987, pp. 2637–2639); and hypoxia (A. Yoshioka et al., J. Dermatol. 14, 1987, pp. 569–575).

Parenterally administered CuZn SOD also ameliorates acute pancreatitis induced by infusion of oleic acid, partial obstruction of the excretory ducts and ischaemia followed by reperfusion (Sanfey et al., Ann. Surg. 200, 1984, pp. 405–413); and by cerulein-infusion (K. S. Gulce et al., Am. J. Surg. 151, 1986, pp. 163–169; A. Dabrowski et al., Scand. J. Gastroenterol. 23, 1988, pp. 1245–1249; J. Wisher et al., Gut 29, 1988, pp. 1516–1523). The results indicate the possibility of an active therapy against this disease for which no specific therapy exists at present.

It has also been suggested that treatment with SOD is effective against burns. The local oedema after an experimental slight burn in rats could be somewhat decreased through injection of SOD (Björk and Artursson, Burns 9, 1983, pp. 249–256). In an animal model involving severe burn damage of mice a dramatic protection was obtained by means of SOD, where survival and local damage were concerned (Saez et al., Circulatory Shock 12, 1984, pp. 220–239). Burn-induced intravascular hemolysis is reduced by polyethyleneglycol-substituted CuZn SOD (Hatherill et al., J. Clin. Invest. 78, pp. 629–636) as is burn-induced myocardial depression (J. W. Horton et al., J. Burn Care Rehabil. 9, 1988, pp. 589–598).

In the case of, for instance, burns, immunocomplex formation, and major tissue damage, neutrophilic leukocytes are accumulated in the lungs. Complement activation (C5 a) often seems to mediate the accumulation. The leukocytes seem to be activated and release oxygen radicals, thereby causing lung damage which, for instance, is characterized by increased vessel permeability and lung oedema (adult respiratory distress). In several animal models, SOD and other oxygen radical scavengers have been shown to have a protective effect against lung damage (Till and Ward, Agents and Actions, Suppl. 12, 1983, pp. 383–396). Protection by CuZn SOD against other lung damage models have also been reported; oedema formation during perfusion (B. Risberg et al., Eur. Surg. Res. 17, 1985, pp. 230–236); intrabronchial installation of Phorbol Myristate Acetate (PMA) (I. U. Schraufstätter et al., J. Clin. Invest. 73, 1984, pp. 1175–1184; J. S. Kerr et al., Agent. Action. 21, 1987, pp. 293–296); xanthine oxidase (O. D. Saugstad et al., Intensive Care Med. 13, 1987, pp. 30–32); or hyperoxia (R. V. Padmanabhan et al., Am. Rev. Respir. Dis. 132, 1985, pp. 164–167).

Parenterally administered CuZn SOD has been reported to prevent bronchopulmonary dysplasia in preterm neonates suffering from infantile respiratory distress (W. Rosenfeld et al., J. Pediatr. 105, 1984, pp. 781–785).

Concerning the central nervous system, protective effects of CuZn SOD have been shown against posttraumatic brain oedema (P. H. Chan et al., Ann. Neurol. 21, 1987, pp. 540–547) and experimental autoimmune neuritis (H.-P. Hartung et al., Ann. Neurol. 23, 1988, pp. 453–460). In a beagle puppy model, injection of SOD has been reported to reduce the frequency of intraventricular brain haemorrhage following hypotension (L. R. Ment et al., J. Neurosurg. 62, 1985, J63–J69).

The endothelium-derived vessel relaxant factor (EDRF) is very sensitive to superoxide, and administration of SOD augments its actions (R. J. Gryglewski et al., Nature 320, 1986, pp. 454–456; G. M. Rubanyi et al., Am. J. Physiol. 250, 1986, pp. H822–H827). Superoxide radical production can occur under many circumstances in the body and may cause vasoconstriction and decreased tissue perfusion. Administration of SOD is believed to be able to relieve such vasoconstriction and also to enhance other effects of EDRF such as platelet stabilization.

Acute severe increase in blood pressure leads to functional and morphologic abnormalities in brain arterioles. Prostaglandin synthesis inhibitors and superoxide dismutase is contemplated to protect against the abnormalities. Superoxide release can be detected (H. A. Kontos, Circ. Res. 57, 1985, pp. 508–516). Close analysis of the model has lead to the conclusion that superoxide radicals are formed as a byproduct during prostaglandin synthesis. The results suggest that tissue damage caused by superoxide radicals released during prostaglandin synthesis may occur in other pathological situation and that SOD may exert a protective action.

CuZn SOD+catalase in the medium have been reported to prolong the survival of the perfused isolated rabbit cornea (O. N. Lux et al., Curr. Eye Res. 4, 1985, pp. 153–154). CuZn SOD+catalase protect the isolated lens against photoperoxidation (S. D. Varma et al., Ophthalmic Res. 14, 1982, pp. 167–175). The results suggest possible beneficial effects of SOD in cornea transplantations and other ophthalmic surgical procedures. Parenteral CuZn SOD protects against uveitis induced by injection of lens protein (N. A. Rao et al., Ophthalmic Res. 18, 1986, pp. 41–46) and soluble retinal antigen (N. A. Rao et al., Invest. Ophthalmol. Visual Sci. 28, 1987, pp. 886–892).

Ameliorative action of parenteral SOD has been reported in animal models of such acute conditions as disseminated intravascular coagulation (T. Yoshikawa et al., Thromb. Haemostas. 50, 1983, pp. 869–872), septicemia (H. F. Welter et al., Chirurgisches Forum '85 f. experim. u. klinischer Forschung, Springer- Verlag, Berlin, 1985), and endotoxin-induced shock (C. W. Broner et al., Crit. Care Med. 16, 1988, pp. 848–850).

Parenteral SOD has been reported to enhance survival in an acute viral infection in mice (T. Oda et al., Science 244, 1989, 974–976).

In various types of autoimmune disease, such as systemic lupus erythematosus (SLE), systemic sclerosis and rheumatoid arthritis, an increased frequency of chromosomal breaks in lymphocytes has been demonstrated (Emerit, "Properties and action mechanisms of clastogenic factors", in Lymphokines, Vol. 8, ed. E. Pick, Academic Press, 1983, pp. 413–424). Fibroblast cultures and direct bone marrow preparations also sometimes show increased breakage. Plasma from such patients contains a chromosome breaking—clastogenic—factor. In some instances a similar factor has also been demonstrated in synovial fluid and in cerebrospinal fluid (disseminated sclerosis). Breaks occur in normal lymphocytes which are cocultivated with lymphocytes from patients with autoimmune disease. Lymphocytes from patients condition culture media to produce chromosome breaks. The clastogenic activity of SLE plasma can be increased by UV-irradiation. Production of superoxide in plasma by means of xanthine oxidase and xanthine results in formation of clastogenic activity. In all the above described models, addition of CuZn SOD to the medium protected against the clastogenic activity (Emerit, ibid.). This indicates that superoxide radicals are involved in both the formation and actions of the clastogenic factor (Emerit, ibid.). In an animal model of SLE, the New Zealand black mouse which possesses the clastogenic factor, the chromosomes are protected in bone marrow cells in vivo by repeated injections of SOD (Emerit et al., Cytogenet. Cell Genet. 30, 1982, pp. 65–69). It is, however, still unclear to what extent the clastogenic factor contributes to the major symptoms in human autoimmune disease and whether administration of SOD has any therapeutic effect.

The neoplastic transformation of cells is usually divided into two phases, i.e. initiation followed by promotion. In in vitro models where initiation has been caused by ionizing radiation, bleomycin, misonidazole and other nitroimidazoles, the oncogenic transformation has been effectively inhibited by the presence of SOD in the medium. It is not necessary for SOD to be present during exposure to the initiating substances which seems to indicate that the enzyme inhibits the subsequent promotion step (Miller et al., Int. J. Radiat. Oncol. Biol. Phys. 8, 1982, pp. 771–775; Borek and Troll, Proc. Nat. Acad. Sci. USA 80, 1983, pp. 1304–1307). Non-toxic doses of xanthine+xanthine oxidase causes promotion in growing cells. Addition of SOD or SOD+catalase inhibits this effect (Zimmerman and Cerutti, Proc. Nat. Acad. Sci. USA 81, 1984, pp. 2085–2087). Phorbol esters are known promoters. In a model in which skin tumors were induced by initiation with a benzanthracene followed by application of a phorbol ester (TPA), local treatment with a lipophilic copper complex with SOD activity strongly reduced tumor formation (Kenzler et al., Science 221, 1983, pp. 75–77). The result indicates that, at least in certain cases, superoxide radicals contribute to the promotion of tumor formation and that SOD may protect against this effect.

There is reason to believe that oxygen radicals contribute to the damaging effects of a number of toxic substances such as bleomycin, adriamycin, alloxan, 6-hydroxydopamine, paraquat, dihydroxyfumaric acid, nitrofurantoin and streptozotocin. In those cases where radical formation takes place in the extracellular space it might be possible to protect by means of injected protective enzyme. Thus, SOD may protect against the diabetogenic activity of alloxan (damages $\beta$-cells in the pancreas) in vitro (Grankvist et al., Biochem. J. 182, 1979, pp. 17–25) and in vivo (Grankvist et al., Nature 294, 1981, pp. 158–160). The damaging effect of alloxan seems therefore to be mediated by the superoxide radical or by other oxygen radicals derived from it. The reason for the great sensitivity of the $\beta$-cells to alloxan is not clear, and it has been speculated whether there is any connection between alloxan sensitivity and the incidence of insulin-dependent diabetes mellitus. In diabetes mellitus there is an infiltration in the Langerhans' islets by inflammatory cells which potentially may form oxygen radicals. It may therefore be contemplated to protect the $\beta$-cells by injections with SODs such as EC-SOD or a polypeptide of the invention at the first onset of diabetes mellitus.

It has been reported (Mossman and Landesman, Chest 835, 1983, pp. 50s–51s) that SOD added to the growth medium protects tracheal cells against asbestos.

It has been described (Roberts et al., J. Urol. 128, 1982, pp. 1394–1400; A. Kaur et al., Biochem. Int. 16, 1988, pp. 1083–1094) that parenteral CuZn SOD protects kidneys against experimentally induced pyelonephritis. CuZn SOD protects against acute nephritis induced in rats by anti-glomerular basement membrane antibodies (A. Rehan et al., Lab. Invest. 51, 1984, pp. 396–403), and nephrotoxic serum (T. Adachi et al., Biochem. Pharmacol. 35, 1986, pp. 341–345). Furthermore a protection against aminonucleoside nephritis has been demonstrated (J. R. Diamond et al., Kidney Int. 29, 1986, pp. 478–483; M. Beaman et al., Clin. Sci. 73, 1987, pp. 329–332).

Generally, CuZn SOD has been employed as the test substance in the experiments described above. It is, however, assumed that EC-SOD variants of the invention may be employed for the same purposes and, as has been indicated above, with greater efficiency due to its particular properties which may make it especially attractive to employ EC-SOD variants of the invention extracellularly.

Recombinant EC-SOD C has been found to be more efficient than CuZn SOD in disease models in which the two SODs have been tested in parallel. Thus, as described by Johansson et al., Cardiovascular Research 24, 1990, pp. 500-503, recombinant EC-SOD C has been shown to reduce the concentration of oxygen-free radicals in reperfused rat hearts. The effect of rEC-SOD C in reducing the free radical concentrations was concluded to be at least of the same extent as CuZn SOD. Furthermore, recombinant human EC-SOD C has been shown to reduce myocardial damage in rats subjected to ischemia and 24 hours of reperfusion (G. Wahlund et al., J. Mol. Cell. Cardiol. 22, Suppl. 1 III, 1990, p. 47). In contrast, CuZn SOD did not show a significant induction of myocardial damage 24 hours after onset of reperfusion. M. Erlansson et al., Free Rad. Biol. Med., in press 1990 discloses the use of EC-SOD C and bovine CuZn SOD as an inhibitor of post-ischemic microvascular permeability increase in hamsters.

The present invention further relates to a pharmaceutical composition which comprises a polypeptide of the invention having the superoxide dismutating property of native EC-SOD and a modified affinity for heparin compared with recombinant EC-SOD C together with a pharmaceutically acceptable excipient, diluent or vehicle. The polypeptide of the invention incorporated in the composition may be from any of the sources discussed above, i.e. of recombinant, cell line or tissue origin.

The estimate of a suitable, i.e. therapeutically active, dosage for systemic treatment is made on the basis of the content of EC-SOD in the human body. EC-SOD is the major SOD in human plasma, and the total activity (composed of fractions A, B, and C; K. Karlsson et al., Biochem. J. 242, 1987, pp. 55-59) is about 20 U/ml. Injection of 200 IU heparin per kg body weight results in an increase of EC-SOD fraction C of about 23 U/ml (K. Karlsson et al., Biochem. J. 242, 1987, pp. 55-59). Although this heparin dosage is very high, a maximum release was apparently not achieved. In the pig in which a maximal EC-SOD C release could be obtained with a very high heparin dose, 200 IU heparin per kg body weight resulted in a 50% of that maximal EC-SOD C release (K. Karlsson et al., Biochim. Biophys. Acta 967, 1988, pp. 110-114). Assumption of a similar dose-response relationship in man results in an estimate of total EC-SOD of about 66 U/ml plasma $(20+2\times23$ U/ml). The total plasma volume is about 4.7% of the body weight corresponding to about 3.3 l in a 70 kg person. 1 unit EC-SOD equals about 8.8 ng. The total amount of EC-SOD in the blood vessels (plasma and vessel endothelium) is therefore $3,300\times66\times8.8\times10^{-9}$ g=1.92 mg. A tenfold increase would require 19 mg and a 300-fold increase 575 mg EC-SOD C. A suitable dosage of polypeptide of the invention may therefore be in the range of about 15-600 mg/day, dependent, i.e. on the type and severity of the condition for which administration of EC-SOD is indicated. Injection of, for instance, 87 mg EC-SOD C (a 50-fold increase) would result in 26 µg/ml in plasma (disregarding endothelium binding). This or even lower concentrations show strong protective properties in in vitro experiments (with CuZn SOD) (cf. A. Baret, I. Emerit, Mutation Res. 121, 1983, pp. 293-297; K. Grankvist, S. Marklund, J. O. Sehlin, I. B. Täljedal, Biochem. J. 182, 1979, pp. 17-25).

The dosage and timing of polypeptide of the invention injections depends on the half-life of the enzyme in human blood vessels, which is not yet known. It may as in rabbits be about 15 h (K. Karlsson et al., J. Clin. Invest. 82, 1988, pp. 762-766). The half-life in humans is however probably longer. Assuming first-order kinetics and a half-life of 36 h, daily injections of 35 mg after an initial injection of 87 mg would therefore result in the same concentration as after the initial injection.

EC-SOD C (K. Karlsson et al., Biochem. J. 242, 1987, pp. 55-59) and a polypeptide of the invention having a slightly reduced affinity for heparin compared to the heparin affinity of recombinant EC-SOD C, e.g. the polypeptide T216 of the invention described herein (Examples 1, 2 and 4) can be mobilized from cell surfaces to plasma with heparin. Parenteral heparin, other sulphated glucosaminoglycans and other strongly negatively charged substances may be used to modulate the location of endogenous or injected EC-SOD C and a polypeptide of the invention, having slightly modified affinity for heparin compared to recombinant EC-SOD C. Localization to the plasma phase might be useful in certain pathological conditions.

Except for type C (K. Karlsson et al., Biochem. J. 242, 1987, pp. 55-59; K. Karlsson et al., Biochem. J. 255, 1988, pp. 223-228) the structure of EC-SOD of type A and of type B is unknown. As shown in the present application and as stated above, variations in heparin affinity can be induced by mutations in the carboxyterminal end of recombinant EC-SOD C. A minor truncation resulted in a polypeptide having a slightly reduced heparin affinity i.e. EC-SOD variant T216 of the invention and further minor truncation resulted surprisingly in loss of heparin affinity (A types). B-types could instead be constructed by means of making heteropolymers between a polypeptide having an affinity for heparin corresponding to the C-type affinity, a polypeptide having a slightly reduced affinity as compared with C-type affinity and a polypeptide which does not display heparin binding. Since the results now establish that the binding to heparin is dependent on the C-terminal end, it is contemplated that further variation (increase or decrease) of the heparin affinity can be brought about by exchanges (mutations) of amino acids or other changes in this region of EC-SOD.

The therapeutic usefulness of the polypeptides of the invention may vary according to the particular disease to be treated. When strong binding to cell-surfaces is advantageous EC-SOD C or the polypeptides of the invention with even stronger heparin affinity may be most useful, for example in transplantation of organs or if a polypeptide of the invention is to be injected into an inflamed organ.

In yet other conditions a more limited heparin affinity such as that of a polypeptide having a slightly reduced affinity e.g. the polypeptide of the invention, T216, described herein, may be advantageous. In a situation in which the time of reperfusion cannot be predicted precisely (e.g. thrombolysis of coronary artery or artery in other organs) a strong binder such as EC-SOD C injected before reperfusion would bind firmly to endothelium around the body and very little would be available to protect immediately the reperfused organ territory at reperfusion. A polypeptide having a slightly reduced affinity e.g. the polypeptide of the invention, T216, described herein, would in this situation exist in relatively high concentration in the plasma phase (Examples 4.1 and FIG. 13), but would still bind endothelium and is also likely to redistribute more rapidly between binding sites in organs. The work of (K. Karlsson et al., Biochem. J. 255, 1988, pp. 223–228), especially FIG. 3, suggests that only EC-SOD variants with a heparin affinity of a magnitude which results in elution from Heparin-Sepharose ® column at a NaCl concentration of 0.55M or higher (under the conditions stated in the Analytical Methods section below) will bind to endothelium in vivo. Such variants may be advantageous in conditions where some but variable degree of cell-surface binding is valuable.

Variants which apparently do not bind heparan sulfate in vivo, A and B-types, may finally be useful when a high SOD activity in plasma or the interstitial fluid phase is important.

For topical treatment, far less of a polypeptide composition of the invention as described above would probably be needed. At present, 4–8 mg of CuZn SOD are administered intraarticularly once a week for the treatment of arthritis. EC-SOD which has a far higher molecular weight is likely to remain in the joint for a longer period of time. A similar treatment protocol or possibly somewhat lower doses will probably be appropriate.

DESCRIPTION OF THE DRAWINGS

The invention is further described with reference to the drawings, in which

FIG. 1A, FIG. 1B and FIG. 1C show the cDNA sequence and deduced amino acid sequence of EC-SOD C which has been obtained as in WO 87/01387. In FIG. 1A, the introduced translational stop codons of the EC-SOD variants T209, T213, T215 and T216 are identified by asterisks. In FIG. 1B, the amino acids introduced by substitutions in the EC-SOD variants G1, SA216, SA219 and SA220 are identified. In FIG. 1C, the amino acid introduced by substitution and the introduced translational stop codon in the EC-SOD variant SAT216 are identified.

FIG. 3 shows the sequences of the oligonucleotides used to produce the EC-SOD variants T216, T215, T213, T209, SA216, SA219, SA220 and G1 by site-directed mutagenesis as explained in Example 1. Also shown are the sequences and the nucleotide positions of the corresponding parts of the EC-SOD C template. Stars indicate the introduced stop codons in oligonucleotides T216, T215, T213 and T209 and, in the case of SA216, SA219, SA220 and G1, the introduced codon for alanine and glutamine, respectively.

determined by ELISA as described below in the Analytical Methods section. The unbroken line represents absorbance at 280 nm (left abscissa). The dotted line represents the NaCl gradient (right abscissa).

Figure 8A:
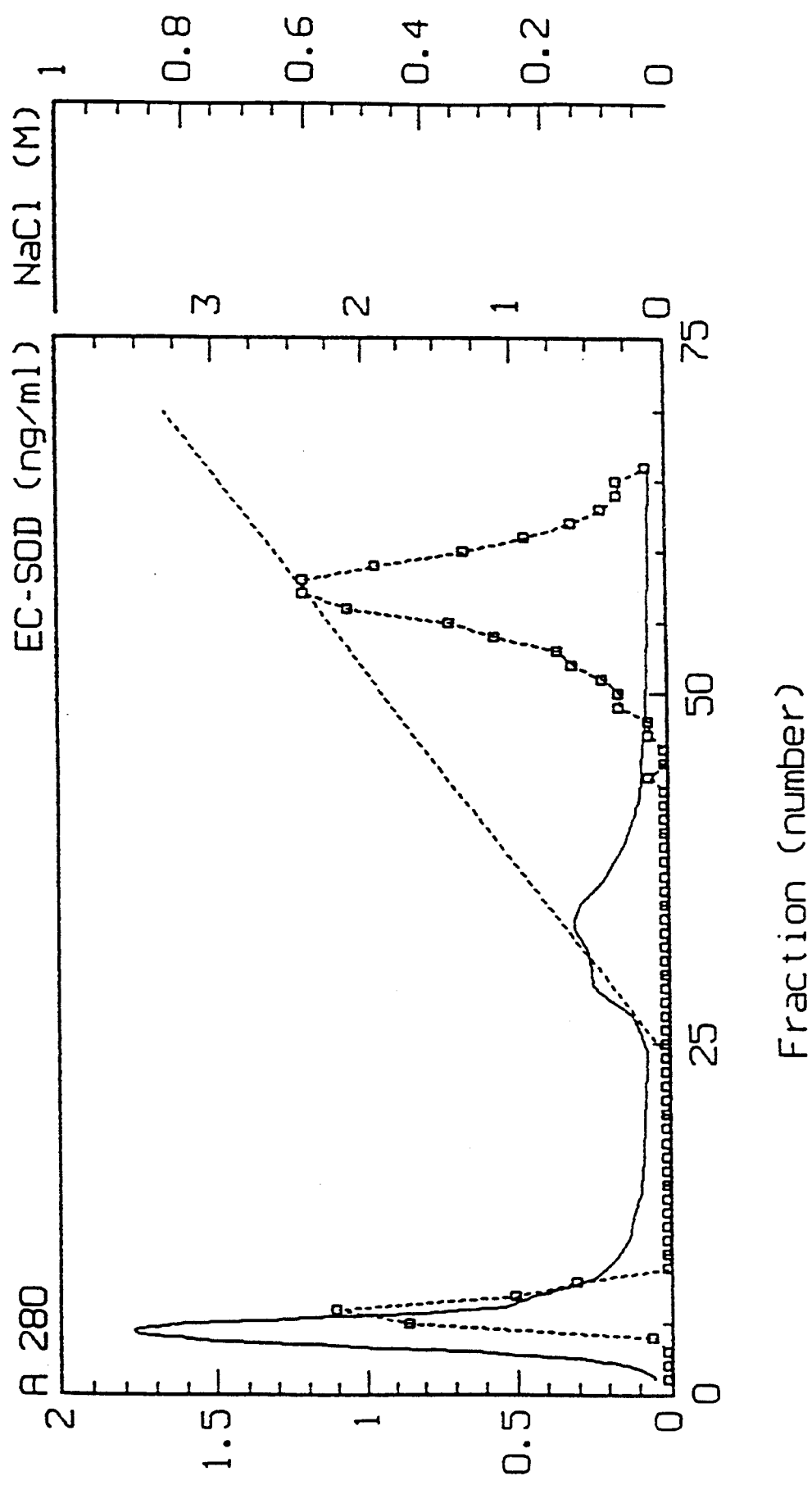
FIG. 8A is a graph showing the analytical separation of variant SA216 by Heparin-Sepharose ® chromatography. Culture medium of Example 2 containing variant SA216 was separated on Heparin-Sepharose ® as described below in the Analytical Methods section, and EC-SOD content (right abscissa) of the fractions (□) determined by ELISA as described below in the Analytical Methods section. The unbroken line represents absorbance at 280 nm (left abscissa). The dotted line represents the NaCl gradient (right abscissa).
Figure 8B:
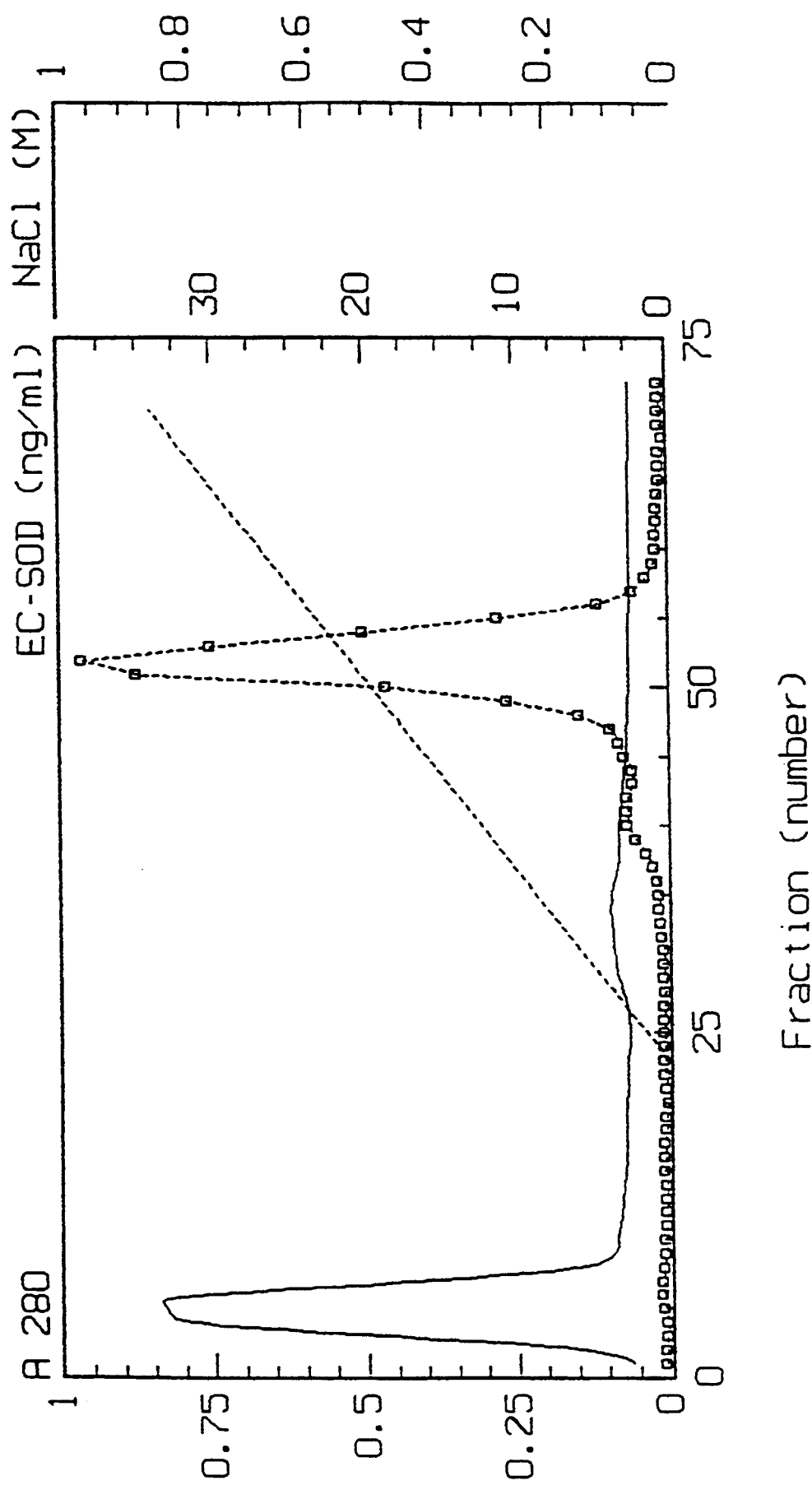
FIG. 8B is a graph showing the analytical separation of variant SA219 by Heparin-Sepharose ® chromatography. Culture medium of Example 2 containing variant SA219 was separated on Heparin-Sepharose ® as described below in the Analytical Methods section, and EC-SOD content (right abscissa) of the fractions (□) determined by ELISA as described below in the Analytical Methods section. The unbroken line represents absorbance at 280 nm (left abscissa). The dotted line represents the NaCl gradient (right abscissa).
Figure 8C:
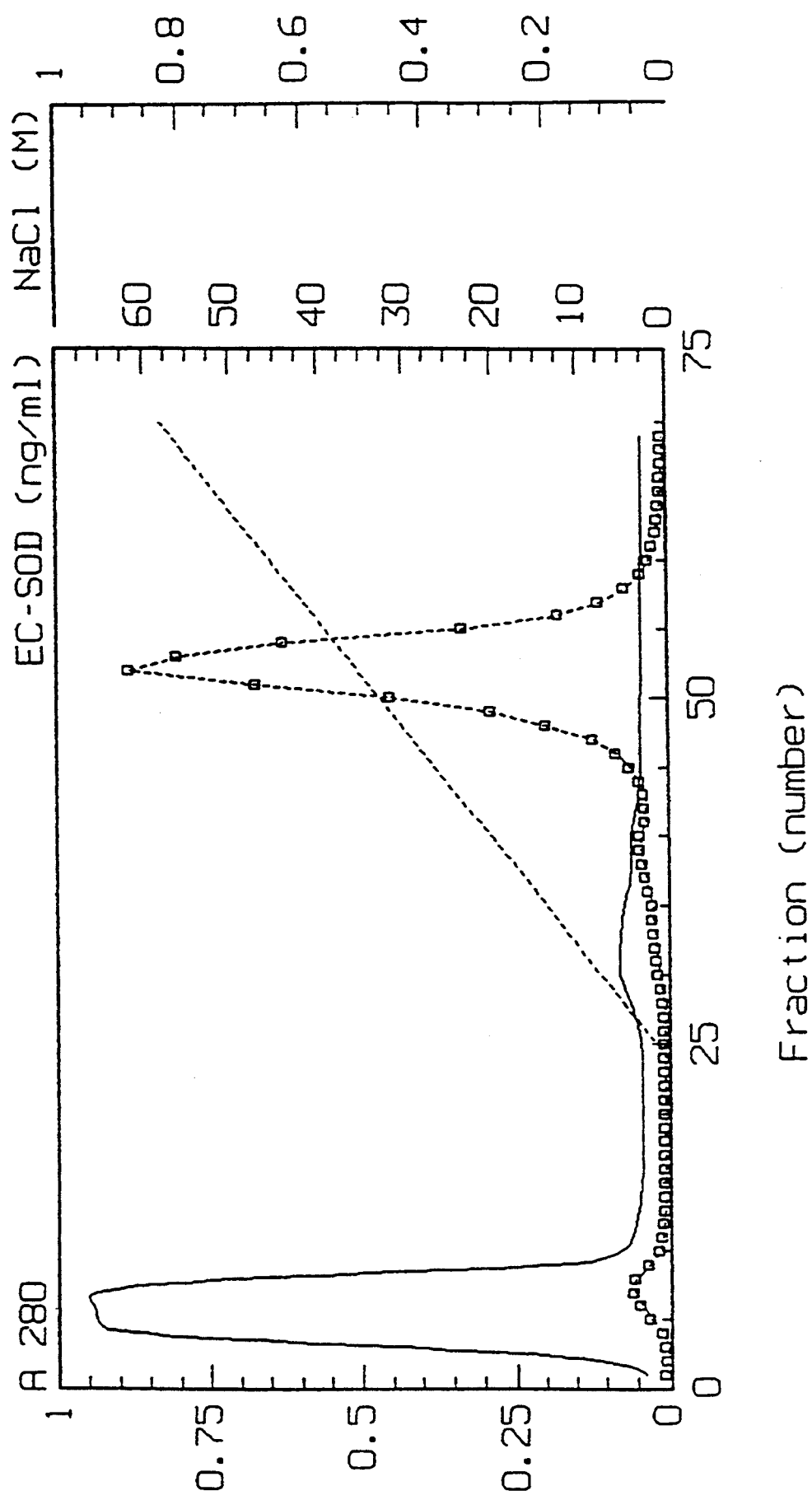
FIG. 8C is a graph showing the analytical separation of variant SA220 by Heparin-Sepharose ® chromatography. Culture medium of Example 2 containing variant SA220 was separated on Heparin-Sepharose ® as described below in the Analytical Methods section, and EC-SOD content (right abscissa) of the fractions (□)
Figure 8D:
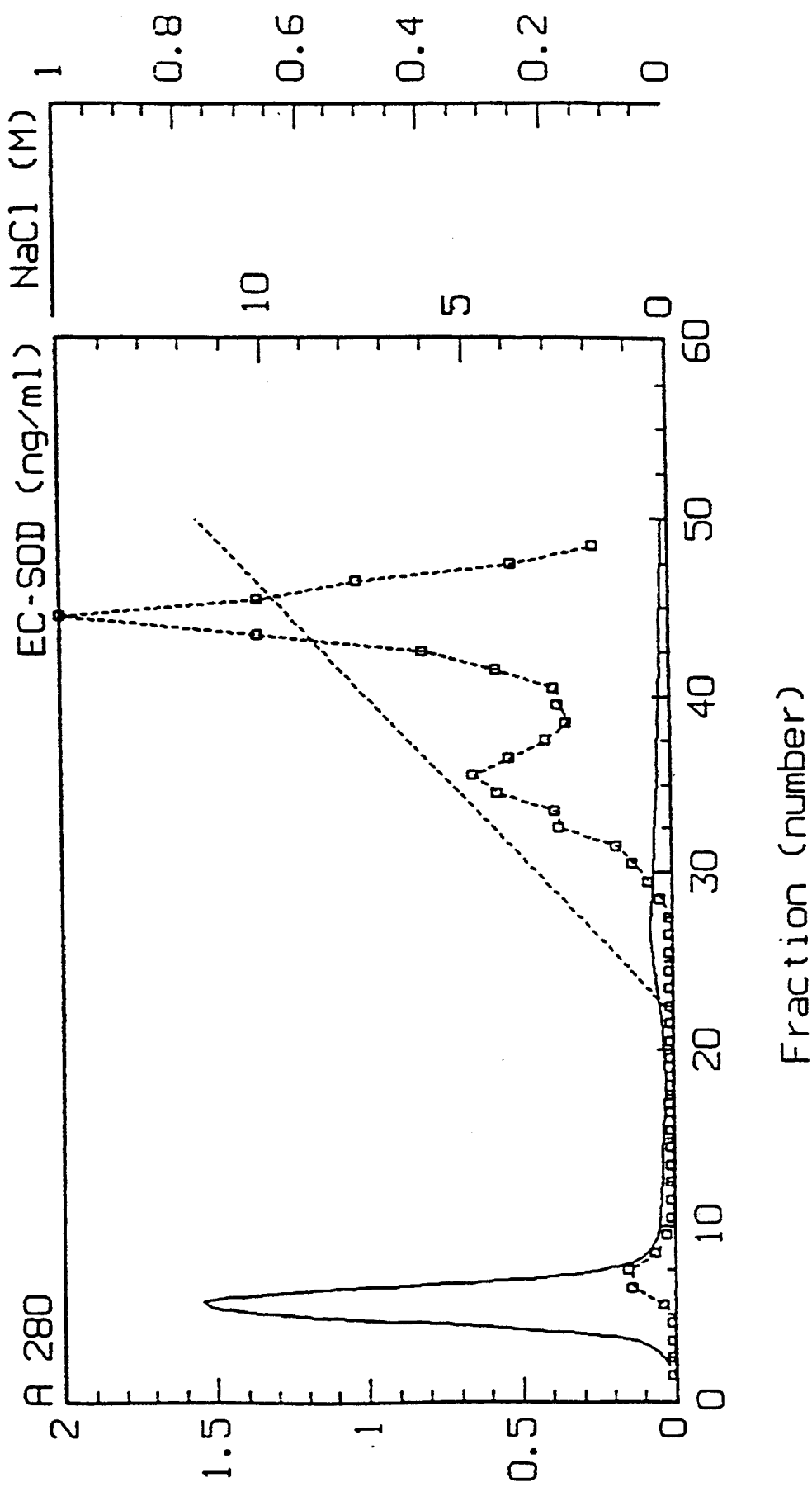
Figure 8:
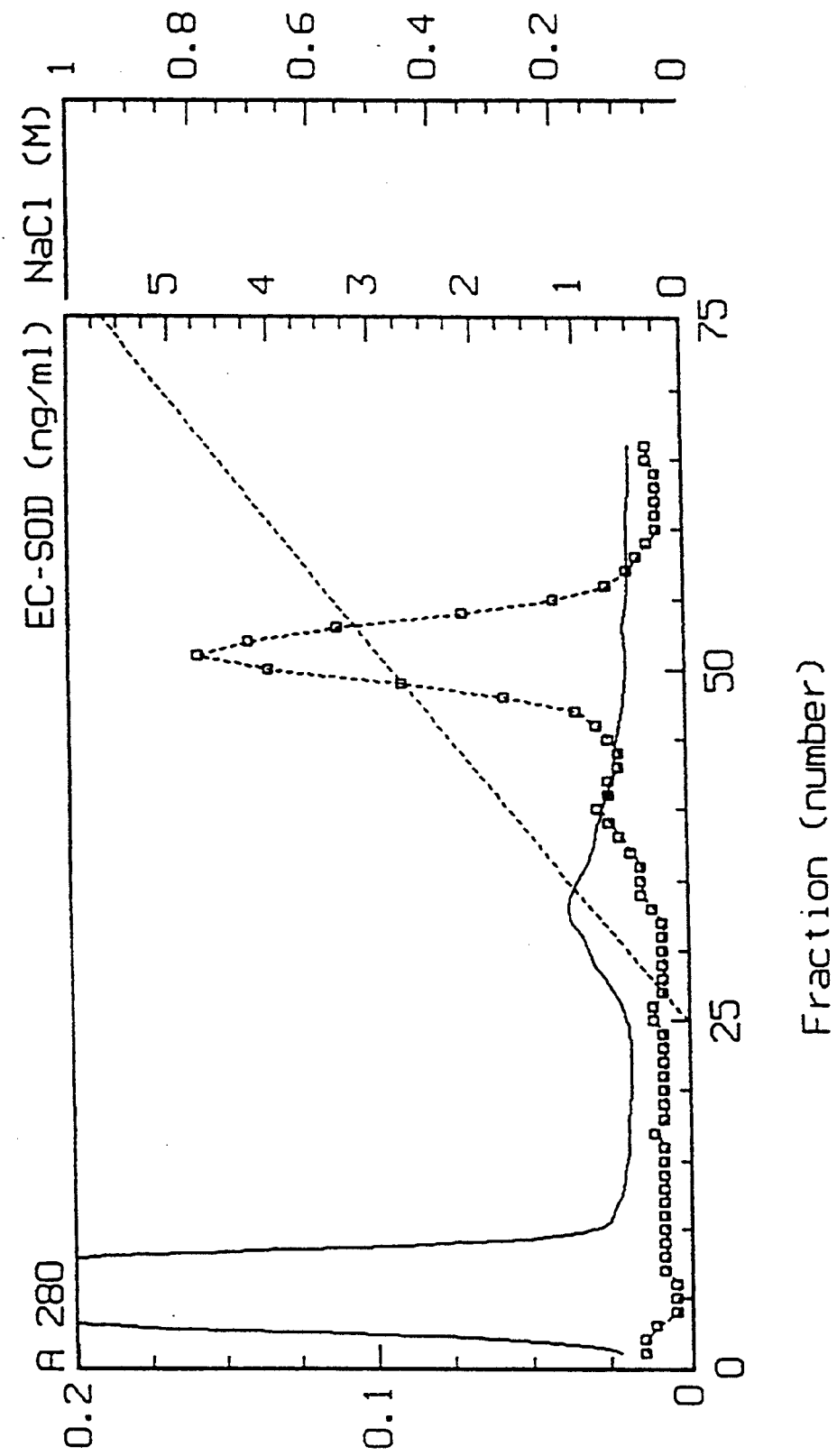

FIG. 8D is a graph showing the analytical separation of variant G1 by Heparin-Sepharose ® chromatography. Culture medium of Example 2 containing variant G1 was separated on Heparin-Sepharose ®, as described below in the Analytical Methods section, and EC-SOD content (right abscissa) of the fractions (□) determined by ELISA, as described below in the Analytical Methods section. The unbroken line represents absorbance at 280 nm (left abscissa). The dotted line represents the NaCl gradient (right abscissa).

FIG. 8E is a graph showing the analytical separation of variant SAT216 by Heparin-Sepharose ® chromatography. Culture medium of Example 2 containing variant SAT216 was separated on Heparin-Sepharose ® as described below in the Analytical Methods section, and EC-SOD content (right abscissa) of the fractions (□) determined by ELISA as described below in the Analytical Methods section. The unbroken line represents absorbance at 280 nm (left abscissa). The dotted line represents the NaCl gradient (right abscissa).

Figure 9:
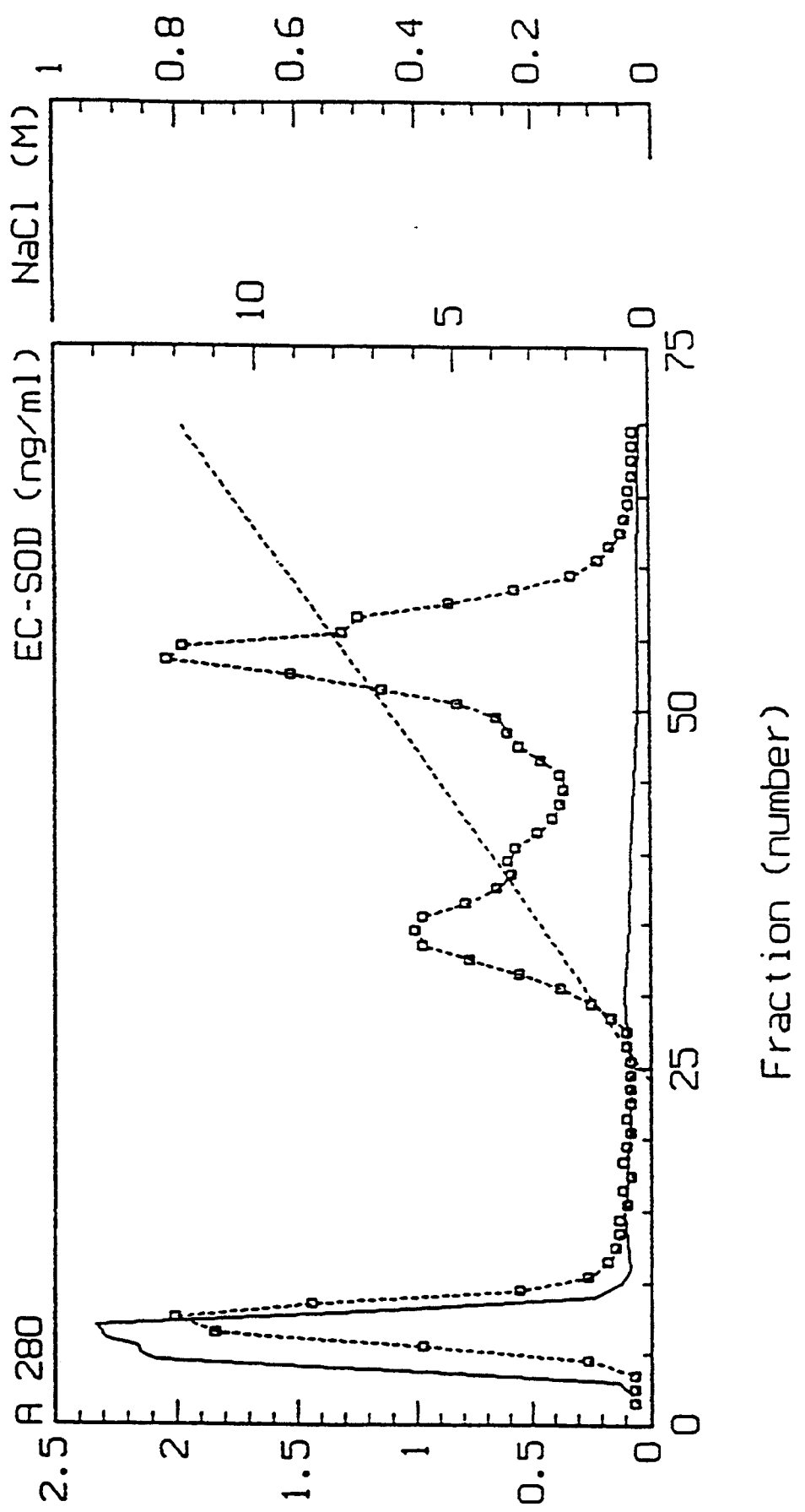

FIG. 9 is a graph showing the analytical separation by Heparin-Sepharose ® chromatography of EC-SOD variants obtained when plasmids pPS3 and pPST213 were cotransfected into CHO DXB11 cells. Culture medium of Example 2 containing the variants was separated on Heparin-Sepharose ®, as described below in the Analytical Methods section, and EC-SOD content (right abscissa) of the fractions (□) determined by ELISA, as described below in the Analytical Methods section. The unbroken line represents absorbance at 280 nm (left abscissa). The dotted line represents the NaCl gradient (right abscissa).

Figure 10:
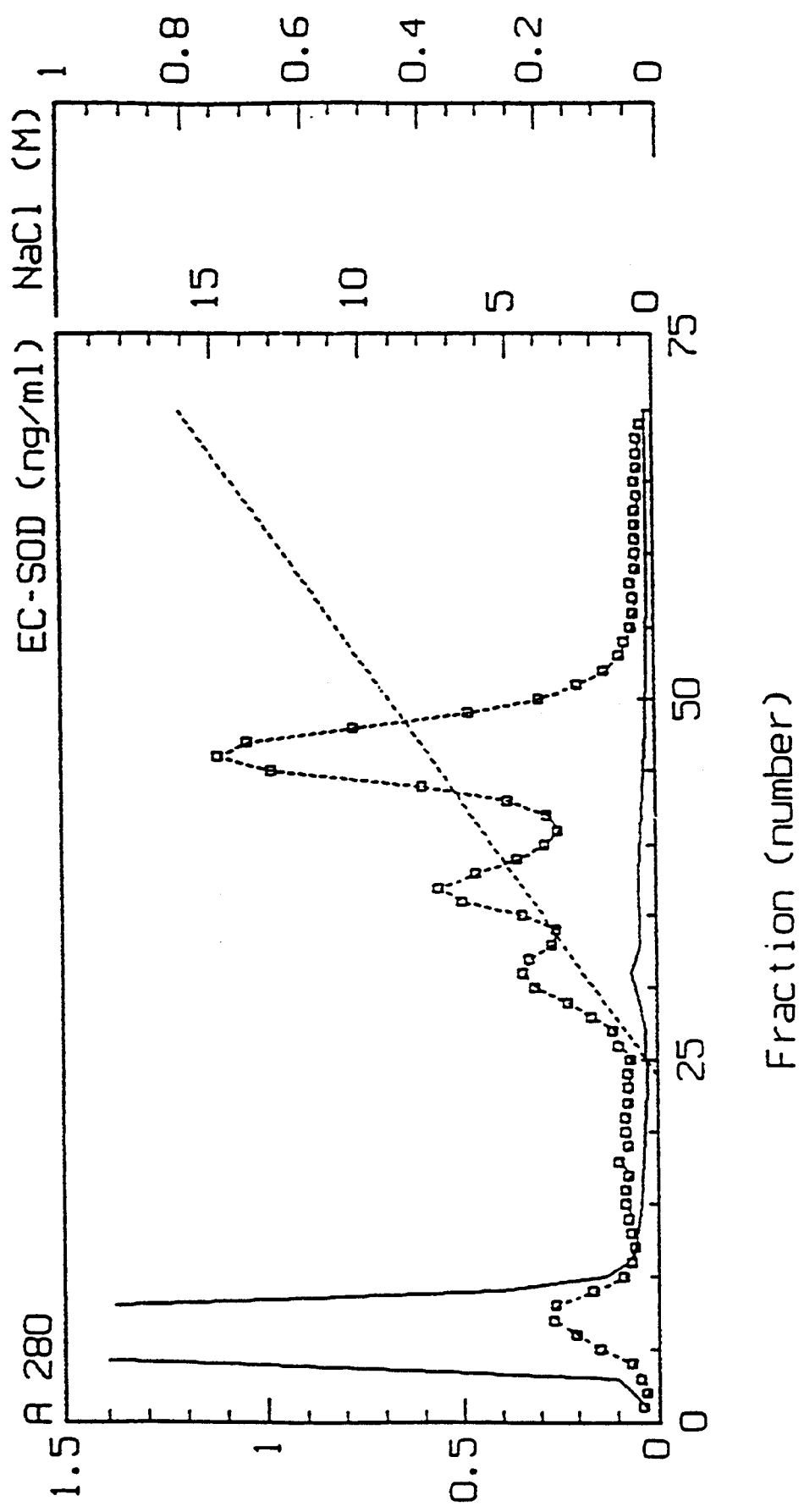

FIG. 10 is a graph showing the analytical separation by Heparin-Sepharose ® chromatography of EC-SOD variants obtained when plasmids pPST216 and pPST213 were cotransfected into CHO DXB11 cells. Culture medium of Example 2 containing the variants was separated on Heparin-Sepharose ®, as described below in the Analytical Methods section and EC-SOD content (right abscissa) of the fractions (□) determined by ELISA, as described below in the Analytical Methods section. The unbroken line represents absorbance at 280 nm (left abscissa). The dotted line represents the NaCl gradient (right abscissa).

Figure 11:
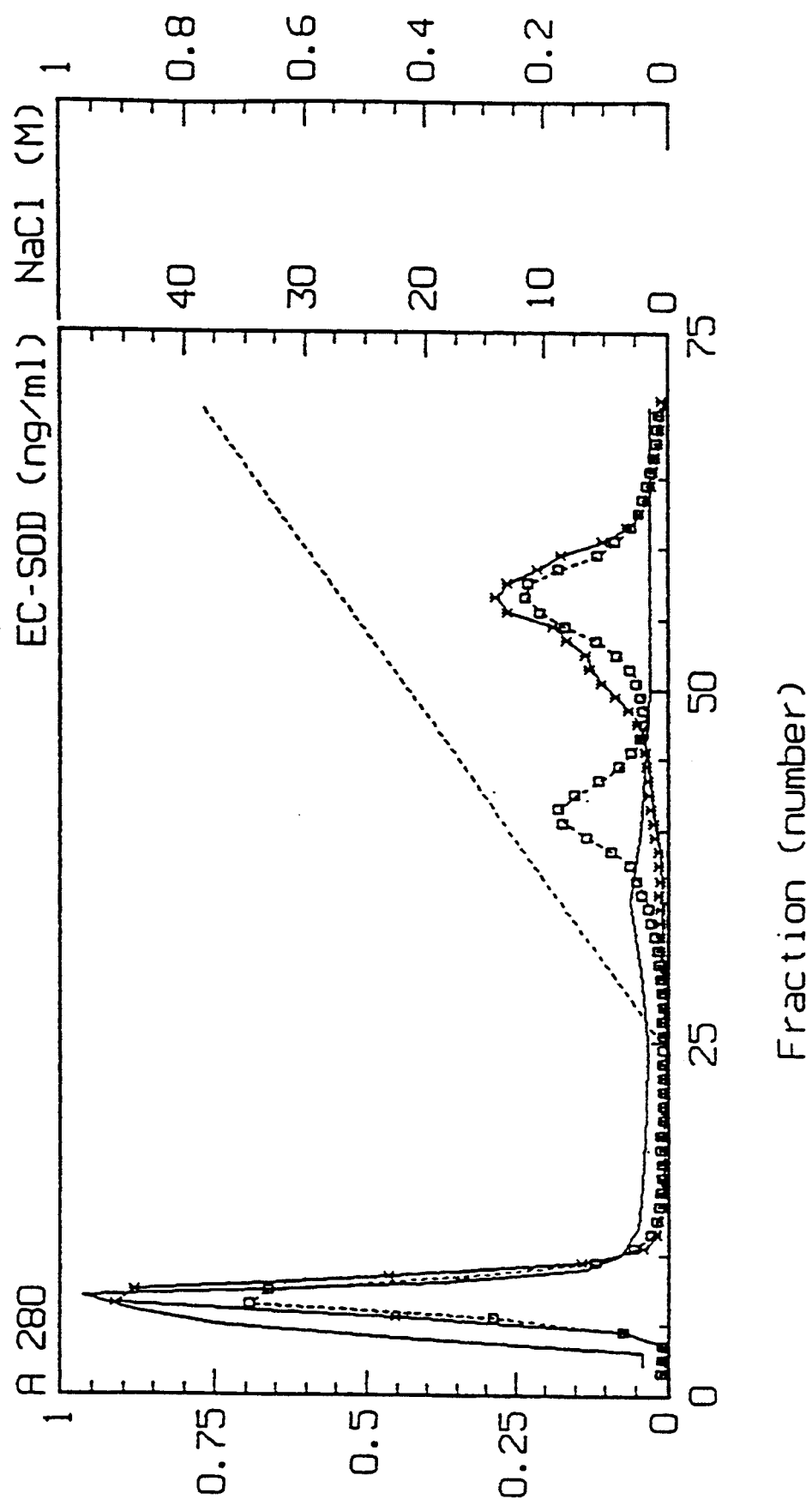

FIG. 11 is a graph showing the analytical separation by Heparin-Sepharose ® chromatography of EC-SOD variants obtained when recombinant EC-SOD C and variant T213 were coincubated for various times as described in Example 5.3. The culture medium containing the variants was separated on Heparin-Sepharose ®, as described below in the Analytical Methods section, and EC-SOD content (right abscissa) of the fractions determined by ELISA, as described below in the Analytical Methods section. The figure shows as examples the pattern obtained just after mixing (*) and after 23 hrs of incubation (□). The unbroken line represents absorbance at 280 nm (left abscissa) and the dotted line represents the NaCl gradient (right abscissa).

Figure 12:
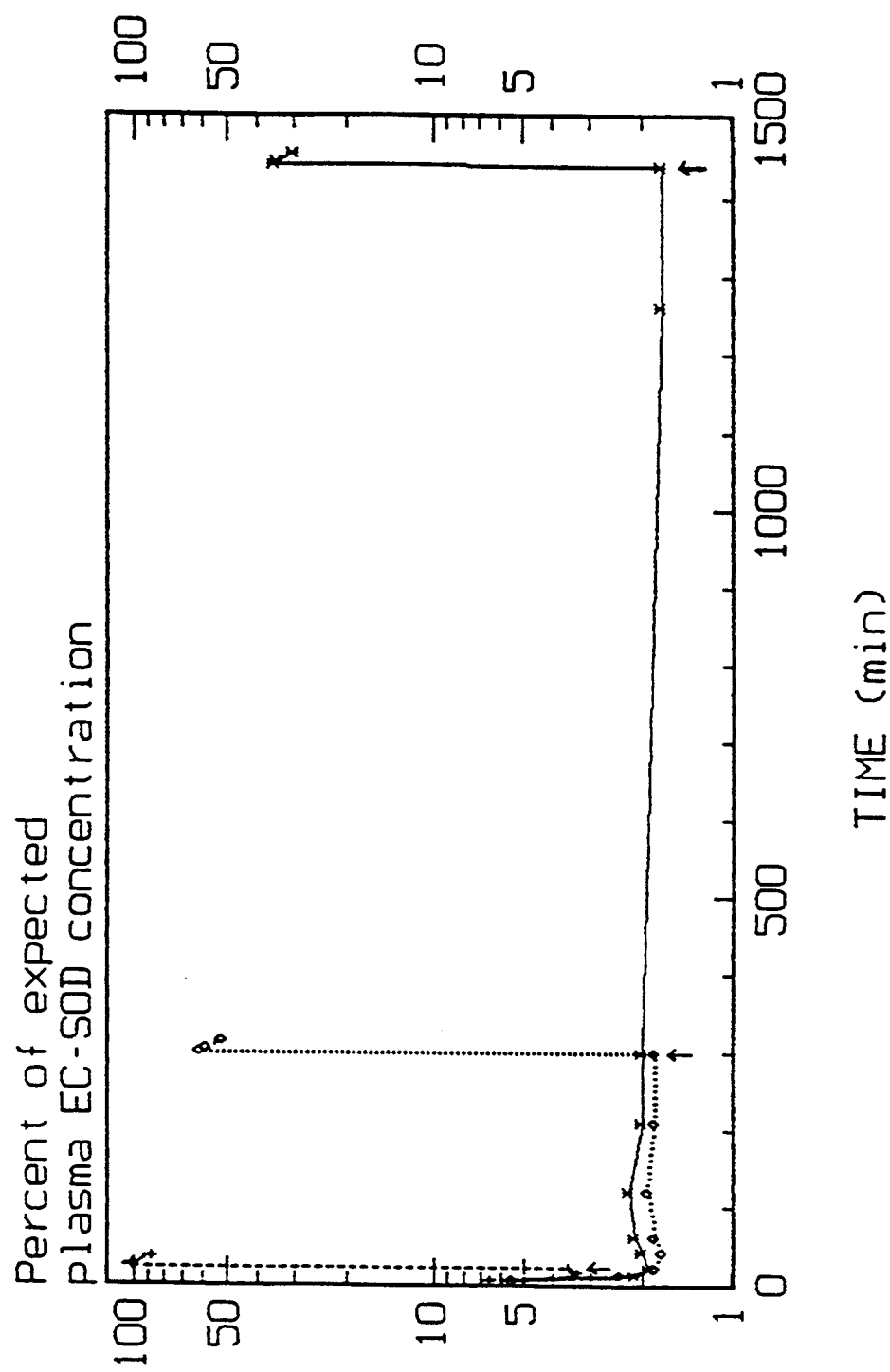

FIG. 12 is a graph showing plasma content of recombinant EC-SOD C following its intravenous bolus injection in rabbits. About 500 μg/kg body weight pure recombinant EC-SOD C (K. Hjalmarsson et al., Proc. Natl. Acad. Sci. USA. 84, 1987, pp. 6340–6344) was injected into three rabbits as described in Example 3 and blood samples drawn at the times indicated for analysis of EC-SOD content. In addition, at 20 minutes, 300 minutes and 24 hours following recombinant EC-SOD C administration, heparin 2,500 IU/kg body weight was injected intravenously (indicated by arrows) and plasma EC-SOD determined at short intervals thereafter. Each symbol represents one individual rabbit.

Figure 13:
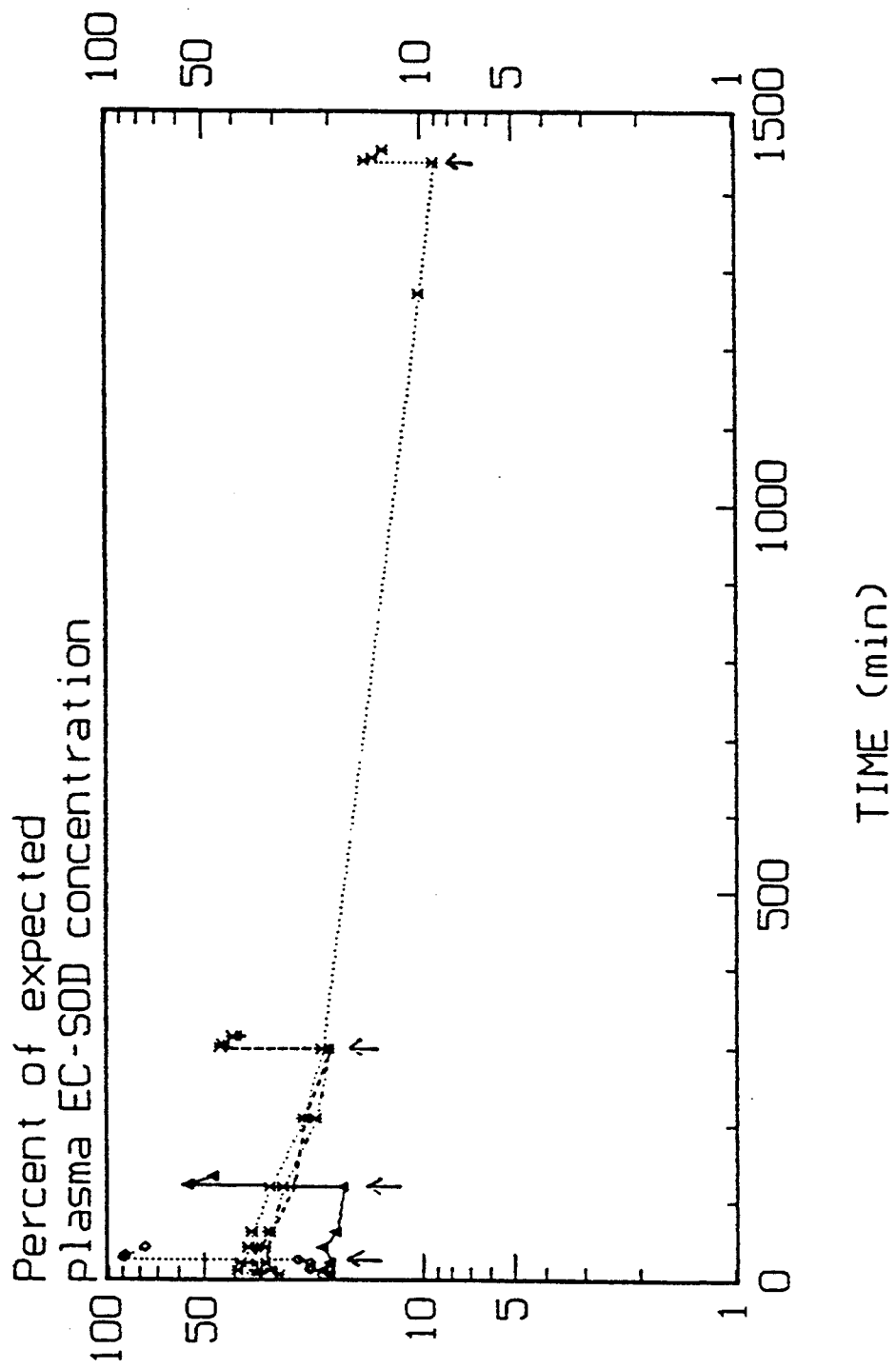

FIG. 13 is a graph showing plasma content of variant T216 following its intravenous bolus injection in rabbits. About 15 to 20 μg/kg body weight of variant T216 was injected into 5 rabbits as described in Example 4.1. The variant T216 employed was partially purified by means of Q-Sepharose ®, Phenyl-Sepharose ® and Heparin-Sepharose ® as described in Example 6. Blood samples were drawn at the times indicated for analysis of EC-SOD content. In addition, at 25 minutes, 120 minutes, 300 minutes and 24 hours following administration of variant T216, heparin 2,500 IE/kg body weight was injected intravenously (indicated by arrows) and plasma EC-SOD determined at short intervals thereafter. Each symbol represents one individual rabbit.

Figure 14:
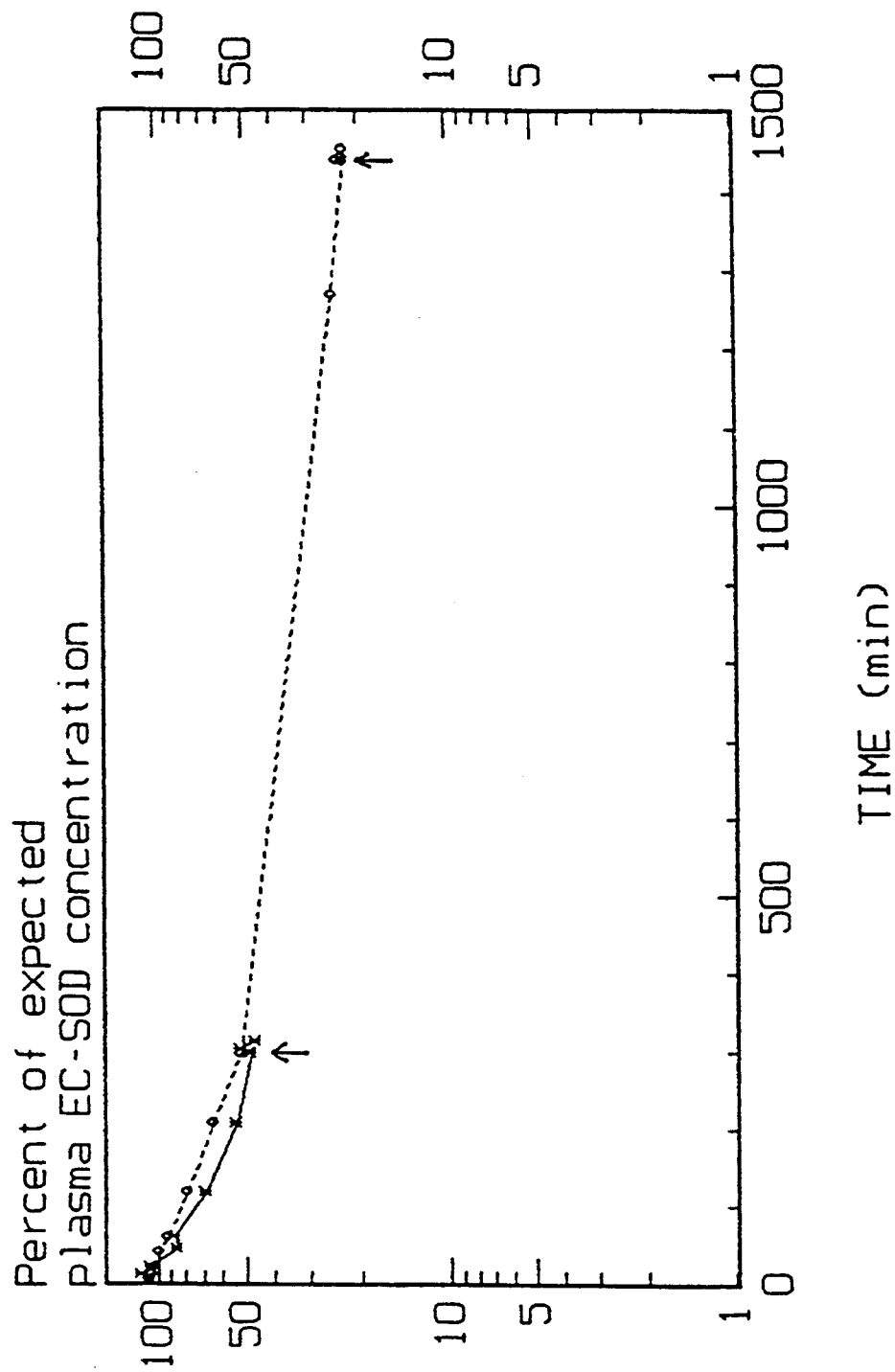

FIG. 14 is a graph showing plasma content of variant T213 following its intravenous bolus injection in rabbits. About 20 μg/kg body weight of variant T213 was injected into 2 rabbits as described in Example 4.3. The variant T213 employed was partially purified by means of CNBr-activated-Sepharose ®, Q-Sepharose ®, and Heparin-Sepharose ®, as described in Example 8. Blood samples were drawn at the times indicated for analysis of EC-SOD content. In addition, at 300 minutes and 24 hours following administration of variant T213, heparin 2,500 IE/kg body weight was injected intravenously (indicated by arrows) and plasma EC-SOD determined at short intervals thereafter. Each symbol represents one individual rabbit.

Figure 15:
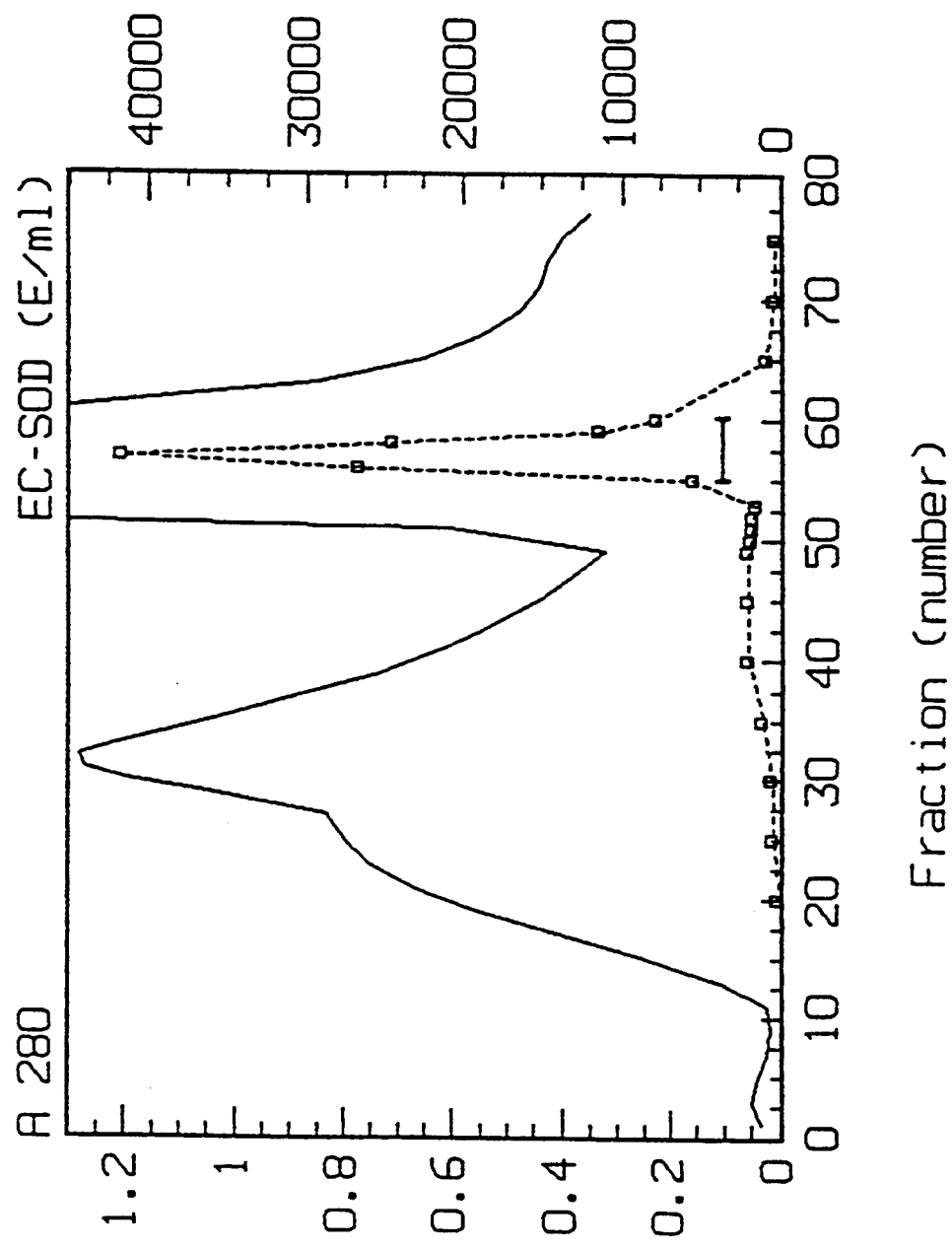

FIG. 15 is a graph showing the separation of variant T216 on Q-Sepharose ®. Culture medium containing variant T216 was applied to a Q-Sepharose ® column, as described in Example 6.1. EC-SOD content (right abscissa) of the fractions (□) was determined by ELISA, as described below in the Analytical Methods section. The unbroken line represents absorbance at 280 nm (left abscissa). The activity was pooled as indicated in the figure.

Figure 16:
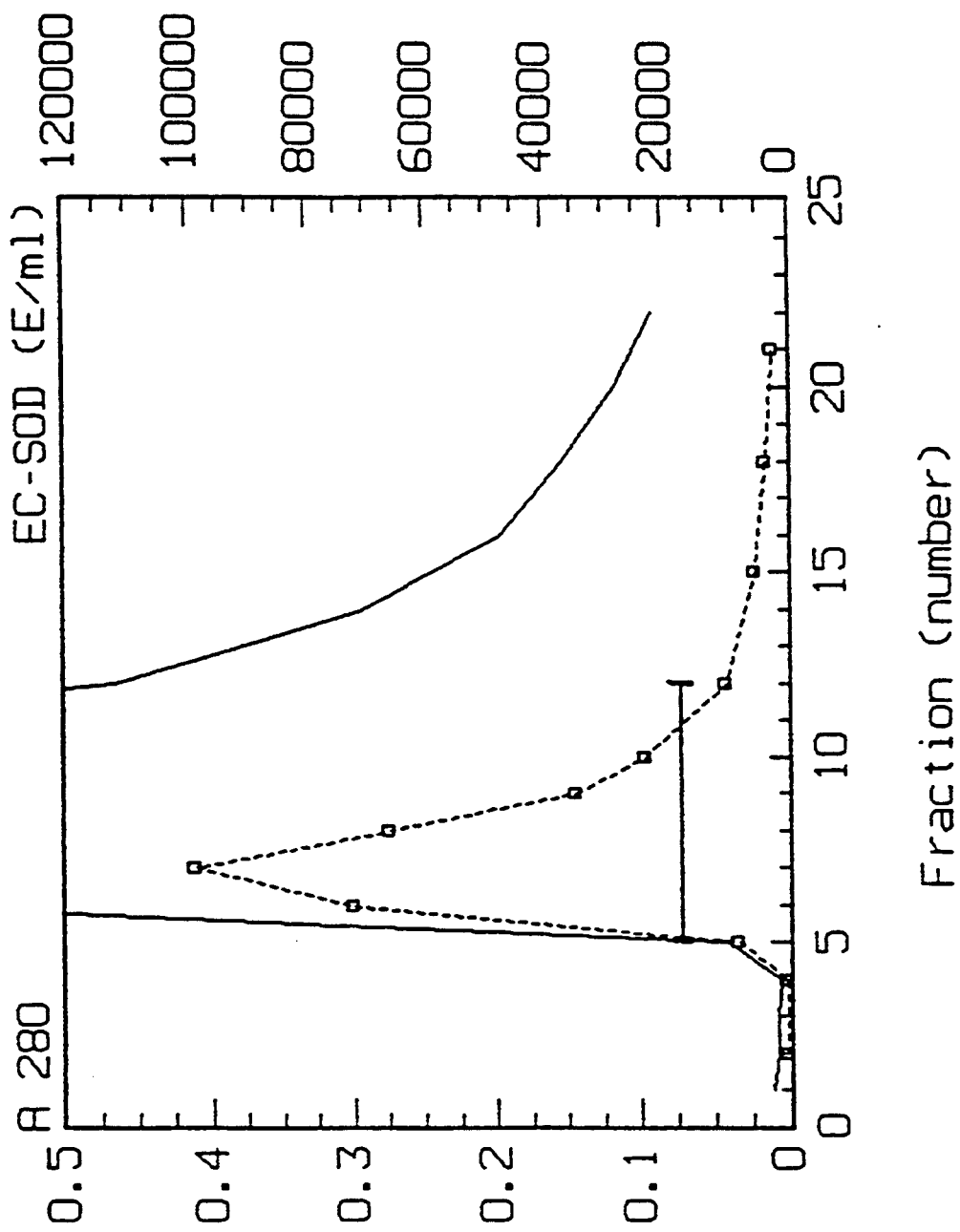

FIG. 16 is a graph showing the separation of variant T216 on Phenyl-Sepharose ®. The pool from the Q-Sepharose ® separation step (FIG. 15) was applied to a Phenyl-Sepharose ® column, as described in Example 6.2. EC-SOD content (right abscissa) of the fractions (□) was determined by ELISA, as described below in the Analytical Methods section. The unbroken line represents absorbance at 280 nm (left abscissa). The activity was pooled as indicated in the figure.

Figure 17:
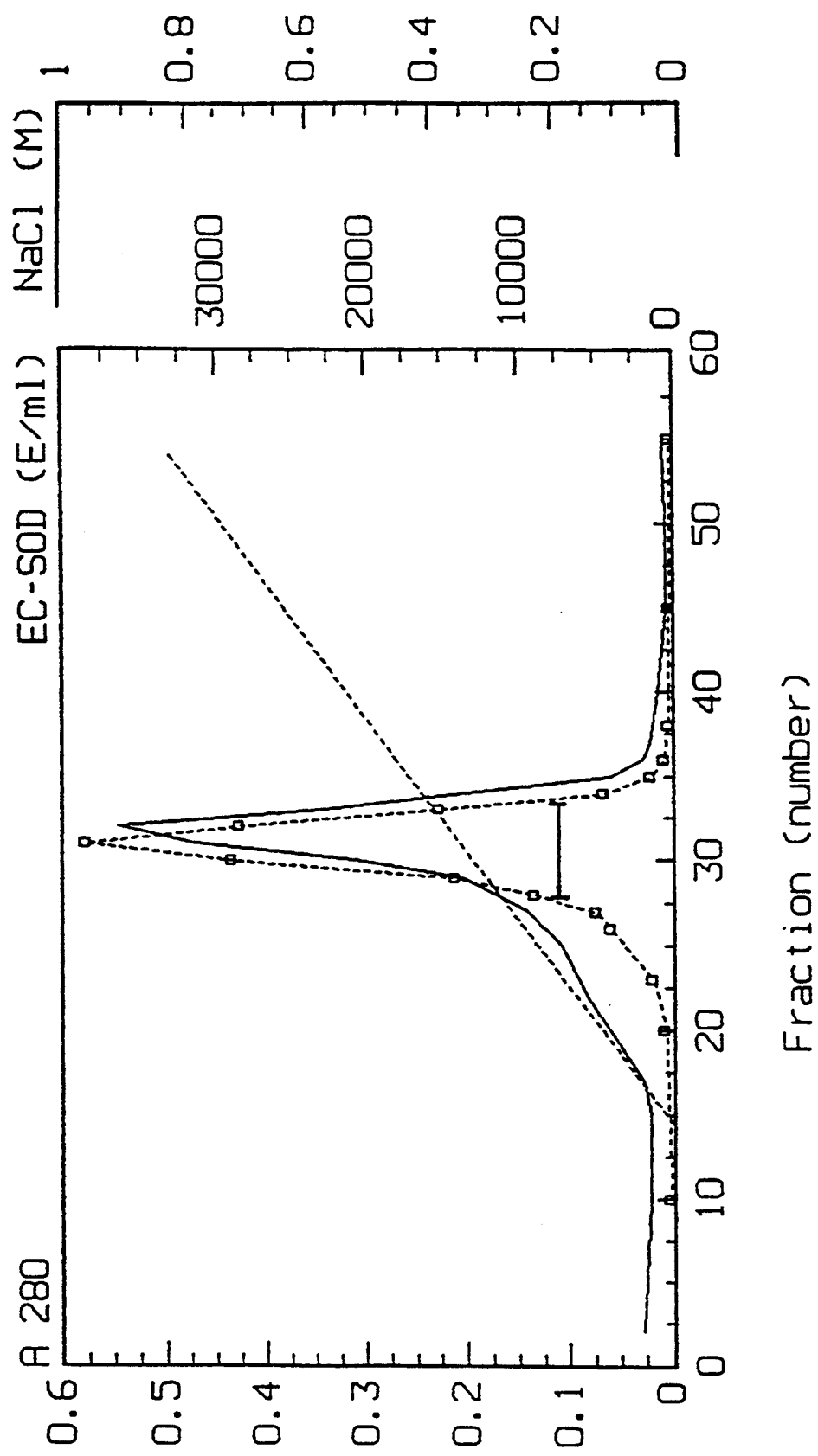

FIG. 17 is a graph showing the separation of variant T216 on Heparin-Sepharose ®. The pool from the Phenyl-Sepharose ® separation step (FIG. 16) was applied to a Heparin-Sepharose ® column, as described in Example 6.3. EC-SOD content (right abscissa) of the fractions (□) was determined by ELISA, as described below in the Analytical Methods section. The unbroken line represents absorbance at 280 nm (left abscissa). The dotted line represents the NaCl gradient (right abscissa). The activity was pooled as indicated in the figure.

Figure 18:

FIG. 18 is a photograph showing the electrophoresis of recombinant EC-SOD, variant T216 and variant T213 in a polyacrylamide gel, as described below in Examples 7 & 8. The samples were denatured (10 minutes, 100° C.) in solution containing sodium dodecylsulfate and 2mercaptoethanol. About 1 μg of each enzyme was applied to a gradient (10 to 17.5%) polyacrylamide gel equilibrated with sodium dodecylsulfate. The gel was stained with Coomassie Brilliant Blue. A crude Bovine Serum Albumin preparation was added to recombinant EC-SOD C and variant T213.

Lane A Molecular weight standards (Phosphorylase b, 94 kDa; Bovine Serum Albumin, 67 kDa; Ovalbumin, 43 kDa: Carbonic Anhydrase, 30 kDa; Soybean Trypsin Inhibitor, 20 kDa
Lane B Recombinant EC-SOD C
Lane C Variant T216
Lane D Variant T213

Figure 19:

FIG. 19 is a photograph showing Western blot of recombinant EC-SOD C, variant T216 and variant T213. The samples were first electrophoresed on a gradient (10 to 17.5%) polyacrylamide gel as described in the legend to FIG. 18, except that only 25–50 ng of each enzyme was applied. The gel was then blotted onto a Immobilon PVDF transfer membrane using a Bio-Rad Electroblotter. The membrane was saturated for 1 hour at 37° C. with a blocking buffer containing 5% non fatty milk. The membrane was then incubated for 2 hours with a polyclonal rabbit anti-human EC-SOD antibody (6.6 μg/ml) in buffer containing 2.5% non fatty milk. Then, the membrane was incubated with an alkaline phosphatase-conjugated porcine anti-rabbit antibody (Dakopatts D-306) in buffer containing 25% non fatty milk. The gel was finally developed in solution containing 0.34 mg/ml nitroblue tetrazolium, 0.315% dimethylformamide, and 0.175 ng/ml 5-bromo-4-chloro-3-indolyl phosphate, toluidinium salt).

Lane A 25 ng of recombinant EC-SOD C;
Lane B 25 ng of variant T216;
Lane C 25 ng of variant T213;
Lane D 50 ng of recombinant EC-SOD C;
Lane E 50 ng of variant T216; and
Lane F 50 ng of variant T213.

Figure 20:
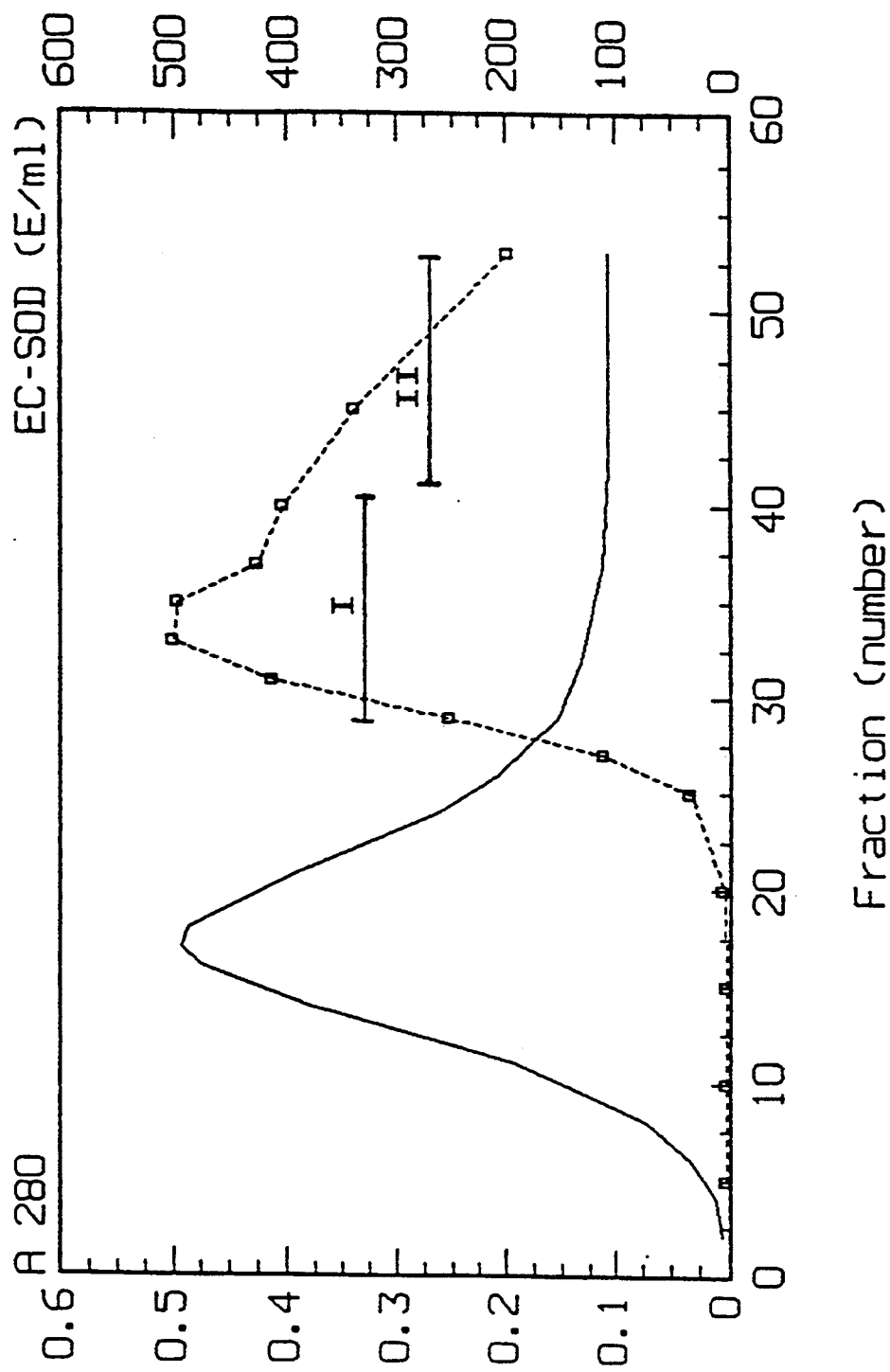

FIG. 20 is a graph showing the separation of variant T213 on Q-Sepharose ®. The variant T213 preparation, previously passed through an Anti EC-SOD-Sepharose ® column, was applied to a Q-Sepharose ® column, as described in Example 8.1. EC-SOD content (right abscissa) of the fractions (□) was determined by ELISA, as described below in the Analytical Methods section. The unbroken line represents absorbance at 280 nm (left abscissa). The activity was pooled as indicated in the figure.

MATERIAL AND METHODS USED IN THE EXAMPLES

Material

All chemicals (NaCl, $H_2O_2$, $Na_2CO_3$, $H_2SO_4$, potassium phosphate, sodium citrate, sodium phosphate, sodium cacodylate buffer, sodium dodecylsulfate, O-phenylenediamine, 1-aminoethylpropanol hydrochloride and EDTA) were of analytical grade.

Restriction enzymes were supplied from Boehringer Mannheim GmbH and used in accordance with the manufacturer's instructions.

Analytical Methods Applied to EC-SOD Variants

Analytical separation of EC-SOD variants from cell culture media on Heparin-Sepharose ®.

The EC-SOD variants were separated by Heparin-Sepharose ® chromatography using a Pharmacia FPLC apparatus, at room temperature. The columns contained 1 ml Heparin-Sepharose ® (Pharmacia Laboratory Separation Division, Uppsala, Sweden) with 15 mM Na cacodylate/50 mM NaCl, pH 6.50, as equilibration buffer and eluent. The absorbance at 280 nm was monitored on the eluent. The samples were applied at 5 ml per hour and when the absorbance at 280 nm approached the baseline, bound components were eluted with a linear gradient of NaCl in the buffer (0–1 mol/l) at 9 ml/h. The effluent was collected in 0.65 ml fractions and EC-SOD determined by enzyme-linked immunosorbent assay (ELISA), which method is described below. The chloride content of EC-SOD was determined using a standard chloride titrator (American Instrument Co, Inc, Md, USA).

Before application the solvents of the culture media were exchanged to 15 mM sodium cacodylate/50 mM NaCl, pH 6.50, on a Filtron Omega cell membrane concentration system. In general 1–2 ml of culture medium was applied to the Heparin-Sepharose ® column.

Enzyme-linked immunosorbent assay (ELISA) for human EC-SOD

Quantitation of human EC-SOD was made using the double antibody sandwich ELISA method. Microtiter plates (Nunclon; Nunc, Roskilde, Denmark) were coated with 100 μl per well of a solution containing 16 μg/ml of polyclonal rabbit anti-EC-SOD IgG antibodies in 50 mM $Na_2CO_3$, pH 9.6. After 2 h incubation at room temperature, the wells were washed with blocking buffer (10 mM Na phosphate, pH 7.4, 140 mM NaCl, 0.1% wt/vol Tween 20, and 0.5% BSA) and then blocked overnight with 300 μl blocking buffer. For analysis, 50-μl samples, diluted if necessary with blocking buffer, were added to each well and incubated for 2 h. The wells were then washed with blocking buffer, and 50 μl 3 μg/ml monoclonal anti-EC-SOD antibody B6,H6 which is described in, and produced according to, Example 15 of WO 87/01387 and 50 μl peroxidase-conjugated rabbit anti-mouse IgG (DAKOPATTS, Copenhagen, Denmark), both dissolved in blocking buffer, added in that order. After a further 2 h, the wells were washed with blocking buffer and then developed for 10 min with 100 μl 3.7 mM O-phenylenediamine and 0.4 mM $H_2O_2$ in 100 mM Na citrate, pH 5.0. After addition of 100 μl 0.5M $H_2SO_4$, the absorbance at 492 nm was determined in an ELISA processor II (Hoechst Behring, Marburg, FRG). The assay was standardized with human umbilical cord EC-SOD C. EC-SOD concentrations down to ~0.25 ng/ml could be determined.

Determination of apparent molecular weights of EC-SOD variants by means of gel chromatography Apparent molecular weight of EC-SOD variants was determined by gel chromatography, at 4° C. using a LKB HPLC apparatus (Pharmacia LKB Biotechnology Inc.). Culture media (1–3 ml) containing human EC-SOD variants were applied to a Sepharyl S-300 column (Pharmacia LKB Biotechnology Inc.) (1.6×89 cm), equilibrated and eluted with 10 mM potassium phosphate, pH 7.4, containing 0.15M NaCl, at a flow rate of 19.8 ml per hour. The effluent was collected in 1.35 ml fractions and the EC-SOD content determined by ELISA as described above. The column was calibrated with IgG (156 kDa) (Sigma Chemical Co., St. Louis, USA), bovine serum albumin (67 kDa) (Sigma Chemical Co., St. Louis, USA) and carbonic anhydrase (29 kDa) (Sigma Chemical Co., St. Louis, USA). The calibration curve was constructed by means of plotting the log molecular weights of the calibrators versus their elution volumes. Recombinant EC-SOD C and the variants T216 and T213 displayed apparent molecular weights of around 150 kDa. The glycosylation variant G1 eluted at a position corresponding to 95.5 kDa.

Analysis of superoxide dismutase activity

The superoxide dismutase activity of samples was determined by a direct spectrophotometric method employing $KO_2$ (S. Marklund, J. Biol. Chem. 251, 1976, pp. 7504–7507), as slightly modified in (S. Marklund, In: Handbook of Methods for Oxygen Radical Research, ed; R. Greenwald, CRC press, 1985, pp. 249–255). In brief, the basis of the method is that SOD is determined in terms of its ability to catalyze the disproportionation (decay) of $O_2.^-$ in alkaline aqueous solution. At alkaline pH and low $O_2^-$ concentration, the $O_2.^-$ radical is stable enough to be studied in common UV-vis spectrophotometers, using the broad absorbance maximum at 245–250 nm. Thus the assay was conducted at pH 9.5 and the disproportionation studied directly in a spectrophotometer. One unit in the assay is defined as the activity that brings about a disproportionation of $O_2.^-$ at a rate of 0.1 sec-1 in 3 ml of buffer. Under these conditions, one unit of enzyme corresponds to 8.6 ng native or recombinant human EC-SOD C (L. Tibell et al., Proc. Natl. Acad. Sci. USA. 84, 1987, pp. 6634–6638).

This assay is 40 times more sensitive (i.e. the units correspond to 40 times less enzyme) than the original xanthine oxidase - cytochrome C assay (J. M. McCord and I, Fridovich. J. Biol. Chem. 244, 1969, pp. 6049–6055).

EXAMPLE 1

Construction of novel EC-SOD variants by site-specific mutagenesis of human EC-SOD type C Nine novel EC-SOD variants were prepared by site-specific mutagenesis (vide infra) of the human EC-SOD cDNA encoding EC-SOD type C obtained from a human placenta cDNA library (K. Hjalmarsson et al., Proc. Natl. Acad. Sci. USA. 84, 1987, pp. 6340–6344). The nucleotide sequence of the cDNA encoding EC-SOD C is shown in FIG. 1. The general strategy employed for the construction of the novel EC-SOD variants was to create amino acid substitutions by mutation of specific codons, e.g. to mutate a potential glycosylation site, or to introduce translational stop codons at different positions in the cDNA or a combination thereof.

The oligonucleotide-directed in vitro mutagenesis was performed using a commercially available kit (Amersham, U.K.) and following the protocol outlined below and given in detail on pages 15–47 of the Amersham handbook "Oligonucleotide-directed in vitro mutagenesis system". This protocol, which is based on the methods of Eckstein et. al. (J. W Taylor et. al. Nucl. Acids Res. 13, 1985, pp. 8749–8764; J. W Taylor et. al. Nucl. Acids Res. 13, 1985, pp. 8764–8785; K. Nakamaye and F. Ekstein, Nucl. Acids Res. 14, 1986 pp. 9679–9698) has the advantage over other mutagenesis systems that it involves a strand-specific selection step which eliminates the unwanted non-mutant sequence in vivo, generating a pure homoduplex mutant DNA sequence. In brief, the mutagenic oligonucleotide sequence is annealed (70° C. for 3 min, 37° C. for 30 min) to the single-stranded template and extended (15 hrs at 16° C.) by Klenow polymerase (12 units) in the presence of T4 DNA ligase (12 units) to generate a mutant heteroduplex. Selective removal of the non-mutant strand is made possible by the incorporation of a thionucleotide into the mutant strand during in vitro synthesis. Digestion with restriction enzyme NciI (5 units, 37° C. for 90 min) presents sites for exonuclease III (50 units ExoIII, 37° C. for 30 min) to digest away all of the non-mutant strand of the cloned target sequence while leaving the mutant strand intact, thus enabling the mutant strand to repolymerize (3 units DNA Poll. 2 units T4 DNA ligase, 16° C. for 3 hrs) a homoduplex mutant DNA sequence. In applying the method in the present example, the 1396 bp long cDNA encoding human EC-SOD type C was cloned into the Eco R1 site of phage M13 mp8 (J Messing and J. Vieira, Gene 19, 1982, pp 269–276) and single stranded DNA template prepared in the conventional manner, as described in detail in the Amersham handbook, pp 26–27. The template was subsequently used together with variant oligonucleotides in the in vitro mutagenesis reaction which was carried in the manner mentioned above and described in detail in the Amersham handbook.

Nine different mutant oligonucleotides (21 to 23 nucleotides in length), as illustrated in FIG. 3, were used in nine different in vitro mutagenesis reactions to produce nine different EC-SOD variants. The mutations introduced are outlined below.

| Variant | Mutated codon | Mutated amino acid | Plasmid |
|---|---|---|---|
| T216 | 772 AGC → 772 TGA | 217 Ser → stop | pPST216 |
| T215 | 769 GAG → 769 TAG | 216 Glu → stop | pPST215 |
| T213 | 763 CGG → 763 TGA | 214 Arg → stop | pPST213 |
| T209 | 751 CGC → 751 TGA | 210 Arg → stop | pPST209 |
| SA216 | 769 GAG → 769 GCG | 216 Glu → Ala | pPSSA216 |
| SA219 | 778 TGC → 778 GCC | 219 Cys → Ala | pPSSA219 |
| SA220 | 781 AAG → 781 GCG | 220 Lys → Ala | pPSSA220 |
| SAT216 | 769 GAG → 769 GCG | 216 Glu → Ala and | |
|  | 772 AGC → 772 TGA | 217 Ser → stop | pPSSAT216 |
| G1 | 390 AAC → 390 CAA | 89 Asn → Gln | pPSG1 |

Figure 2:
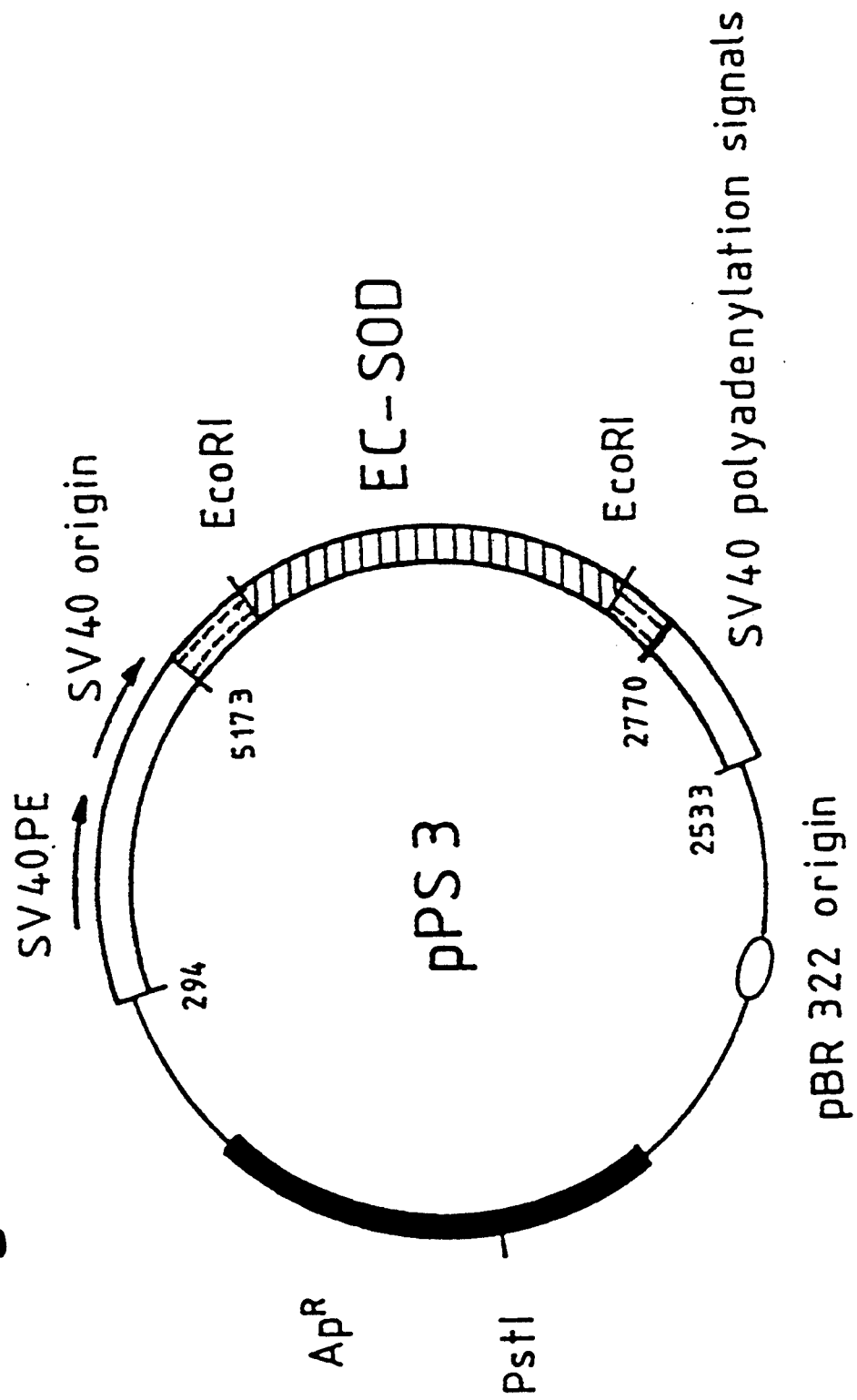
FIG. 2 shows the structure of plasmid pPS3 used for producing each of the EC-SOD variants T216, T215, T213, T209, SA216, SA219, SA220 and G1. The white areas represent SV40 DNA and the numbers refer to the corresponding nucleotide positions in SV40. SV40PE and SV40 origin represent the SV40 early promotor and the SV40 origin of replication, respectively, and arrows show the direction of transcription and DNA replication, respectively. SV40 polyadenylation signals are located between positions 2770 and 2533. The hatched area represents the DNA sequence encoding each of the EC-COD variants T216, T215, T213, T209 and G1, respectively. Dotted area represents polylinker DNA. The solid black area represents the β-lactamase gene (AP$^R$) of plasmid pBR322. Thin lines represent plasmid pBR322 DNA. Also indicated is the location of the pBR322 origin of replication.

The mutant progenies in these reactions were identified by DNA sequencing of single stranded DNA templates prepared from phages produced in these in vitro mutagenesis reactions using the dideoxy technique described in (P. H. Schreir and R. Cortese, J. Mol. Biol. 129, 1979, pp 169–172). On average one mutant progeny was identified out of six sequenced templates. Double stranded replicative forms of the mutated progenies were prepared as described in (M. Ausobel. Current Protocols in Molecular Biology, 1, 1987, 1.15.2), digested with Eco R1, and the different mutant cDNA fragments were isolated from agarose gels by electroelution, phenol and chloroform extraction and ethanol precipitation (Maniatis et al., Molecular Cloning, A Laboratory Manual, Cold Spring Harbor Laboratories, 1982). These mutant Eco R1 cDNA fragments were introduced into EcoR1 digested, alkaline phosphatase treated plasmid pPS3, the structure of which is shown in FIG. 2 (L. Tibell et al., Proc. Natl. Acad. Sci. USA. 84, 1987, pp. 6634–6638) by replacement of the wildtype cDNA Eco R1 fragment. The absence of the wildtype fragment and the presence of the mutant EC-SOD cDNA fragments was confirmed by DNA sequencing of the respective plasmid using double stranded DNA as template as described in (O. Karlsson, Proc. Natl. Acad. Sci. USA. 84, 1987, pp. 8819–8823).

Nine pPS3 derivatives were obtained which were denoted pPST216, pPST215, pPST213, pPST209, pPSSA216, pPSSA219, pPSSA220, pPSSAT216 and pPSG1, respectively, and which encode the variants T216, T215, T213, T209, SA216, SA219, SA220, SAT216 and G1, respectively. The nucleotide sequences for each of the variants appear from FIG. 1A–1C. Cell lines CHO DXB-11/pEE6-pSV2Ddhfr and CHO DXB-11/pEE7-pSV2dhfr harbouring plasmids pPST216 (pEE6) and pPST213 (pEE7), respectively, have been deposited on Sep. 14, 1989 in the European Collection of Animal Cell Cultures under the accession numbers ECACC 890914102 and ECACC 89091403, respectively, in accordance with the provisions of the Budapest Treaty.

In a similar manner to the one described above, i.e. using site-directed mutagenesis, other EC-SOD variants having a reduced affinity for heparin compared with native EC-SOD C may be prepared. Thus, it is contemplated that substitution of other positively charged amino acids besides Lys-220, especially one or more of the Lys and Arg in the C-terminal part of EC-SOD, with a neutral or negatively charged amino acid may result in a EC-SOD variant with a slightly reduced affinity for heparin compared to EC-SOD C, which variant has retained the superoxide dismutating property of native EC-SOD.

An EC-SOD variant having increased affinity for heparin compared to native EC-SOD C and having retained the superoxide dismutating property of native EC-SOD has been prepared by substituting the negatively charged amino acid Glu in position 216 with the neutral amino acid Ala (variant SA216). In a similar manner, other EC-SOD variants are contemplated, which variants may be prepared from native EC-SOD C by substitution of neutral and/or negatively charged amino acids in the C-terminal part of EC-SOD C with positively charged amino acids using site-directed mutagenesis in the same manner as described above. Furthermore, insertion of additional basic amino acids into the native C-terminal part of EC-SOD using synthetic DNA encoding combinations of the amino acids arginine, lysine and histidine by site-directed mutagenisis is contemplated to result in EC-SOD variants having increased affinity for heparin compared to native EC-SOD C and having the superoxide dismutating property of native EC-SOD.

EXAMPLE 2

Expression of EC-SOD variants in CHO cells 2.1. 20 μg of the nine pPS3 derivatives constructed in Example 1, denoted pPST216, pPST215, pPST213, pPST209, pPSSA216, pPSSA219, pPSSA220 and pPSG1, respectively, were transferred into dihydrofolate reductase (dhfr) deficient CHO DXB 11 cells (G. Urlaub and L. A. Chasin, Proc. Natl. Acad. Sci. USA. 77, 1980, pp. 4216–4220) using the calcium phosphate coprecipitation technique as described in (F. Graham and A. van der Eb, Virology 52, 1973, pp. 456–457). The cells were grown on solid support in α+MEM medium (Gibco) supplemented with 10% fetal calf serum (Gibco), streptomycin and penicillin. Conditioned medium was harvested after three days following transfection and the presence of EC-SOD variants in the medium was confirmed by ELISA and enzymatic activity measurements using the methods described above.

2.2. Plasmids pPS3 and pPST213, 10 μg of each, were mixed and cotransfected and the conditioned medium harvested three days following transfection in the same manner as described in Example 2.1. above and the distribution of EC-SOD variant proteins was analyzed using heparin-Sepharose ® chromatography as described in Example 5 below.

2.3. Two of the plasmids pPST216 and pPST213 (20 μg) carrying cDNA encoding variants T216 and T213, respectively, were separately mixed and cotransfected with plasmid pSV2 dhfr (0.5 μg (S. Subramani et al., Mol. Cell. Biol. 1, 1981, pp. 854–864) expressing dihydrofolate reductase. Stable transformants were selected in selective α-MEM medium lacking nucleosides (Gibco) supplemented with 10% dialyzed fetal calf serum (Gibco), streptomycin and penicillin. A number of individual transformants were isolated and expanded in the same medium and shown by ELISA and enzymatic measurements to secrete EC-SOD variants T216 and T213, respectively. For purification of variants T216 and T213 one of each transformant was expanded into ten 1,750 cm roller bottles in 50% α-MEM 50% Optimem medium (Gibco) supplemented with 0,5% newborn calf serum (Gibco), streptomycin and penicillin. The conditioned medium was changed every third day and the harvested medium was used in the purification of the EC-SOD variants as described in Example 6 and 8. As stated above, cell lines CHO DXB-11/pEE6-pSV2Ddhfr and CHO DXB-11/pEE7-pSV2dhfr harbouring plasmids pPST216 and pPST213, respectively, have been deposited on Sep. 14, 1989 in the European Collection of Animal Cell Cultures under the accesion numbers ECACC 89091402 and ECACC 89091403, respectively.

The results of the analytical separation of the various preparations are illustrated by the following figures which are further described in Examples 4 and 5 below.

Figure 4:
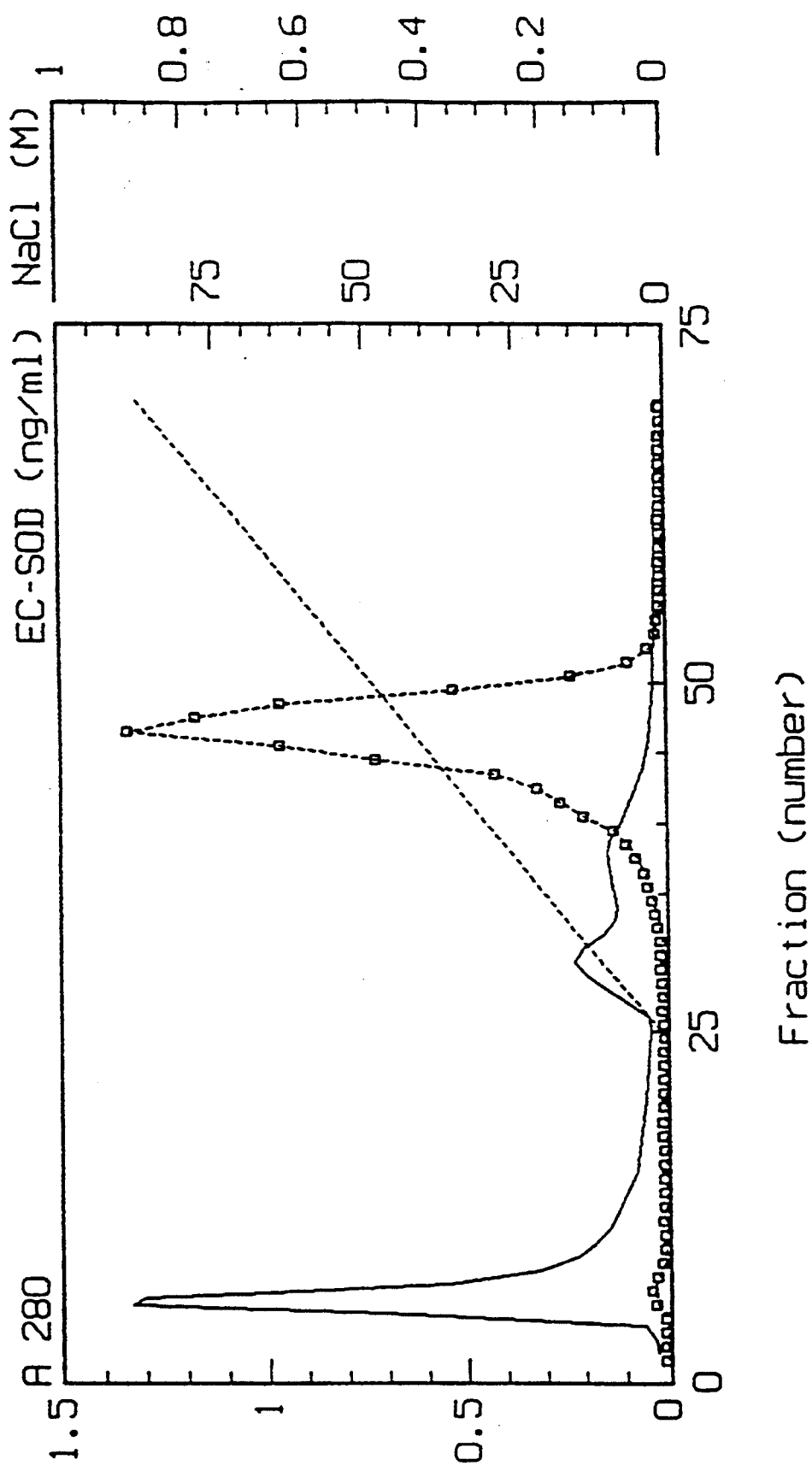
FIG. 4 is a graph showing the analytical separation of variant T216 by Heparin-Sepharose ® chromatography. Culture medium of Example 2 containing variant T216 was separated on Heparin-Sepharose ®, as described below in the Analytical Methods section, and EC-SOD content (right abscissa) of the fractions (□) determined by ELISA, as described below in the Analytical Methods section. The unbroken line represents absorbance at 280 nm (left abscissa). The dotted line represents the NaCl gradient (right abscissa).
Figure 5:
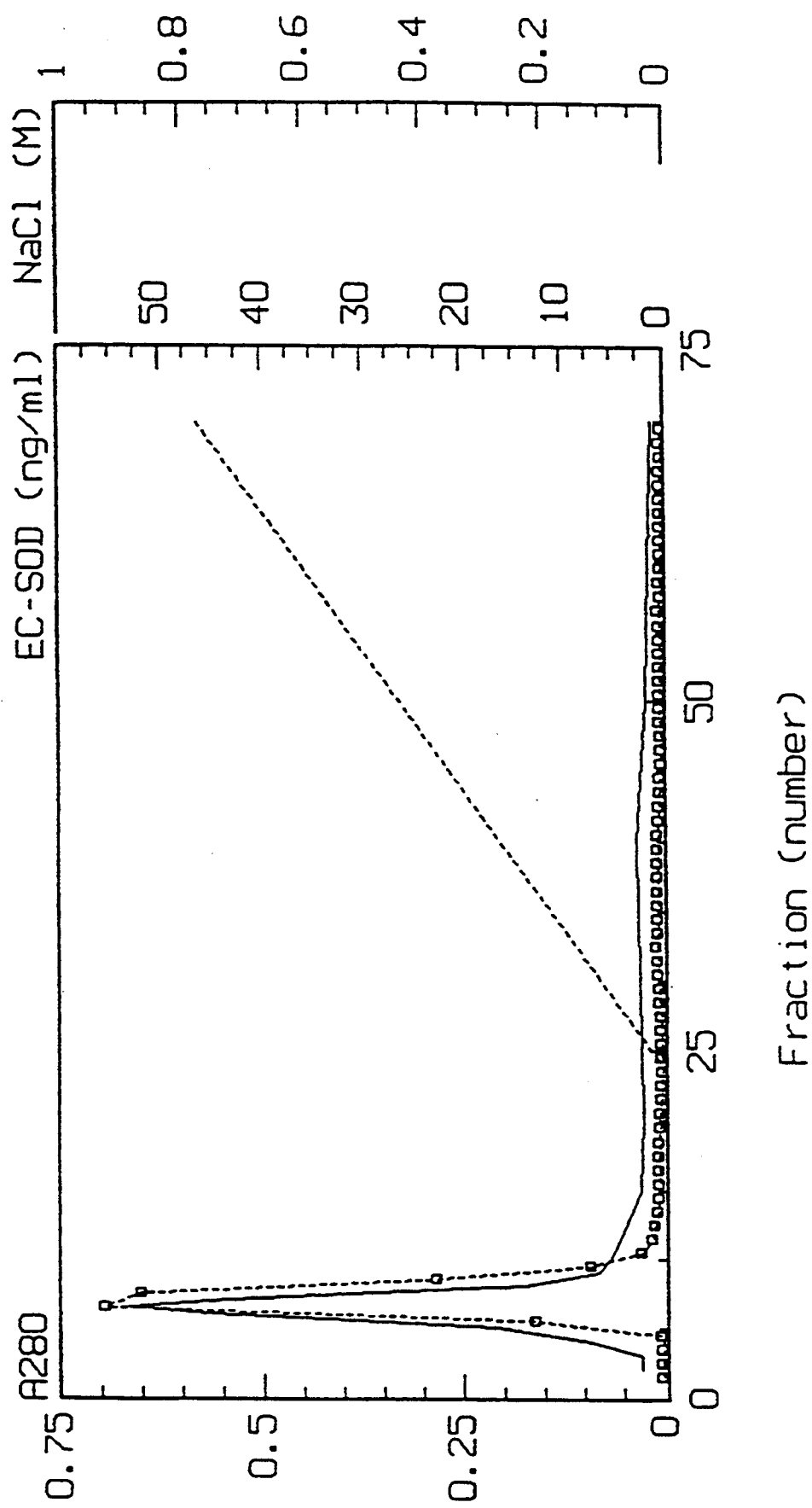
FIG. 5 is a graph showing the analytical separation of variant T215 by Heparin-Sepharose ® chromatography. Culture medium of Example 2 containing variant T215 was separated on Heparin-Sepharose ®, as described below in the Analytical Methods section, and EC-SOD content (right abscissa) of the fractions (□) determined by ELISA, as described below in the Analytical Methods section. The unbroken line represents absorbance at 280 nm (left abscissa). The dotted line represents the NaCl gradient (right abscissa).
Figure 6:
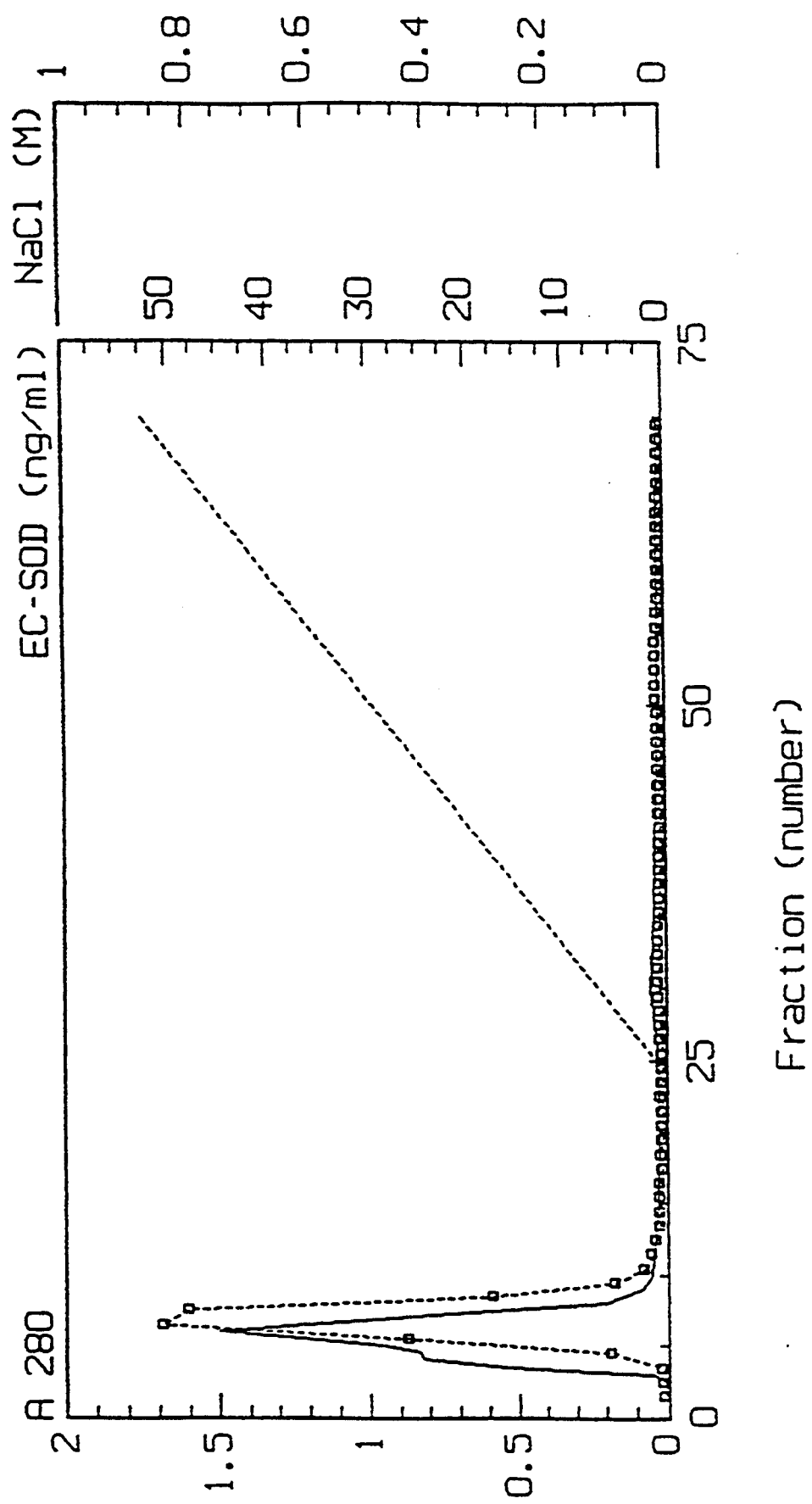
FIG. 6 is a graph showing the analytical separation of variant T213 by Heparin-Sepharose ® chromatography. Culture medium of Example 2 containing variant T213 was separated on Heparin-Sepharose ®, as described below in the Analytical Methods section, and EC-SOD content (right abscissa) of the fractions (□) determined by ELISA, as described below in the Analytical Methods section. The unbroken line represents absorbance at 280 nm (left abscissa). The dotted line represents the NaCl gradient (right abscissa).
Figure 7:
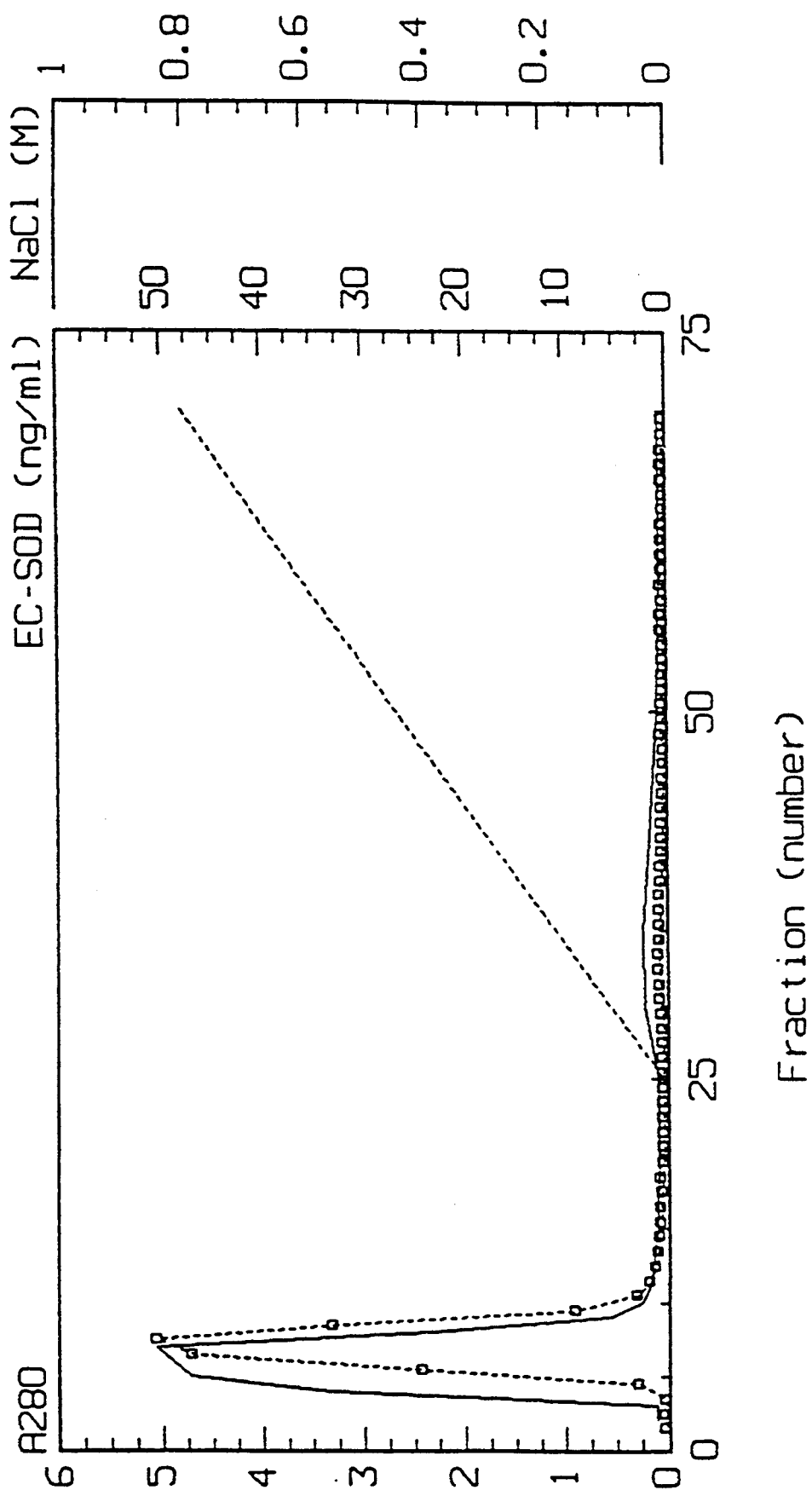
FIG. 7 is a graph showing the analytical separation of variant T209 by Heparin-Sepharose ® chromatography. Culture medium of Example 2 containing variant T209 was separated on Heparin-Sepharose ®, as described below in the Analytical Methods section, and EC-SOD content (right abscissa) of the fractions (□) determined by ELISA, as described below in the Analytical Methods section. The unbroken line represents absorbance at 280 nm (left abscissa). The dotted line represents the NaCl gradient (right abscissa).

FIG. 4 variant T216
FIG. 5 variant T215
FIG. 6 variant T213
FIG. 7 variant T209
FIG. 8A variant SA216
FIG. 8B variant SA219
FIG. 8C variant SA220
FIG. 8D variant G1
FIG. 9 Cotransfection of pPS3 and pPST213
FIG. 10 Cotransfection of pPST216 and pPST213
FIG. 11 Recombinant EC-SOD C and variant T213 incubated together for 23 hrs.

EXAMPLE 3

Plasma clearance of recombinant EC-SOD C in rabbits

For purposes of comparison with the EC-SOD variants, the plasma clearance of recombinant EC-SOD C (L. Tibell et al., Proc. Natl. Acad. Sci. USA. 84, 1987, pp. 6634–6638) was performed. The recombinant EC-SOD C was expressed from the cell line CHO-K1/pPS3neo-18 which is available from the European Collection of Animal Cell Cultures under the Accesion Number ECACC 86082701. The rabbits used were destination-bred Chinchilla ram rabbits of both sexes, age 5–6 months and weighing 3–6 kg. Each rabbit was used for only one experiment.

500 μg/kg body weight of the recombinant EC-SOD C dissolved in 50 ml K phosphate, pH 7.4, containing 0.2% bovine serum albumin (BSA), was injected into ear veins. Blood samples were tapped at times indicated in FIG. 12 into tubes containing EDTA as anticoagulant. Finally, 2,500 IU/kg body wt heparin was injected, and blood samples were tapped at 1, 5, and 15 min thereafter. After centrifugation at 2,000 g for 10 min, 1 ml plasma was collected and the human EC-SOD content was determined by ELISA in the Analytical Methods section above.

Plasma volume. In each animal, the plasma volume was determined by means of injecting, together with the recombinant EC-SOD C, a known amount of 125 I-labelled human serum albumin. The radioactivity of collected blood samples was determined by γ-ray detection. The counts were extrapolated to time zero for calculation of the plasma volume.

The results are shown in FIG. 12. It is seen that after intravenous injection, recombinant EC-SOD C is rapidly cleared from plasma, down to about 2–3% of the expected level (if all enzyme remained in plasma). If a large dose of heparin is injected after 20 min all sequestered (up to 100%) enzyme is released to plasma. Later injections, at 300 min and 24 hrs, result in less recovery of bound enzyme, but more than 30% is still released at 24 h. Available data (K. Karlsson and S. L. Marklund, Biochem. J. 242, 1987, pp. 55–59; K. Karlsson and S. L. Marklund, J. Clin. Invest. 82, 1988, pp. 762–766; K. Karlsson et al., Biochem. J. 256, 1988, pp. 29–33; S. L. Marklund and K. Karlsson, Lab. Invest. 60, pp. 695–666, 1989) indicate that the injected EC-SOD C is bound by heparan sulfate proteoglycan in the glycocalyx of vessel endothelium. When heparin is injected, the enzyme instead binds to the heparin, which has a higher affinity for EC-SOD C than heparan sulfate (K. Karlsson et al., Biochem. J. 256, 1988, pp. 29–33).

EXAMPLE 4

Analysis of the EC-SOD variants prepared in Examples 1 and 2

4.1. Variant T216

Variant T216 was produced as described in Examples 1 and 2. When separated on Heparin-Sepharose ® as described in the analytical method section above this variant eluted at about 0.42M NaCl (FIG. 4) and has thus a lower affinity than recombinant and native EC-SOD C which elutes at about 0.55M NaCl (L. Tibell et al., Proc. Natl. Acad. Sci. USA. 84, 1987, pp. 6634–6638). This variant thus belongs to C-class EC-SOD. Its molecular weight as deduced from gel chromatography was like recombinant EC-SOD C approximately 150 kDa and it is thus likely to be tetrameric. In this variant one positively charged amino acid, Lys 220, one negatively charged Glu 218, and 4 neutral amino acids were lost, a modification which resulted in a slightly reduced heparin affinity.

When intravenously injected into rabbits in the manner described for recombinant EC-SOD C in Example 3, variant T216, like EC-SOD C, is rapidly sequestered from the plasma, FIG. 13. However, considerably more, 20%–30%, remains in the plasma phase. Injection of heparin at 25 min, 120 min, 300 min and 24 h, resulted in a prompt release of variant T216 to plasma, indicating binding of the variant EC-SOD to heparan sulfate on vessel endothelium. However, in accordance with the reduced heparin affinity, as compared with that of native and recombinant EC-SOD C, the equilibrium between plasma and endothelium was considerably displaced towards the plasma phase, c.f. FIGS. 12 and 13.

4.2. Variant T215

Variant T215 was produced as described in Examples 1 and 2. Cell culture medium separated on Heparin-Sepharose ® as described in the analytical methods section above is illustrated in FIG. 5 which shows that this variant lacks affinity for Heparin-Sepharose ® and belongs to EC-SOD of class A. The total loss of heparin affinity was unexpected in view of the fact that only one negatively charged amino acid, Glu 216, had been removed. Further removal of amino acid residues as in variants T213 and T209 below, also resulted in A-class EC-SODs.

The presence of the part of the cluster with the highest charge-density, Arg-210, Lys-211, Lys-212, Arg-213, Arg-214, Arg-215, is thus suprisingly not sufficient for any heparin affinity.

4.3. Variant T213

Variant T213 was produced as described in Examples 1 and 2. Cell culture medium separated on Heparin-Sepharose ® as described in the analytical method section above (FIG. 6) shows that this variant lacks affinity for heparin and thus belongs to EC-SOD class A. Its molecular weight as determined from gel chromatography was like recombinant EC-SOD C approximately 150 kDa and is thus likely to be tetrameric.

When variant T213 was intravenously injected into rabbits, apparently all enzyme remained in the plasma phase, FIG. 14. Injection of heparin at 300 min and 24 h, led to no significant release of this variant enzyme i.e. there was no evidence for binding of A-class EC-SOD to vessel endothelium.

4.4. Variant T209

Variant T209 was produced as described in Examples 1 and 2. When medium containing the variant is separated on Heparin-Sepharose ® as described in the analytical method section above (FIG. 7), it is found that this variant lacks affinity for heparin and thus belongs to EC-SOD class A.

4.5. Variant SA216

Variant SA216 was produced as described in Examples 1 and 2. Cell culture medium separated on Heparin-Sepharose ® as described in the analytical method section above (FIG. 8A) shows a peak eluting at 0.6M NaCl and thus has a higher affinity for heparin than recombinant and native EC-SOD C. In this variant one negatively charged amino acid, Glu 216, has been substituted with one neutral amino acid, Ala.

4.6. Variant SA219

Variant SA219 was produced as described in Examples 1 and 2. Cell culture medium separated on Heparin-Sepharose ® as described in the analytical method section above (FIG. 8B) shows a peak eluting at about 0.55M NaCl and thus has the same affinity as recombinant and native EC-SOD C. In this variant one cystein residue, Cys 219, has been substituted with one Ala. This excludes the possibility that Cys 219 is engaged in a S-S bridge that is involved in maintaining the correct structure of the C-terminal to obtain heparin affinity. The fact that the variant SA219 has the same affinity as recombinant EC-SOD C illustrates that the substitution of a neutral amino acid (Cys) with another neutral amino acid (Ala) apparently has no effect on the heparin binding affinity. Thus, it is illustrated that the heparin binding affinity remains unchanged when the net charge of this variant is unchanged.

4.7. Variant SA220

Variant SA220 was produced as described in Examples 1 and 2. Cell culture medium separated on Heparin-Sepharose ® as described in the analytical method section above (FIG. 8C) shows a peak eluting at 0.5M NaCl and thus has a slightly reduced affinity for heparin. In this variant one positively charged amino acid, Lys 220, has been substituted with one neutral amino acid Ala.

4.8 Variant SAT216

Variant SAT216 was produced as described in Examples 1 and 2. Cell culture medium separated on Heparin-Sepharose ® as described in the analytical method section above (FIG. 8E) shows a peak eluting at 0.51M NaCl and thus has a lower affinity than recombinant and native EC-SOD C. In this variant amino acid Glu 216 has been substituted with the amino acid Ala and the rest of the C-terminal has been truncated. This variant has the same amino acid chain length as variant T216, but the negatively charged amino acid Glu 216 has been substituted with a neutral amino acid Ala, thus taking away one negative charge from the C-terminal, and hence giving it a higher net positive charge and a higher affinity for heparin than variant T216.

Variant T215 which contains the part of the amino acid cluster with the highest charge density, Arg 210, Lys 211, Lys 212, Arg 213, Arg 214, Arg 215, completely lacks heparin affinity, whereas variants T216 and SAT216 with Glu and Ala, respectively, in position 216 both being only one amino acid longer, both have high heparin affinity. Surprisingly, the high positive charge density cluster is not sufficient for a high heparin affinity. It appears that still one more amino acid residue is needed to obtain a conformation resulting in heparin affinity.

4.9. Variant G1

Variant G1, a glycosylation-free variant, was produced as described in Examples 1 and 2. Analytical separation on Heparin-Sepharose ® as described in the analytical method section above (FIG. 8D) shows two peaks, one eluting at 0.38M NaCl and one with very high heparin affinity which elutes at 0.64M NaCl. Its molecular weight as determined from gel chromatography performed as described in the analytical method section above was 95.5 kDa, very similar to the figure expected for a tetramer with a subunit molecular weight of 24.2 kDa subunit, the molecular weight calculated from the EC-SOD C amino acid content.

The absence of carbohydrate in this variant was demonstrated by the lack of binding to the lectin concanavalin A immobilised on Sepharose ®. Culture medium containing variant G1 was passed through a Con A-Sepharose ® column (Pharmacia LKB Biotechnology Inc.) as previously described for native and recombinant EC-SOD C (L. Tibell et al., Proc. Natl. Acad. Sci. USA. 84, 1987, pp. 6634–6638). In brief, following application of the culture medium, the Con A-Sepharose ® column was eluted first with sodium phosphate buffer, and then, in order to free any bound EC-SOD, with 0.5M methyl α-mannoside. The degree of binding to concanavalin A was calculated from the SOD activity (determined as described in the Analytical Methods section) of the eluates. In contrast to EC-SOD C, the EC-SOD-ELISA reactive material of the variant G1-containing culture medium did not bind to the lectin concanavalin A.

At present there is no explanation for the heterogeneity in heparin affinity. An increased heparin affinity may be due to the fact the carbohydrate substituent of EC-SOD carries a considerable negative charge that may repel the enzyme from the strongly negatively charged heparin. A removal of this effect may increase the heparin affinity.

EXAMPLE 5

Analysis of the heterotetramers of EC-SOD produced in Example 2

5.1. Cotransfection of plasmid pPST213 and pPS3

Plasmids pPST213 and pPS3 were cotransfected as described in Example 2.3 above. The resulting culture medium was separated on Heparin-Sepharose ® as described in the analytical method section above (FIG. 9). The chromatogram contained one non-binding peak of class A (similar to what is obtained when pPST213 is transfected alone) and one strongly binding peak eluting at about 0.52M NaCl (similar to the peak obtained upon transfection of only pPS3, that is recombinant EC-SOD C). In addition two weaker binding peaks eluting at 0.18 and 0.28M NaCl are seen. These would by definition belong to B-class EC-SOD.

5.2. Cotransfection of plasmid pPST216 and pPST213

Plasmid pPST216 and pPST213 were cotransfected as described in Example 2.2 above. The resulting culture medium was separated on Heparin-Sepharose ® as described in the analytical method section above (FIG. 10). The chromatogram contained one non-binding peak of class A (similar to what was obtained when pPST213 was transfected alone) and one relatively strongly binding peak eluting at about 0.40M NaCl (similar to the peak obtained upon transfection of only pPST216). In addition two weaker binding peaks eluting at 0.13 and 0.23M NaCl are seen. These would by definition belong to B-class EC-SOD.

5.3. Coincubation of recombinant EC-SOD C and variant T213

Culture media containing variant T213 (prepared as described above, Example 2) and recombinant EC-SOD C (L. Tibell et al., Proc. Natl. Acad. Sci. USA. 84, 1987, pp. 6634–6638) were mixed (about 100 ng/ml in α-medium containing 10% fetal calf serum (Gibco)) so as to produce a solution containing initially nearly equal amounts of each variant. The mixture was incubated at 37° C. Analytical separation of the mixture (after different incubation times) on Heparin-Sepharose ® as described in the Analytical Methods section above resulted in the pattern seen in FIG. 11 which illustrates samples taken shortly after mixing and after 23 hrs of coincubation. One non-binding class A peak is seen (corresponding to that which is obtained when variant T213 is analyzed, FIG. 6) and one strongly binding peak eluting at 0.40M NaCl (similar to what is obtained when recombinant EC-SOD C alone is analyzed). In addition a broad peak eluting at 0.28M NaCl is seen, belonging by definition to class B EC-SOD.

Conclusion

Cotransfection of pPST213/pPST216 and pPST213/pPS3 thus resulted, in addition to formation of the parental types, in the formation of two intermediate B-class forms. In the case of pPST213/pPST216 the heparin affinities of the B-forms were a little lower than in the case of pPST213/pPS3. This is in accord with the lower heparin affinity of variant T216 compared with recombinant EC-SOD C. In the coincubation experiment with variant T213 and recombinant EC-SOD C, a B-class intermediate was also gradually formed. This intermediate had a heparin affinity equal to that of the stronger binding B-class intermediate of the cotransfection experiment with the corresponding plasmid combination. Taken together these results strongly suggest that B-class EC-SODs are heterotetramers of A- and C-class monomers. The most likely compositions are the following (small letters denote subunits):
  cccc for C-class;
  ccca and ccaa for the two B-class peaks respectively; and caaa and aaaa for A-class EC-SOD.

EXAMPLE 6

Purification of EC-SOD variant T216

Variant T216 was prepared as described in Examples 1 and 2. The resulting transfected cells were expanded and finally 2,930 ml culture medium containing 748 units SOD activity and 4,750 µg EC-SOD (ELISA) per ml was obtained.

6.1. Separation on Q-Sepharose ®

The culture medium was applied to a Q-Sepharose ® column (Pharmacia LKB Biotechnology Inc.), 104 ml, equilibrated with 50 mM K phosphate, pH 7.6. The medium was applied at 360 ml/h and the column was then washed with 200 ml equilibration buffer at the same rate. Bound enzyme was then eluted at 360 ml/h with 400 mM K phosphate, pH 7.6 (FIG. 15). Eluted fractions were analyzed for SOD activity. The peak of SOD activity was pooled as indicated in the figure.

6.2. Separation on Phenyl-Sepharose ®

The pool from the Q-Sepharose ® step was dialyzed against 600 mM Na phosphate, pH 7.6, and was then applied at 165 ml/h to a Phenyl-Sepharose ® column (Pharmacia LKB Biotechnology Inc.), 10 ml, equilibrated with 600 mM Na phosphate. The column was then washed with 125 ml equilibration buffer. Bound enzyme was finally eluted with 10 mM Na phosphate, pH 7.6, as seen in FIG. 16. The enzyme was pooled as indicated in the figure.

6.3. Separation on Heparin-Sepharose ®

The pool from the Phenyl-Sepharose ® step was dialyzed against 0.1M Na phosphate, pH 7.6, and then applied at 45 ml/h on a Heparin-Sepharose ® column, 10 ml equilibrated with 0.1M Na phosphate, pH 7.6. The column was then washed with 33 ml equilibration buffer. Bound enzyme was finally eluted with a gradient in NaCl (0–1M) in the equilibration buffer and the SOD activity was determined in collected fractions as described in the analytical method section above. Eluted enzyme was pooled as indicated in FIG. 17 and finally concentrated.

EXAMPLE 7

Analyses on isolated EC-SOD variant T216

The results of the purification steps performed in Example 6 are summarized in Table X.

The final specific activity (units SOD activity per ml/absorbance at 280) 67,000 is similar to that previously obtained for recombinant EC-SOD C, 69,400 (L. Tibell et al., Proc. Natl. Acad. Sci. USA. 84, 1987, pp. 6634–6638).

The purity of the isolated EC-SOD variant T216 was determined by means of polyacrylamide gel electrophoresis in the presence of sodium dodecylsulfate, as described in the legend to FIG. 18, and the identity as a human EC-SOD by means of Western blotting, as described in the legend to FIG. 19. No impurity could be detected by the polyacrylamide gel electrophoresis. Partially purified variant T213, as obtained in Example 8, was also electrophoresed (FIG. 18) and its identity determined by Western blotting (FIG. 19). As can be seen, there is a distinct decline in apparent molecular weights going from recombinant EC-SOD C, to variant T216 and to variant T213. This is in accord with the decreasing molecular weights resulting from the carboxyterminal truncations.

Table X. Isolation of EC-SOD variant T216

Results after each separation step are shown. The SOD activity was determined by means the direct spectrophotometric method employing $KO_2$ (S. Marklund, J. Biol. Chem. 251, 1976, pp. 7504–7507). One unit corresponds to 8.6 ng native and recombinant human EC-SOD C (L. Tibell et al., Proc. Natl. Acad. Sci. USA. 84, 1987, pp. 6634–6638).

|  | SOD activity (units) | Specific activity (units per ml/$A_{280}$) | Recovery % |
|---|---|---|---|
| Culture medium | 1,328,000 | — | 100% |
| 1. Q-Sepharose ® | 1,091,000 | 10,555 | 82.1% |
| 2. Phenyl-Sepharose ® | 969,000 | 21,440 | 73% |
| 3. Heparin-Sepharose ® | 553,700 | 67,034 | 41.7% |

EXAMPLE 8

Partial purification of EC-SOD variant T213

Variant T213 was prepared as described in Examples 1 and 2. The resulting transfected cells were expanded and finally 860 ml culture containing 162.5 units SOD activity per ml was obtained.

8.1. Anti EC-SOD-Sepharose ®

Monoclonal anti-human EC-SOD antibody 14-B7 (which is described in, and produced according to, Example 15 of WO 87/01387) was coupled to CNBr-activated Sepharose ® 4B (Pharmacia LKB Biotechnology Inc.) at a concentration of 2 mg/ml gel. The gel, 28 ml, was packed in a chromatography column and equilibrated with 50 mM 1-aminomethyl-propanol hydrochloride pH 9.0/0.5M NaCl. The culture medium was applied at 100 ml/h. Unexpectedly no binding of the EC-SOD variant occurred. This monoclonal antibody had previously successfully been employed for the isolation of native and recombinant EC-SOD C (L. Tibell et al., Proc. Natl. Acad. Sci. USA. 84, 1987, pp. 6634–6638). The affinity of the various EC-SOD variants for the immobilized antibody was subsequently tested. It was found that variants T213 and T209, which lack binding to heparin and thus belong to the A-class, also lack affinity for the antibody. On the other hand native and recombinant EC-SOD C and variant T216, which belongs to the C-class EC-SOD were all bound by the antibody. This monoclonal antibody, 14-B7, thus has its specificity directed towards a functional heparin-binding site of EC-SODs.

8.2. Separation on Q-Sepharose ®

After direct passage through the anti EC-SOD-Sepharose ® column the medium containing variant T213 (875 ml, 145.6 SOD units per ml) was applied to a Q-Sepharose ® column (Pharmacia LKB Biotechnology Inc.), 40 ml, equilibrated against 50 mM K phosphate pH 7.6 at 300 ml/h. The column was then washed with equilibration buffer. Bound enzyme was then eluted with a gradient in K phosphate, pH 6.0, 50–300 mM, FIG. 20.

The SOD activity was determined in collected fractions and the peak was pooled in two fractions, I and II.

8.3. Chromatography on Heparin-Sepharose ®

Pool I (139 ml) was concentrated to 12 ml and dialyzed against 25 mM K phosphate, pH 6.5. It was then applied to a Heparin-Sepharose ® column, 5 ml, equilibrated against 25 mM K phosphate, pH 6.5. The SOD activity eluted without binding to the column, and thus represented EC-SOD of class A. The eluted enzyme was pooled, the total SOD activity of which was 43,000 units. According to ELISA as described in the analytical method section above the EC-SOD content was 740 μg. One unit thus corresponded to 17 ng EC-SOD protein, a figure not far away from the one previously obtained for native and recombinant EC-SOD C (L. Tibell et al., Proc. Natl. Acad. Sci. USA. 84, 1987, pp. 6634–6638). The variant T213 could easily be detected upon electrophoresis in polyacrylamide gel in the presence of sodium dodecylsulfate as described in the legend to FIG. 18. The identity of the protein as EC-SOD was established by means of Western blotting, as described in the legend to FIG. 19.

We claim:

1. A non-naturally occurring EC-SOD-like polypeptide, comprising an amino acid sequence substantially corresponding to amino acids 1–222 of human EC-SOD type C as given in FIGS. 1A and 1B, except that said polypeptide lacks glycosylation sites,
where said polypeptide exhibits superoxide dismutasing and heparin binding activities, and also exhibits increased heparin binding relative to human EC-SOD type C.

2. The polypeptide of claim 1 in which amino acid Asn 89 of human EC-SOD type C is replaced by Ser.

3. The polypeptide of claim 1 in purified form.

4. The polypeptide of claim 2 in purified form.

5. The polypeptide of claim 1, wherein said polypeptide is bound by an antibody which binds human EC-SOD type C but does not bind human CuZnSOD.

6. The polypeptide of claim 1, wherein the sequence corresponding to residues 194–222 of human EC-SOD type C has a higher net charge than residues 194–222 of human EC-SOD type C.

7. The polypeptide of claim 6 wherein the residue corresponding to Glu216 of human EC-SOD type C is Ala.

8. The polypeptide of claim 1 wherein the peak elution of the polypeptide from an immobilized heparin chromatography is at about 0.64 molar aqueous NaCl.

9. A composition comprising the polypeptide of claim 1 in tetrameric form.

10. A non-naturally occurring or purified DNA molecule comprising a DNA sequence encoding the polypeptide of claim 1.

11. A non-naturally occurring or purified DNA molecule comprising a DNA sequence encoding the polypeptide of claim 2.

12. A replicable expression vector comprising a DNA sequence encoding the polypeptide of claim 2.

13. A cell transformed by a vector according to claim 12, and expressing said polypeptide under suitable conditions.

14. A method for preventing or treating a disorder at least in part caused by or exacerbated by the presence or formation of superoxide radicals, wherein the disorder is damage caused by ischemia followed by reperfusion, or in connection with the transplantation of organs selected from the group consisting of kidney, lung, pancreas, liver, skin, bone tissue, extremities, skeletal muscle, lens, and cornea, or in connection with heart surgery, comprising administering a therapeutically or prophylactically effective amount of a polypeptide or a polypeptide composition according to claim 1 before, during or after surgery.

* * * * *